(12) United States Patent
Endou et al.

(10) Patent No.: US 7,345,068 B2
(45) Date of Patent: Mar. 18, 2008

(54) AROMATIC AMINO ACID DERIVATIVES AND MEDICINAL COMPOSITIONS

(75) Inventors: Hitoshi Endou, 1-23-7, Yoshinodai, Sagamihara-shi, Kanagawa (JP) 229-0022; Yoshikatsu Kanai, Tokyo (JP); Kenji Tsujihara, Saitama (JP); Kunio Saito, Saitama (JP)

(73) Assignee: Hitoshi Endou, Sagamihara-shi (JP)

( * ) Notice: Subject to any disclaimer, the term of this patent is extended or adjusted under 35 U.S.C. 154(b) by 226 days.

(21) Appl. No.: 10/503,125

(22) PCT Filed: Feb. 3, 2003

(86) PCT No.: PCT/JP03/01081

§ 371 (c)(1),
(2), (4) Date: Feb. 9, 2005

(87) PCT Pub. No.: WO03/066574

PCT Pub. Date: Aug. 14, 2003

(65) Prior Publication Data
US 2005/0119256 A1 Jun. 2, 2005

(30) Foreign Application Priority Data
Feb. 7, 2002 (JP) .............................. 2002-031216

(51) Int. Cl.
C07D 235/14 (2006.01)
C07D 263/57 (2006.01)
A61K 31/54 (2006.01)
A61K 31/4745 (2006.01)

(52) U.S. Cl. ...................... 514/367; 514/375; 514/394; 514/419; 514/469; 514/464; 548/179; 548/217; 548/309.7; 548/492; 549/440; 549/469

(58) Field of Classification Search ................ 548/179, 548/217, 309.7, 492; 549/440, 469; 514/367, 514/375, 394, 419, 469, 464
See application file for complete search history.

(56) References Cited

U.S. PATENT DOCUMENTS
5,364,876 A 11/1994 Hamilton

FOREIGN PATENT DOCUMENTS
| WO | 96 38415 | 12/1996 |
| WO | 96 40745 | 12/1996 |
| WO | 98 00137 | 1/1998 |
| WO | 00 71101 | 11/2000 |
| WO | WO 2004/037810 A1 | 5/2004 |

OTHER PUBLICATIONS

Kaiser et al. Ange. Chem. Int. Ed. 2002, 41, No. 5, pp. 780-783.*
Cox et al. Journal of Medicinal Chemistry 1974, vol. 17, No. 10, 1125-1127.*
Konopelski et al., Synlett 1996, 7, 609-611.*
Sucholeiki, Irving et al. "New polyoxyalkyteneamine-grafted paramagnetic supports for solid-phase synthesis and bioapplications", Tetrahedron Letters, vol. 42, pp. 3279-3282 2001.
Koehrle, Josef et al. "Rat Liver Iodothyronine Monodelodinase", The Journal of Biological Chemistry, vol. 261, No. 25, pp. 11613-11622 1986.
Blaney, Jeffery M. et al. "Computer Graphics in Drug Design: Molecular Modeling of Thyroid Hormone-Prealbumin Interactions", J.Med.Chem. vol. 25, pp. 785-790 1982.

(Continued)

Primary Examiner—Kahsay Habte
(74) Attorney, Agent, or Firm—Oblon, Spivak, McClelland, Maier & Neustadt, P.C.

(57) ABSTRACT

1. An aromatic amino acid derivative represented by the formula (I) or its pharmacologically acceptable salt:

$$\underset{R^1NH}{\overset{H_{\prime\prime\prime}}{\diagdown}}\underset{COOR^2}{\diagdown}\text{---}\!\!\!\diagup\!\!\!\!\!\diagdown\text{(Y)}_l\text{---}(CH_2)_n\text{---}R^3\qquad (X)_m \qquad (I)$$

wherein,
$R^1$ is a hydrogen atom or an amino-protecting group,
$R^2$ is a halogen atom or an alkyl, aralkyl or aryl group,
$R^3$ is ① a hydrogen atom, ② an aroylamino group, ③ a phenyl group substituted with lower alkyl, phenyl, phenoxy, etc. ④ a naphthyl or tetrahydronaphthyl group optionally substituted with hydroxy, lower alkoxy or di(lower)alkylamino, ⑤ an unsaturated mono-cyclic heterocyclic group containing N, O and/or S substituted with lower alkyl, phenyl, naphthyl or tetrahydroquinolyl, ⑥ an unsaturated or partially saturated condensed heterocyclic group containing N, O and/or S, optionally substituted with oxo, carboxy, amino, lower alkyl, etc.; X is a halogen atom, an alkyl group or an alkoxy group; Y is oxygen atom or nitrogen atom; l is 0 or 1; m is 0, 1 or 2; n is an integer of 0-5. This compound can inhibit a transporter (LAT1) of essential amino acid which is one of main nutrition for cancer cells and accordingly cause drain of the essential amino acid on the cancer cells and finally can prohibit the multiplication of cancer cells.

13 Claims, 3 Drawing Sheets

OTHER PUBLICATIONS

Dietrich, Stephen W. "Thyroxine Analogues. 23. Quantitive Structure-Activity Correlation Studies of in Vivo and in Vitro Thyromimetic Activities", J.Med.Chem. vol. 20, No. 7 pp. 863-880 1977.

Jorgensen, Eugene C. et al. "Thyroxine Analogs. 20. Substituted 1- and 2- Naphthyl Ethers of 3,5-Dilodotyrosine", J.Med.Chem. vol. 14, No. 11, pp. 1023-1026 1971.

Virginia B. Schatz, et al, "Iodinated Phenylalanines. Tests for Selective Localization in Pancreas and Preparation of 3,4,5-Triiodophenylalanine", Journal of Medicinal Chemistry, vol. 11, No. 1, XP-002439147, 1968, pp. 140-142.

Richard Leduc, et al., "96. Angiotensin-II Analogues. I: Synthesis and Incorporation of the Halogenated Amino Acids 3-(4'-Iodophenyl) alanine, 3-(3', 5'-Dibromo-4'-chlorophenyl)alanine, 3-(3', 4',5'-Tribromophenyl) alanine, and 3(2',3',4',5',6'-Pentabromophenyl) alanine)", Helvitica Chimica Acta, vol. 66, fasc. 3, XP-009058287, pp. 960-970, 1983.

Benjamin Blank, et al., "Thyromimetics. I. The Synthesis and Hypocholesteremic Activity of Som 3' and 3',5'-Alkyl and Aryl-3,5-diiodothyronines", Journal of Medicinal Chemistry, vol. 6, XP-002439148, 1963, pp. 554-560.

George A. Brine, et al., "Potential Internal Standards for the Reversed-Phase High Performance Liquid Chromatography Analysis of Thyroidal Amino Acids", Analytical Letters, vo. 15 (B11), 1982, pp. 923-935.

Database Caplus [Online], Chemical Abtracts, Database Accession No. 2006:991603, XP-002439150, CN 1 287 860, Mar. 21, 2001.

* cited by examiner

Concentration (μM) of aromatic amino acid derivative

Concentration (μM) of aromatic amino acid derivative

AROMATIC AMINO ACID DERIVATIVES AND MEDICINAL COMPOSITIONS

TECHNICAL FIELD

This invention relates to novel aromatic amino acid derivatives and a pharmaceutical composition containing said derivative as an active ingredient.

BACKGROUND OF ART

Most of conventional chemotherapeutic agents for cancer exert an anticancer effect by directly inhibiting DNA biosynthesis of cells and act effectively against tumors that are active in cell division.

However, since normal cells as well as cancer cells are in vivo active in cell division, the existing chemotherapeutic agents for cancer are insufficient in selective toxicity to cancer cells, causing strong side effects. Therefore, there has been a problem in that chemotherapeutic agents for cancer are not able to be administered in an amount enough to exert their anticancer effect.

Further, in contrast to the chemotherapy that directly kills cancer cells, there have been attempted a differentiation-inducing therapy that induces differentiation of cancer cells to put them back to normal cells, hyperthermia which takes advantage of vulnerability of cancer cells to heat, a vasopressor chemotherapy which makes use of undeveloped blood circulatory system of cancer cells and their peculiarity, a method utilizing drug delivery system (DDS), as well as a missile treatment using a monoclonal antibody which attacks cancer cells only or the same antibody condensed with an anticancer agent.

In recent years, analysis of characteristics of cancer cells and a canceration mechanism has rapidly progressed at a molecular and genetic level. Accordingly, unprecedented approaches to the cancer therapy aimed at a new target have been attempted, for example, a method using a drug resistance overcoming agent, a cancer metastasis inhibitor or a vascularization inhibitor, as well as a gene therapy using a gene-carrying vector.

However, there has not been found a satisfactory anticancer agent or therapy that surely inhibits cancer proliferation and hardly causes side effects. Therefore, development of them has been longed for.

In general, cancer cells repeat rapid proliferation. Therefore, uptake of essential amino acids which cannot be produced by intracellular metabolism is abnormally accentuated.

The inventors of the present invention have succeeded in molecular cloning of a cancer-specific L-type amino acid transporter, which is a membrane protein required for intracellular uptake of neutral branched-chain amino acids and aromatic amino acids containing many essential amino acids, and named it as L-type amino acid transporter 1 (LAT1) (Kanai Y. et al., Journal of Biological Chemistry, 273, 23629(1998)). It has also been confirmed that an L-type amino acid transporter (LAT2), which is a membrane protein indispensable for uptake of the essential amino acids, exists even in normal cells (Japanese Unexamined Patent Publication No. 2000-342270 etc.).

Accordingly, it is considered that screening of substances which strongly act against LAT1 allows specifically inhibiting the expression of LAT1, which may possibly constitute the rate-determining step of the cancer cell proliferation.

As the only compound which specifically inhibits the amino acid transport system L (LAT), 2-aminobicyclo-(2,2,1)-heptane-2-carboxylic acid (BCH) is known. However, its inhibiting action is very weak and there has not been reported that it has an inhibiting action against the cancer cell proliferation.

DISCLOSURE OF THE INVENTION

In view of the above problems, the present invention has been achieved. An object of the present invention is to find novel low molecular compounds which strongly inhibit LAT1, which is expressed specifically to cancer cells, and to find low molecular weight compounds which also act against LAT2, thereby to provide new anticancer agents for inhibiting the cancer cell proliferation and a drug that exerts an additional action respectively.

In order to develop novel anticancer agent capable of inhibiting the cancer cell proliferation by strongly inhibiting LAT1 and to develop agents capable of acting also against LAT2 selectively or nonselectively, the inventors of the present invention have synthesized various novel amino acid derivatives and studied their LAT1 inhibiting activity, LAT2 inhibiting activity, as well as selectivity between LAT1/LAT2. Then, it was confirmed that aromatic amino acid derivatives of the present invention show excellent LAT1 inhibiting activity and inhibit the cancer cell proliferation. Thus, the present invention has been achieved.

That is, according to the present invention, aromatic amino acid derivatives represented by the formula (I) or its pharmacologically acceptable salt can be provided:

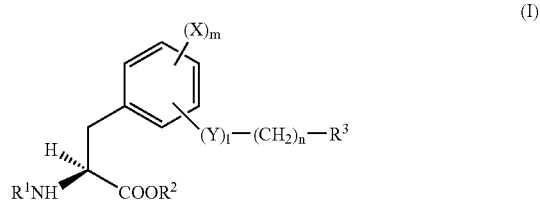

(I)

wherein,

R$^1$ is a hydrogen atom or an amino-protecting group,

R$^2$ is a hydrogen atom or an aryl, aralkyl or alkyl group,

R$^3$ is ① a halogen atom, ② an aroylamino group in which the amino moiety may be optionally substituted with lower alkyl, ③ a phenyl group substituted with lower alkyl, phenyl, phenoxy, pyridyl, pyrimidinyl or quinolyl in which each substituent on the phenyl group may be further substituted with halogen atom, cyano, hydroxy, carboxy, lower alkoxy, lower alkoxycarbonyl, phenyl, di-lower alkylamino or thiomorpholinyl, ④ a naphthyl or tetrahydronaphthyl group optionally substituted with hydroxy, lower alkoxy or di-lower alkylamino, in which the di-lower alkylamino may be further substituted with halogen atom or hydroxy, ⑤ an unsaturated mono-cyclic heterocyclic group containing N, O and/or S substituted with lower alkyl, phenyl, naphthyl or tetrahydroquinolyl, in which each substituent on the mono-cyclic heterocyclic group may be further substituted with halogen atom, hydroxy or phenyl, ⑥ an unsaturated or partially saturated condensed heterocyclic group containing N, O and/or S, optionally substituted with oxo, carboxy, amino, lower alkyl, lower alkoxy, cycloalkyl, di-lower alkylamino, lower alkoxycarbonyl, di-lower alkylcarbamoyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di-lower alkylamino, lower alkanoyloxy, bis[halo(lower)alkyl]amino or N-(lower)alkyl-N-hydroxy(lower)alkylamino, X is a halogen atom, an alkyl group or an alkoxy group,
Y is O or NH
l is 0 or 1,
m is 0, 1 or 2,
n is an integer of 0-5.

Further, according to the present invention, is provided a pharmaceutical composition containing the aromatic amino acid derivatives of the formula (1) or a pharmacologically acceptable salt thereof as an active ingredient. In particular, is provided a pharmaceutical composition useful as an inhibitor of the L-type amino acid transporter.

With this inhibitor, a transporter (LAT1) of essential amino acids, which are one of major nourishment for cancer cells, is inhibited to cause depletion of the essential amino acids in cancer cells, thereby permitting inhibition of the proliferation of cancer cells. Further, it allows inhibition of vascularization associated with malignancy, as well as vascularization associated with proliferative lesions on retina such as diabetic retinopathy. Further, inhibiting activity is also expected against diseases accompanied by cell proliferation, for example, various inflammatory diseases and excessive granulation in an injury treatment process. Moreover, if the inhibitor possesses not only the LAT1 inhibiting activity but also the LAT2 inhibiting activity, it can exert an action of controlling absorption and internal distribution of poisonous substances transported by the transport system L, for example, methyl mercury. In particular, if the LAT2 selectivity is higher, it is expected, in addition to the above action, an action of inhibiting harmful effects caused by accentuation of amino acid metabolism in the cells, for example, hyperglycemia by accentuation of gluconeogenesis, skeletal muscular atrophy caused physiologically or in association with various diseases, and accentuated bone resorption.

BEST MODE FOR CARRYING OUT THE INVENTION

Figure 1:
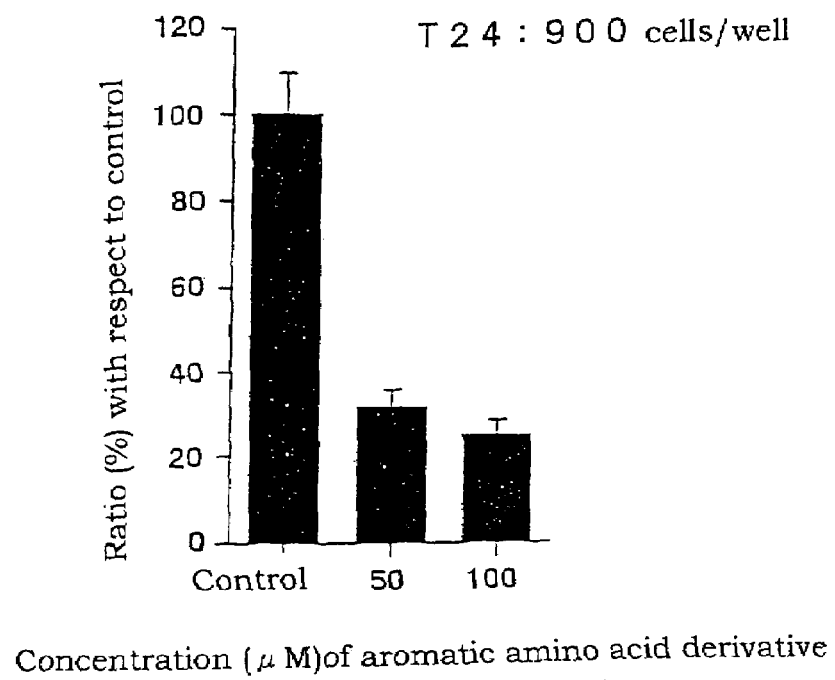
FIG. 1 is a graph showing activity inhibiting multiplication of cancer cells by an aromatic amino acid derivative (Example 6) of the present invention.
Figure 2:
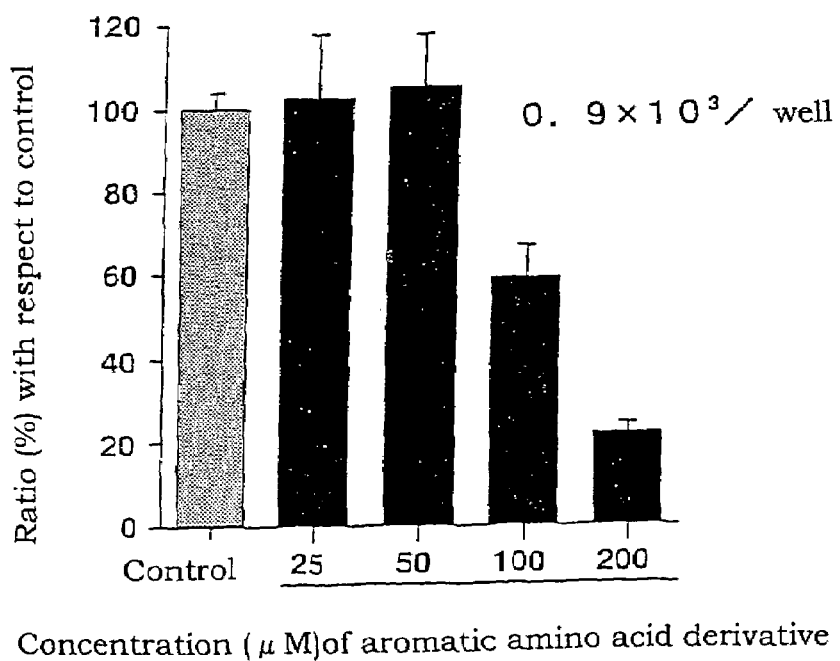
FIG. 2 is a graph showing activity inhibiting multiplication of cancer cells by another aromatic amino acid derivative (Example 9) of the present invention.
Figure 3:
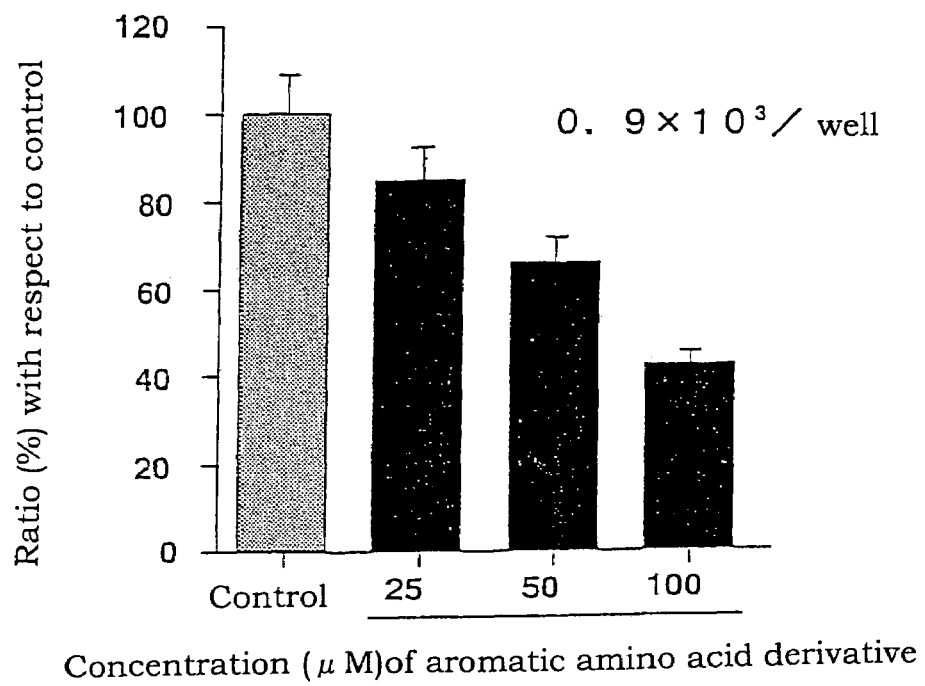
FIG. 3 is a graph showing activity inhibiting multiplication of cancer cells by further another aromatic amino acid derivative (Example 15) of the present invention.
Figure 4:
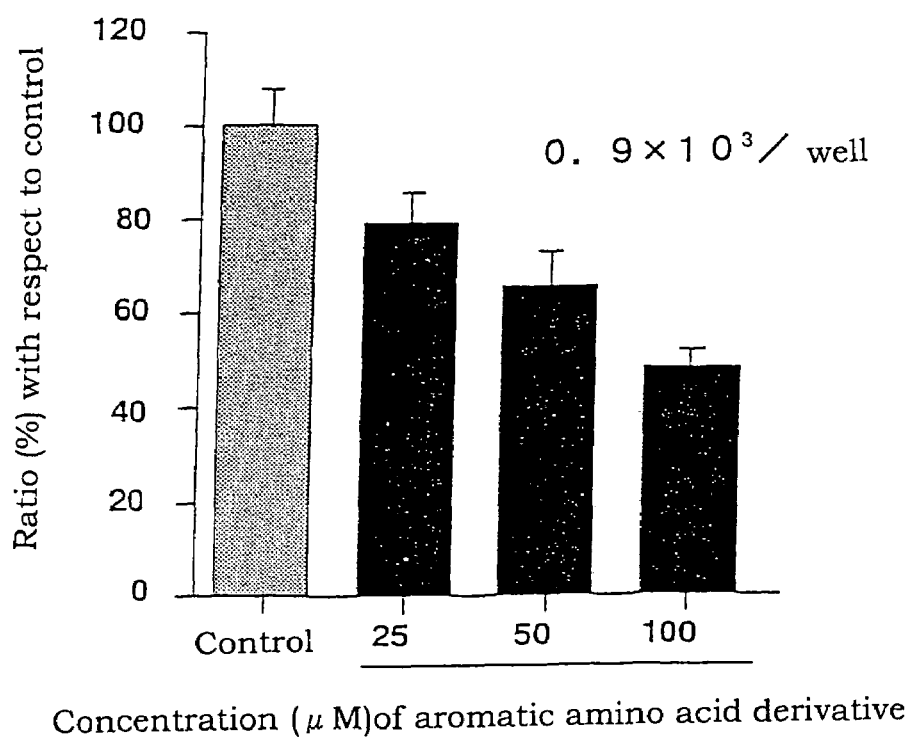
FIG. 4 is a graph showing activity inhibiting multiplication of cancer cells by further another aromatic amino acid derivative (Example 17) of the present invention.
Figure 5:
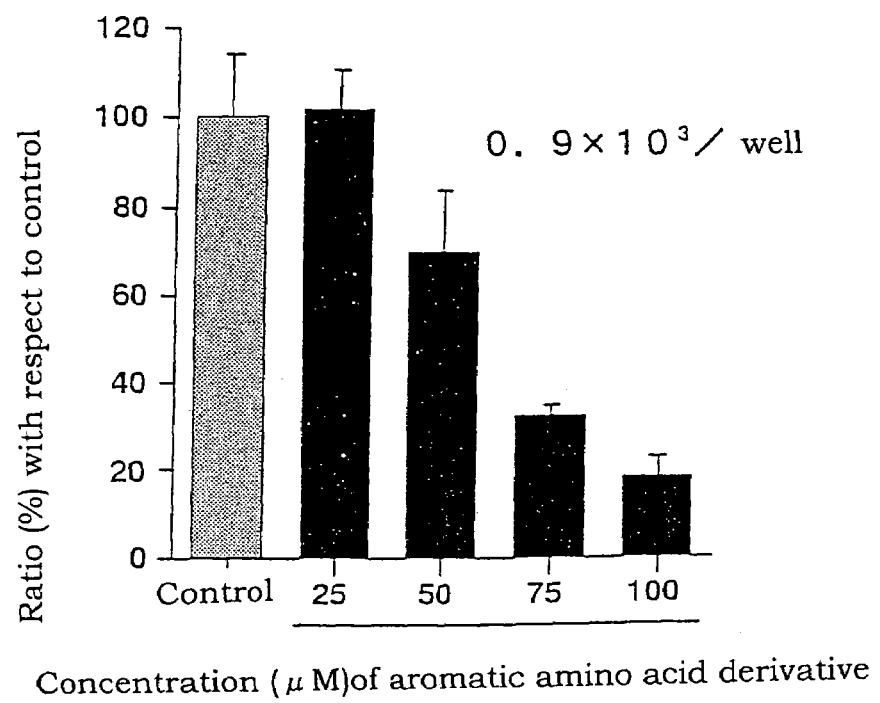
FIG. 5 is a graph showing activity inhibiting multiplication of cancer cells by further another aromatic amino acid derivative (Example 49) of the present invention.

In the compounds of the general formula (I) according to the present invention, the amino-protecting group for $R^1$ may be a group which can generally protect the amino group, and particularly an acyl group, for example, lower alkanoyl optionally substituted with alkoxycarbonyl, halogen, etc., cyclo(lower)alkyloxy(lower)alkanoyl, carboxy(lower)alkanoyl, lower alkylcarbamoyl, aroyl, arenesulfonyl, and the like can be exemplified.

As particularly preferable amino-protecting group, t-butoxycarbonyl, trifluoroacetyl, acetyl, etc. can be mentioned.

In the present specification, the term "lower" means a group having 1-6 carbon atoms unless otherwise provided.

As the alkyl group for $R^2$, lower alkyl group is preferable, and particularly methyl, ethyl, propyl, etc. can be mentioned.

As the aralkyl group, benzyl, phenethyl, etc. can be mentioned.

As the aryl group, phenyl, tolyl, xylyl, cumenyl, mesityl, naphthyl, biphenyl, etc. can be mentioned.

As the halogen atom for $R^3$ and X, fluorine, chlorine, bromine and iodine can be mentioned.

As the aroylamino group for $R^3$, benzoylamino, toluoylamino, naphthoylamino, etc. can be mentioned, among which benzoylamino is preferable. The amino moiety in the aroylamino group may be substituted with lower alkyl.

As the lower alkoxy for $R^3$, methoxy, ethoxy, propoxy, etc. can be mentioned.

As the lower alkoxycarbonyl, methoxycarbonyl, ethoxycarbonyl, propoxycarbonyl, etc. can be mentioned.

As the di(lower)alkylamino, dimethylamino, diethylamino, dipropylamino, etc. can be mentioned.

As the unsaturated mono-cyclic heterocyclic group containing N, O and/or S for $R^3$, furyl, thienyl, pyrrolyl, oxazolyl, isoxazolyl, thiazolyl, isothiazolyl, imidazolyl, pyrazolyl, furazanyl, pyridyl, pyridazinyl, pyrimidinyl, pyrazinyl, etc. can be mentioned, among which oxazolyl, isoxazolyl, thiazolyl, isothiazolyl, pyridyl, etc. are preferable.

As the cycloalkyl for $R^3$, cyclopropyl, cyclobutyl, cyclopentyl, cyclohexyl, etc. can be mentioned, among which cyclohexyl, etc. are preferable.

As the di(lower)alkylcarbamoyl, dimethylcarbamoyl, diethylcarbamoyl, dipropylcarbamoyl, etc. can be mentioned.

As the saturated, mono-cyclic heterocyclic group containing N, O and/or S for $R^3$, pyrrolidinyl, imidazolidinyl, pyrazolyl, pyradinyl, pyrazolidinyl, piperidinyl, piperadinyl, morpholinyl, piperidino, morpholino, etc. can be mentioned, among which piperidinyl, morpholinyl, piperidino, morpholino, etc. are preferable.

As the unsaturated or partially saturated condensed heterocyclic group containing N, O and/or S for $R^3$, indolyl, isoindolyl, benzofuranyl, indolidinyl, chromenyl, quinolyl, isoquinolyl, quinolidinyl, puryl, indazolyl, quinazolinyl, cinnolinyl, quinoxalinyl, phtharazinyl, benzoxazolyl, benzisoxazolyl, benzothiazolyl, benzisothiazolyl, benzimidazolyl, benzopyrazolyl, benzomorpholinyl, carbazolyl, xanthenyl, etc. can be mentioned, among which indolyl, benzofuryl, benzoxazolyl, purinyl, benzothiazolyl, chromenyl, quinolyl, benzomorpholinyl, etc. are preferable.

As the lower alkanoyloxy for $R^3$, acetoxy, propionyloxy, butyryloxy, etc. can be mentioned.

As the bis[halo(lower)alkyl]amino, bis[chloromethyl]amino, bis[chloroethyl]amino, bis[fluoromethyl]amino, bis[fluoroethyl]amino, etc. can be mentioned.

As the N-(lower)alkyl-N-hydroxy(lower) alkylamino, N-methyl-N-hydroxymethylamino, N-methyl-N-hydroxyethylamino, N-methyl-N-hydroxypropylamino, N-ethyl-N-hydroxymethylamino, N-ethyl-N-hydroxyetylamino, N-ethyl-N-hydroxy-propylamino, etc. can be mentioned.

Among the above compounds, preferred ones are compounds in which the unsaturated mono-cyclic heterocyclic group in the class ⑤ for R3 is 5-or 6-membered heterocyclic group containing N, N and O or N and S; compounds in which the saturated or unsaturated mono-cyclic heterocyclic group in the class ⑥ is 5-or 6-membered heterocyclic group containing N or N and O; and compounds in which the unsaturated or partially saturated condensed heterocyclic group in the class ⑥ is di-, tri- or tetra-cyclic condensed heterocyclic group containing N, O, N and O or N and S.

Particularly preferred compounds are those in which the unsaturated mono-cyclic heterocyclic group in the class ⑤ for $R^3$ is pyridyl, oxazolyl or thiazolyl; the saturated or unsaturated mono-cyclic heterocyclic group in the class ⑥ is piperidyl, pyrimidinyl, isoxazolyl, pyridyl or furyl; or the unsaturated or partially saturated condensed heterocyclic group in the class ⑥ is selected from the group consisting of:

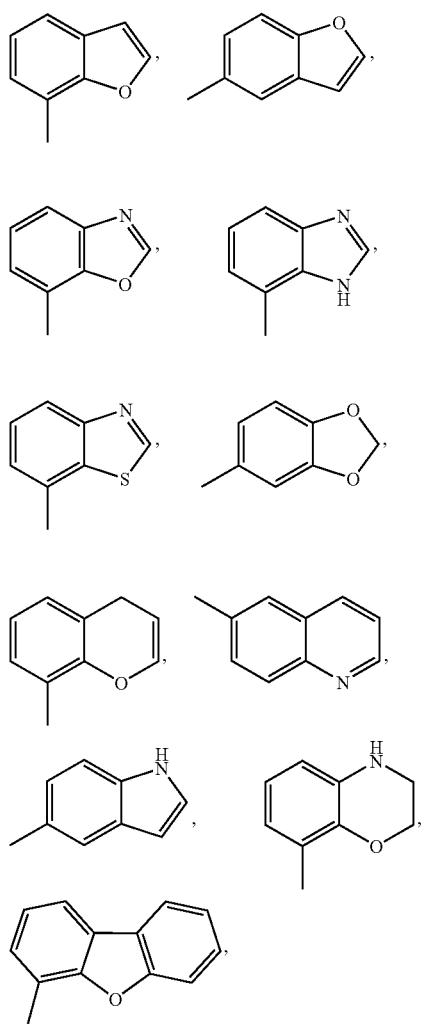

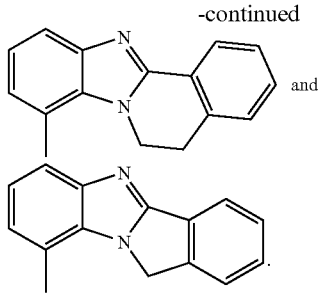

More preferable compounds are those in which $R^3$ is ③ phenyl group substituted with phenyl, phenoxy, pyridyl, pyrimidinyl or quinolyl, in which each substituent on the phenyl group may be further substituted with halogen atom, hydroxy or di(lower)alkylamino; ④ naphthyl group optionally substituted with hydroxy or lower alkoxy; ⑤ unsaturated mono-cyclic heterocyclic group containing N and O which is substituted with phenyl or naphthyl, in which each substituent on the mono-cyclic heterocyclic group may be further substituted with hydroxy; or ⑥ unsaturated or partially saturated condensed heterocyclic group containing N, O and/or S which may be substituted with oxo, amino, lower alkyl, di(lower)alkylamino, lower alkoxycarbonyl, di(lower)alkylcarbamoyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino or lower alkanoyloxy.

Further preferable compounds are those in which $R^3$ is ③ phenyl group substituted with phenyl or pyridyl each of which may be further substituted with halogen atom or di(lower)alkylamino; ④ naphthyl group optionally substituted with hydroxy or lower alkoxy; ⑥ unsaturated or partially saturated condensed heterocyclic group containing N, O and/or S, optionally substituted with oxo, lower alkyl, lower alkoxycarbonyl, phenyl or saturated or unsaturated mono-cyclic heterocyclic group containing N, O, and/or S, in which each substituent on the condensed heterocyclic group may be further substituted with halogen atom, hydroxy, lower alkyl, lower alkoxy, di(lower)alkylamino or lower alkanoyloxy.

Particularly preferable compounds are those which have ③ phenyl group substituted with pyridyl which is further substituted with di(lower)alkylamino; ④ naphthyl group; unsaturated mono-cyclic heterocyclic group substituted with naphthyl; ⑥ unsaturated or partially saturated condensed heterocyclic group containing N, O and/or S, optionally substituted with oxo, amino, lower alkyl, hydroxy(lower) alkyl, lower alkoxycarbonyl or phenyl.

Compounds where $R^3$ is ⑥ unsaturated or partially saturated condensed heterocyclic group containing N, O and/or S substituted with phenyl are also preferable.

Among the above compounds, preferable components are those in which $R^1$ is a hydrogen atom and/or the amino-protecting group is an acyl group and/or X is a halogen atom.

The compounds described in the following Table 1-13 are particularly exemplified as the compounds of formula (I).

TABLE 1
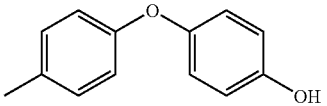
[ Intermediates in each Example:
R¹ = t-BuOCO, R² = CH₃ or
R¹ = CF₃CO, R² = CH₃ ]
| Ex. No. | n | X | R¹ | R² | R³ |
|---|---|---|---|---|---|
| 1 | 3 | I | H | H | Br |
| 2 | 1 | I | H | H | 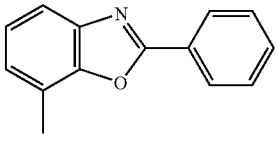 |
| 3 | 5 | I | H | H | Br |
| 4 | 2 | I | H | H | Br |
| 5 | 4 | I | H | H | Br |
| 6 | 1 | Cl | H | H | 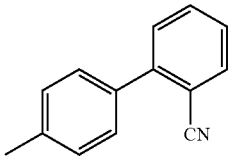 |
| 7 | 1 | Cl | H | H | 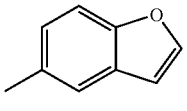 |
| 8 | 1 | Cl | H | H | 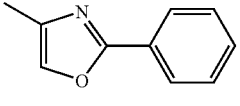 |
| 9 | 2 | Cl | H | H | 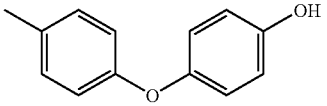 |
| 10 | 1 | Cl | H | H | 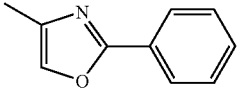 |
TABLE 2
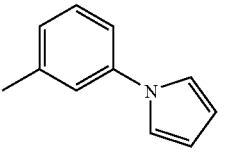
[ Intermediates in each Example:
R¹ = t-BuOCO, R² = CH₃ or
R¹ = CF₃CO, R² = CH₃ ]
| Ex. No. | n | X | R¹ | R² | R³ |
|---|---|---|---|---|---|
| 11 | 1 | Cl | H | H | 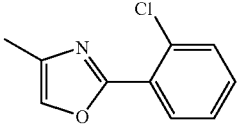 |
| 12 | 1 | Cl | H | H | 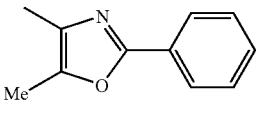 |
| 13 | 2 | Cl | H | H | 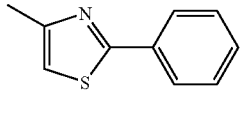 |
| 14 | 2 | Cl | H | H | 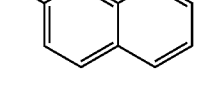 |
| 15 | 2 | Cl | H | H | 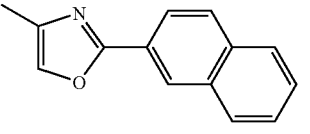 |
| 16 | 2 | Cl | H | H | (7-methylnaphthalene) |
| 17 | 2 | Cl | H | H | (4-methyl-2-(2-naphthyl)oxazole) |

TABLE 2-continued

Intermediates in each Example:
R¹ = t-BuOCO, R² = CH₃ or
R¹ = CF₃CO, R² = CH₃

| Ex. No. | n | X | R¹ | R² | R³ |
|---|---|---|---|---|---|
| 18 | 1 | Cl | H | H | 3-methylphenyl-O-(4-methoxyphenyl) |
| 19 | 1 | Cl | H | H | 4-methyl-2-phenylthiazole |

TABLE 3

Intermediates in each Example:
R¹ = t-BuOCO, R² = CH₃ or
R¹ = CF₃CO, R₂ = CH₃

| Ex. No. | n | X | R¹ | R² | R³ |
|---|---|---|---|---|---|
| 20 | 2 | Cl | H | H | 1-methylnaphthyl |
| 21 | 1 | Cl | H | H | 3-methylphenyl-O-(4-hydroxyphenyl) |
| 22 | 1 | Cl | H | H | 7-methyl-2-(4-hydroxyphenyl)benzoxazole |
| 23 | 2 | Cl | H | H | 7-methyl-2-phenylbenzoxazole |
| 24 | 1 | Cl | H | H | 4-methyldibenzofuran |
| 25 | 1 | Cl | H | H | 7-methyl-2-(4-methoxyphenyl)benzoxazole |
| 26 | 1 | Cl | H | H | 2-methyl-2'-methylbiphenyl |
| 27 | 1 | Cl | H | H | 2-methylbiphenyl |
| 28 | 1 | Cl | H | H | 7-methyl-2-(3-methoxyphenyl)benzoxazole |
| 29 | 1 | Cl | H | H | 2-methylbenzylbenzene |

TABLE 4

[Structure: benzene ring with X substituents, O-(CH₂)ₙ-R³ group, and CH₂-CH(NHR¹)-COOR² side chain]

[Intermediates in each Example:
R¹ = t-BuOCO, R² = CH₃ or
R¹ = CF₃CO, R² = CH₃]

| Ex. No. | n | X  | R¹ | R² | R³ |
|---------|---|----|----|----|-----|
| 30 | 1 | Cl | H | H | 7-methyl-benzoxazol-2-yl-(4-chlorophenyl) |
| 31 | 1 | Cl | H | H | 7-methyl-benzoxazol-2-yl-(3-chlorophenyl) |
| 32 | 1 | Cl | H | H | 7-methyl-benzoxazol-2-yl-(4-fluorophenyl) |
| 33 | 1 | Cl | H | H | 7-methyl-benzoxazol-2-yl-(pyridin-4-yl) |
| 34 | 1 | Cl | H | H | 7-methyl-benzoxazol-2-yl-(furan-2-yl) |
| 35 | 1 | Cl | H | H | 5,7-dimethyl-benzoxazol-2-yl-(4-methoxyphenyl) |
| 36 | 1 | Cl | H | H | 7-methyl-benzoxazol-2-yl-(4-methylphenyl) |
| 37 | 1 | Cl | H | H | 7-methyl-benzoxazol-2-yl-(4-dimethylaminophenyl) |
| 38 | 1 | Cl | H | H | 7-methyl-benzoxazol-2-yl-phenyl |

TABLE 4-continued

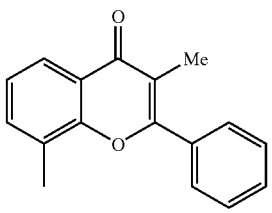

[ Intermediates in each Example:
$R^1$ = t-BuOCO, $R^2$ = $CH_3$ or
$R^1$ = $CF_3CO$, $R^2$ = $CH_3$ ]

| Ex. No. | n | X | $R^1$ | $R^2$ | $R^3$ |
|---|---|---|---|---|---|
| 39 | 1 | Cl | H | H | 3-methyl-8-methyl-2-phenyl-4H-chromen-4-one |

TABLE 5

[ Intermediates in each Example:
$R^1$ = t-BuOCO, $R^2$ = $CH_3$ or
$R^1$ = $CF_3CO$, $R^2$ = $CH_3$ ]

| Ex. No. | n | X | $R^1$ | $R^2$ | $R^3$ |
|---|---|---|---|---|---|
| 40 | 2 | Cl | H | H | 4-methyl-2-(3-hydroxyphenyl)oxazole |
| 41 | 3 | Cl | H | H | N-methylbenzamide |
| 42 | 3 | Cl | H | H | N,N-dimethylbenzamide (Me on N) |
| 43 | 1 | Cl | H | H | 7-methyl-2-{4-[bis(2-chloroethyl)amino]phenyl}benzoxazole |

TABLE 5-continued

[Structure: benzene ring with X substituents at 3,5 positions, O-(CH2)n-R³ at 4-position, and CH2-CH(NHR¹)-COOR² side chain]

[Intermediates in each Example: R¹ = t-BuOCO, R² = CH₃ or R¹ = CF₃CO, R² = CH₃]

| Ex. No. | n | X | R¹ | R² | R³ |
|---|---|---|---|---|---|
| 44 | 0 | Cl | H | H | 1-naphthyl |
| 45 | 0 | Cl | H | H | 6-hydroxy-2-naphthyl |
| 46 | 2 | Cl | H | H | 3-(4-hydroxyphenoxy)phenyl |
| 47 | 1 | Cl | H | H | 2-phenyl-7-benzofuranyl |
| 48 | 1 | Cl | H | H | 2-(3-hydroxyphenyl)-7-benzoxazolyl |

TABLE 6

[Structure: benzene ring with X at 4-position, O-(CH2)n-R³ at 3-position, and CH2-CH(NHR¹)-COOR² side chain]

[Intermediates in each Example: R¹ = t-BuOCO, R² = Et or R¹ = CF₃CO, R² = Et]

| Ex. No. | n | X | R¹ | R² | R³ |
|---|---|---|---|---|---|
| 49 | 0 | H | H | H | 2-naphthyl |
| 50 | 0 | H | H | H | 6-quinolinyl |
| 51 | 0 | H | H | H | 5-benzofuranyl |
| 52 | 0 | H | H | H | 5-indolyl |

TABLE 6-continued

Structure: aryl with X, $CH_2$-CH($NHR^1$)-$COOR^2$, O-$(CH_2)_n$-$R^3$

[Intermediates in each Example: $R^1$ = t-BuOCO, $R^2$ = Et or $R^1$ = CF$_3$CO, $R^2$ = Et]

| Ex. No. | n | X | R¹ | R² | R³ |
|---|---|---|---|---|---|
| 53 | 0 | H | H | H | biphenyl (3-) |
| 54 | 0 | H | H | H | 1-naphthyl |

TABLE 7

[Intermediates in each Example: $R^1$ = t-BuOCO, $R^2$ = Et or $R^1$ = CF$_3$CO, R2 = Et]

| Ex. No. | n | X | R¹ | R² | R³ |
|---|---|---|---|---|---|
| 55 | 0 | H | H | H | 6-methoxynaphth-2-yl |
| 56 | 0 | H | H | H | 6-hydroxynaphth-2-yl |
| 57 | 0 | H | H | H | 4-(4-hydroxyphenoxy)phenyl |
| 58 | 1 | H | H | H | naphth-2-yl |
| 59 | 2 | H | H | H | naphth-2-yl |
| 60 | 2 | H | H | H | 5,6,7,8-tetrahydronaphth-2-yl |

TABLE 8

[Intermediates in each Example: $R^1$ = t-BuOCO, $R^2$ = CH$_3$ or $R^1$ = CF$_3$CO, $R^2$ = CH$_3$]

| Ex. No. | n | X | R¹ | R² | R³ |
|---|---|---|---|---|---|
| 61 | 1 | Cl | H | H | 2-piperidino-benzothiazol-7-yl |
| 62 | 1 | Cl | H | H | 2-cyclohexyl-benzoxazol-7-yl |
| 63 | 1 | Cl | H | H | 2-benzyl-benzoxazol-7-yl |
| 64 | 1 | Cl | H | H | 2-phenyl-benzothiazol-7-yl |
| 65 | 1 | Cl | H | H | 2-(6-dimethylaminopyridin-3-yl)-benzoxazol-7-yl |
| 66 | 1 | Cl | H | H | benzimidazo-isoquinoline derivative |
| 67 | 1 | Cl | H | H | 3-(biphenyl-3-yl)pyridin-2-yl |
| 68 | 1 | Cl | H | H | 3-(naphth-2-yl)pyridin-2-yl |

TABLE 8-continued

![Structure: X-substituted phenyl with O(CH2)nR3 ether, R1NH-CH(COOR2)-CH2- chain]

[Intermediates in each Example:
R¹ = t-BuOCO, R² = CH₃ or
R¹ = CF₃CO, R² = CH₃]

| Ex. No. | n | X | R¹ | R² | R³ |
|---|---|---|---|---|---|
| 69 | 1 | Cl | H | H | (3-methyl-pyridin-2-yl)-tetrahydroisoquinoline |
| 70 | 1 | Cl | H | H | 7-methyl-benzoxazol-2-yl-(2-dimethylamino-pyrimidin-5-yl) |

TABLE 9

![Structure: X-substituted phenyl with O(CH2)nR3 ether, R1NH-CH(COOR2)-CH2- chain]

[Intermediates in each Example:
R¹ = t-BuOCO, R² = CH₃ or
R¹ = CF₃CO, R² = CH₃]

| Ex. No. | n | X | R¹ | R² | R³ |
|---|---|---|---|---|---|
| 71 | 1 | Cl | H | H | 8-methyl-2-phenyl-3,4-dihydro-2H-benzo[1,4]oxazine |
| 72 | 1 | Cl | H | H | 7-methyl-benzoxazol-2-yl-[2-(N-methyl-N-(2-hydroxyethyl)amino)-pyrimidin-5-yl] |
| 73 | 1 | Cl | H | H | methyl-benzimidazo-isoindole |
| 74 | 1 | Cl | H | H | 7-methyl-benzothiazol-2-yl-(2,4-dimethoxy-pyrimidin-5-yl) |
| 75 | 1 | Cl | H | H | 7-methyl-benzothiazol-2-yl-(3,5-dimethyl-isoxazol-4-yl) |
| 76 | 1 | Cl | H | H | (3-methyl-pyridin-2-yl)-4-biphenyl |
| 77 | 1 | Cl | H | Et | 8-methyl-3-methyl-2-phenyl-chromen-4-one (HCl) |
| 78 | 1 | Cl | H | Et | (3-methyl-pyridin-2-yl)-3-biphenyl (HCl) |
| 79 | 1 | Cl | H | Et | 7-methyl-benzothiazol-2-yl-piperidine (HCl) |
| 80 | 1 | Cl | H | H | 5-methoxy-7-methyl-2-phenyl-benzofuran |

TABLE 10

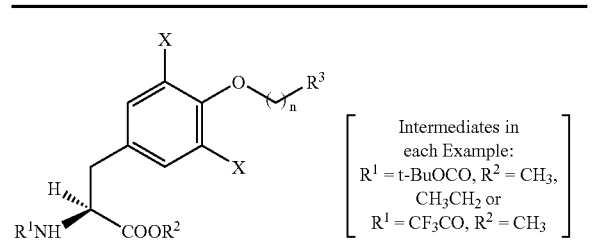

[Intermediates in each Example: R¹ = t-BuOCO, R² = CH₃, CH₃CH₂ or R¹ = CF₃CO, R² = CH₃]

| Ex. No. | n | X | R¹ | R² | R³ |
|---|---|---|---|---|---|
| 81 | 1 | Cl | H | H | 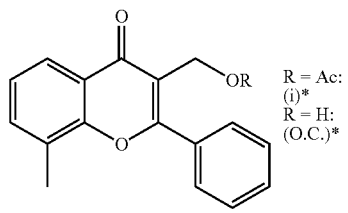 R = Ac: (i)* R = H: (O.C.)* |
| 82 | 1 | Cl | H | H | 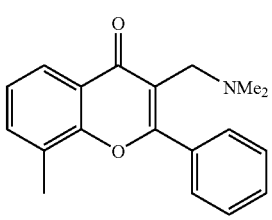 |
| 83 | 1 | Cl | H | H | 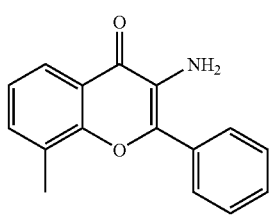 |
| 84 | 1 | Cl | H | H | 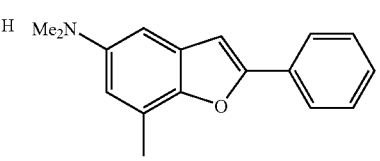 |
| 85 | 1 | Cl | H | H | 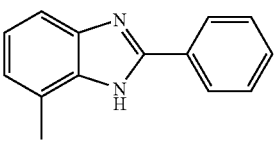 |
| 86 | 1 | Cl | H | H | 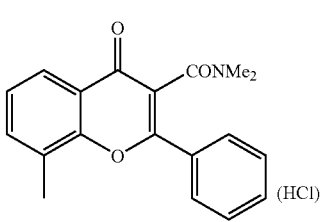 (HCl) |

TABLE 10-continued

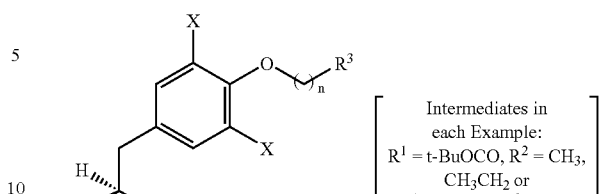

[Intermediates in each Example: R¹ = t-BuOCO, R² = CH₃, CH₃CH₂ or R¹ = CF₃CO, R² = CH₃]

| Ex. No. | n | X | R¹ | R² | R³ |
|---|---|---|---|---|---|
| 87 | 1 | Cl | H | H | 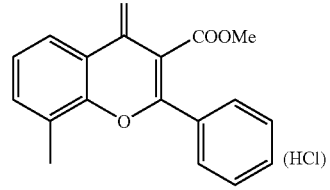 (HCl) |
| 88 | 1 | Cl | H | H | 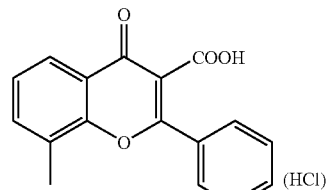 (HCl) |
| 89 | 1 | Cl | H | H | 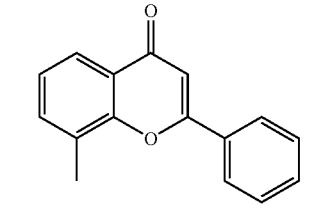 |
| 90 | 1 | Me | H | H | 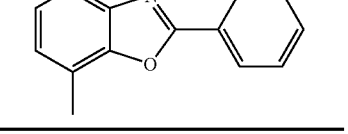 |

*(i) = intermediate, (o.c.) = object compound

TABLE 11

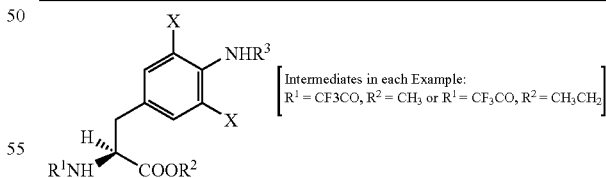

[Intermediates in each Example: R¹ = CF3CO, R² = CH₃ or R¹ = CF₃CO, R² = CH₃CH₂]

| Ex. No. | X | R¹ | R² | R³ |
|---|---|---|---|---|
| 91 | Cl | H | H | 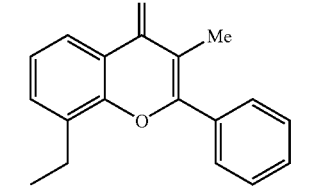 |

TABLE 11-continued

[Structure: benzene ring with X substituents at positions ortho to NHR³, CH₂ group to chiral carbon bearing H, NHR¹, and COOR²]

[Intermediates in each Example: R¹ = CF₃CO, R² = CH₃ or R¹ = CF₃CO, R² = CH₃CH₂]

| Ex. No. | X | R¹ | R² | R³ |
|---|---|---|---|---|
| 92 | Cl | H | Et | 3-methyl-8-ethyl-2-phenyl-4H-chromen-4-one (HCl) |

TABLE 12

[Structure: benzene ring with R³ substituent at meta position, CH₂ group to chiral carbon bearing H, NHR¹, and COOR²]

[Intermediates in each Example: R¹ = t-BuOCO, R² = Et or R¹ = CF₃CO, R² = Et]

| Ex. No. | R¹ | R² | R³ |
|---|---|---|---|
| 93 | H | H | 4-methoxybiphenyl |
| 94 | H | H | 6-methoxy-N,N-bis(2-hydroxyethyl)naphthalen-2-amine |
| 95 | H | H | 6-methoxy-N,N-bis(2-chloroethyl)naphthalen-2-amine |
| 96 | H | H | 4-(3-methoxyphenyl)pyridine |
| 97 | H | H | 5-(3-methoxyphenyl)-2-(dimethylamino)pyridine |
| 98 | H | H | 5-(3-methoxyphenyl)-2-(dimethylamino)pyridine (HCl) |
| 99 | H | H | 2-(3-methoxyphenyl)pyridine |
| 100 | H | H | 3-(3-methoxyphenyl)pyridine |
| 101 | H | H | 3'-methoxy-[1,1'-biphenyl]-4-carboxylate (R = Me: (i)*; R = H: (o.c.)*) |
| 102 | H | H | 3-chloro-3'-methoxybiphenyl |

*(i) = intermediate, (o.c.) = object compound

TABLE 13

[Intermediates in each Example: $R^1$ = t-BuOCO, $R^2$ = Et or $R^1$ = CF$_3$CO, $R^2$ = Et]

| Ex. No. | $R^1$ | $R^2$ | $R^3$ |
|---|---|---|---|
| 103 | H | H | 3-methoxy-4'-chlorobiphenyl |
| 104 | H | Et | 3-methoxy-4'-chlorobiphenyl (HCl) |
| 105 | H | H | 3-methoxy-4'-dimethylaminobiphenyl |
| 106 | H | H | 3-methoxyphenyl-quinoline |
| 107 | H | H | 3-methoxyphenyl-pyridine-thiomorpholine |
| 108 | H | H | 3-methoxyphenyl-pyrimidine-NMe$_2$ |
| 109 | H | H | 4-methoxyphenyl-pyrimidine-NMe$_2$ |
| 110 | H | H | 4-methoxyphenyl-pyridine-NMe$_2$ |
| 111 | H | H | naphthyl |
| 112 | H | H | biphenyl |

Among the above, the compounds obtained in Examples 6, 10, 17, 22, 23, 30, 32-40, 48, 49, 52-56, 58, 63, 65, 70-74, 81, 83, 85, 87, 89, 90, 91, 93, 96-100, 102, 103, 106, 108 and 112 are preferred.

Among the above, more preferable compounds are those obtained in Examples 6, 22, 30, 32-37, 39, 48, 49, 53, 55, 56, 70, 73, 81, 85, 87, 90, 91, 93, 97, 98, 100, 102 and 103.

Particularly, the compounds obtained in Examples 6, 17, 23, 39, 71, 73, 81, 83, 87, 89 and 91 are preferable, and the compounds obtained in Examples 6, 39, 73, 81, 87 and 91 are more preferable with respect to LAT2 selectivity.

The most preferable compounds are those obtained in Examples 6 and 49 from the view points of LAT2 selectivity and lower toxicity and side effect.

These compounds can be synthesized from starting materials commercially available or from compounds which can be obtained by the following Preparations or the methods similar thereto.

Those compounds can be prepared, for example, by a representative method shown in the following.

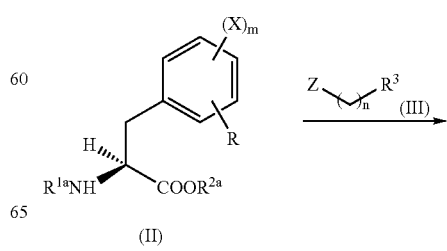

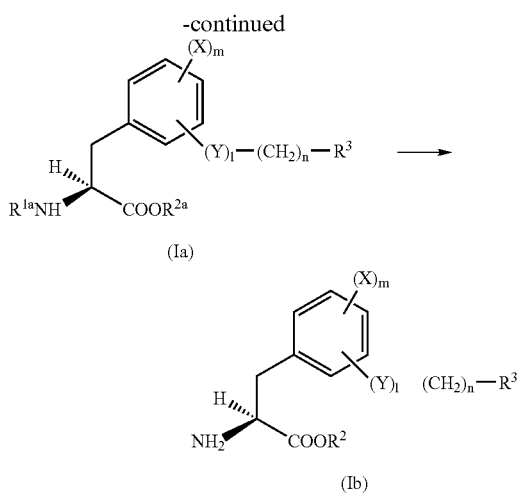

wherein, $R^{1a}$ is an amino-protecting group, e.g. acyl group such as t-butoxycarbonyl or trifluoroacetyl, etc., $R^{2a}$ is an alkyl, aralkyl or aryl group, R is hydroxy group, amino group or trifluoromethanesulfonyloxy group, $R^2$ is a hydrogen atom or an alkyl group, $R^3$ is a halogen atom, optionally substituted alkyl group, aryl group, heterocyclic group, condensed cyclic hydrocarbon residue or amino group, X is a hydrogen atom, a halogen atom, an alkyl group or an alkoxy group, l is 0 or 1, m is 1 or 2, n is an integer of 0-5, Y is an oxygen atom or a nitrogen atom optionally having a substituent, Z is a reactive group such as hydroxy group, a halogen atom or dihydroxyboryl group.

A compound of the formula (Ib) can be obtained by reacting a compound of the formula (II) with a compound of the formula (III) and then by removing the protecting group from the resultant compound of formula (Ia), if necessary.

The reaction of a compound of the formula (II) with a compound of the formula (III) may be carried out by one of the following methods and a compound of the formula (Ia) can be easily obtained:

(i) in the case where n is 1-5 and each of R and Z is hydroxy group, by condensation reaction carried out in an inert solvent such as tetrahydrofuran, dimethylformamide, etc., by using an azo compound such as diethyl azodicarboxylate or a phosphine compound such as triphenylphosphine as a condensing agent at reaction temperature of −30-25° C.;

(ii) in the case where n is 1-5, R is hydroxy or amino group and Z is a reactive group such as halogen atom, by reaction carried out in the presence or absence of a solvent such as dimethylformamide, acetone, in the presence or absence of a phase transfer catalyst such as tetra-n-butylammonium iodide, in the presence or absence of a base such as potassium carbonate, cesium carbonate, sodium hydride, at reaction temperature of 25-100° C.;

(iii) in the case where n is O, R is hydroxy group, Z is dihydroxyboryl group and $R^3$ is optionally substituted phenyl group or optionally substituted heterocyclic group, by arylating reaction carried out in a halogenic solvent such as dichloromethane, chloroform, 1,2-dichloroethane, in the presence of a base such as pyridine, triethylamine or a mixture thereof and of a molecular sieves 4A, by using copper (II) acetate, at reaction temperature of 25-60° C.;

(iv) in the case where n is 0, R is trifluoromethanesulfonyloxy group and Z is a reactive group such as dihydroxyboryl group, by a cross coupling reaction carried out in a solvent such as dimethoxyethane, dioxane, water or a mixture thereof, in the presence of a catalyst such as tetrakis(triphenylphosphine)palladium, by using a base such as potassium carbonate, sodium bicarbonate or tripotassium phosphate, at reaction temperature of 50-120° C., the compound of formula (Ia) can be easily obtained.

The substituent in the compound of the formula (Ia) may be optionally converted by a conventional method in the field of organic synthesis reaction (for example, in the case where $R^3$ in the formula (Ia) is an aryl group substituted with hydroxy group, by subjecting the compound to arylating reaction (or acylating reaction) using copper (II) acetate as in Example 57; or in the case where $R^3$ in the formula (Ia) is an amino group, by subjecting the compound to acylating reaction (or alkylating reaction) as in Examples 41 and 42; or in the case where $R^3$ is a hydroxy alkyl group, by converting it to halogen atom as in Example 43; or in the case where $R^3$ in the formula (Ia) is a halogen atom, by cross-coupling reaction of the aryl group or the heterocyclic group as in Examples 96-110), and then the protecting group may be removed.

The aromatic amino acid derivatives of the present invention can be in D-form or L-form due to existence of an asymmetric carbon atom.

The formula (I) and all of the other formulas in this specification unless otherwise provided include such stereoisomers and their mixture (for example, racemic mixture), among which the aromatic amino acid derivatives in the L-form is preferred.

The aromatic amino acid derivatives of the present invention may be in a form of a salt, and pharmacologically acceptable salts such as, for example, alkali metal salt (sodium salt, potassium salt, etc.), alkaline earth metal salt (calcium salt, magnesium salt, etc.), ammonium salt, salt with an organic base (trimethylamine, triethylamine, pyridine, picoline, dicyclohexylamine, dibenzylethylenediamine, etc.), salt with an organic acid (acetic acid, benzoic acid, succinic acid, fumaric acid, maleic acid, lactic acid, citric acid, tartaric acid, gluconic acid, methanesulfonic acid, benzenesulfonic acid, formic acid, p-toluenesulfonic acid, trifluoroacetic acid etc.), salt with an inorganic acid (hydrochloric acid, hydrobromic acid, sulfuric acid, phosphoric acid, etc.), and salt with an amino acid (arginine, aspartic acid, glutamic acid, etc.) can be mentioned as the salts.

These aromatic amino acid derivatives and their salts may be in a form of a hydrate or a solvate such as ethanolate.

The aromatic amino acid derivatives of the present invention is useful as an inhibitor of L-type amino acid transporter, or L-type amino acid transporter which can inhibit LAT1, both of LAT1 and LAT2 or LAT2.

The L-type amino acid transporter is useful as medical products in which various activities are expected, such as inhibitory activity of cancer cells proliferation, inhibitory activity of glucoavascularization associated with malignant tumor and vascularization associated with proliferation lesion of retina such as diabetic retinopacy, inhibitory activity of diseases associated with cells proliferation, for example various inflammatory disease, excessive granulation in an injury treatment process, controlling activity of absorption and internal distribution of poisonous substances transported by the transport system L, inhibitory activity of harmful effects caused by accentuation of amino acid metabolism in the cells, for example, hyperglycemia by accentuation of gluconeogenesis, skeletal muscular atrophy caused physiologically or in association with various diseases, and accentuated bone resorption.

The aromatic amino acid derivatives of the present invention can be administered by an oral or transdermal route or by injection.

Tablets, granules and capsules for oral administration may contain conventional additives, for example, a binding agent (e.g. syrup, gum arabic, gelatin, sorbitol, traganth or polyvinylpyrrolidone); filling agent (e.g. lactose, sugar, corn starch, calcium phosphate, sorbitol or glycine); lubricant (e.g. magnesium stearate, talc, polyethyleneglycol or silica); disintegrant (e.g. potato starch) or wetting agent (e.g. sodium lauryl sulfate). The tablets, granules and capsules may be coated by a known method in the field of conventional formulation.

Liquid preparation for oral administration may be in a form of aqueous or oily suspension, solution, emulsion, syrup or elixyl, or freezed-dry preparation which is dissolved in water or in a suitable solvent before use.

The liquid preparation may contain conventional additives, for example, suspending agent (e.g. sorbitol, syrup, methylcellulose, glucose syrup, gelatin hydrogenated edible fat; emulsifying agent (e.g. lecithin, sorbitan monooleate or gum arabic); hydrophobic excipient (e.g. almond oil, fractionated coconuts oil or glycerin, oily ester such as propyleneglycol or ethyl alcohol; preserving agent (e.g. methyl or propyl p-hydroxybenzoate or sorbic acid) and flavoring agent or coloring agent.

In the preparation for transdermal administration, the active ingredient may be in a form of cream, lotion or ointment. The cream or ointment preparation which can be used as a medicament can be prepared by a method well known in the art.

The preparation for injection can be prepared by suspending or dissolving a compound (I) or its salt in a proper medium. Adjuvants such as topical anesthetics, preserving agents and buffers may be contained in the preparation for injection.

Dosage of the compound (I) of the present invention and its salt may be properly controlled depending on various factors including activity of the compound (I), age, body weight, systemic healthy condition and sexuality of a patient, time of administration, administration route and severity of a disease.

For example, it is usually proper to administer about 10-5000 mg, preferably about 100-3000 mg per day for an adult, in 1-5 times.

The methods for preparing the aromatic amino acid derivatives (I) of the present invention are illustrated in detail in the following Preparations and Examples, and activity as an inhibitor of L-type amino acid transporter is explained in detail in the following Tests.

Preparation 1

1) A solution of 2-naphthoyl chloride (5.70 g, 29.9 mmol) in tetrahydrofuran (60 ml) was added dropwise to a mixture of 28% aqueous ammonia (20 ml) and tetrahydrofuran (30 ml) with stirring under ice cooling, and the mixture was stirred at room temperature for 4 hrs. The solvent was distilled off under reduced pressure, and water was added to the residue. The precipitates were collected by filtration and dried to give 2-carbamoylnaphthalene (2.68 g, 52%) as a colorless solid.

IR (Nujol): 3378, 3194, 1685, 1655 cm$^{-1}$; APCI-MS m/z: 172 [M+H]$^+$.

2) A mixture of 2-carbamoylnaphthalene (2.64 g, 15.4 mmol) and ethyl 4-chloroacetoacetate (2.06 g, 12.5 mmol) was stirred at 160° C. for 1 hr. and then diluted with ethyl acetate (200 ml) at room temperature. The solution was washed with saturated sodium bicarbonate aqueous solution and brine in turn, and then dried. The solvent was distilled off under reduced pressure, and the residue was purified by column chromatography on silica gel (n-hexane/ethyl acetate=8–4) to give ethyl ester of [2-(2-naphthyl)oxazol-4-yl]acetic acid(459 mg, 13%) as yellow crystals.

m.p.: 61.5-64° C.; IR (Nujol): 1737, 1591 cm$^{-1}$; $^1$H-NMR (CDCl$_3$): δ 1.31 (3H, t, J=7.1 Hz), 3.73 (2H, d, J=1.1 Hz), 4.24 (2H, q, J=7.1 Hz), 7.49-7.57 (2H, m), 7.76 (1H, t, J=1.1 Hz), 7.82-7.95 (3H, m), 8.11 (1H, dd, J=1.7, 8.7 Hz), 8.58 (1H, br d, J=1.1 Hz); APCI-MS m/z: 282 [M+H]$^+$.

3) A solution of ethyl ester of [2-(2-naphthyl)-oxazol-4-yl]acetic acid (434 mg, 1.54 mmol) in tetrahydrofuran (20 ml) was added dropwise to a suspension of lithium aluminium hydride (66 mg, 1.74 mmol) in tetrahydrofuran (15 ml) with stirring under ice cooling and the mixture was stirred at the same temperature for 2.5 hrs. To the reaction mixture were added water (0.1 ml), 15% aqueous solution of sodium hydroxide (0.1 ml), water (0.3 ml) and sodium sulfate (3 g )in turn. Insoluble materials were filtered off, and the solvent was distilled off under reduced pressure. The residue was purified by column chromatography on silica gel (n-hexane/ethyl acetate=2–1) to give 2-[2-(2-naphthyl)-oxazol-4-yl]ethanol (323 mg, 88%) as pale yellow crystals.

m.p.: 96-98° C.; IR (Nujol): 3466, 1591, 1543 cm$^{-1}$; $^1$H-NMR (CDCl$_3$): δ 2.85-2.90 (2H, m), 2.93 (1H, t, J=6.0 Hz), 3.99 (2H, q, J=6.0 Hz), 7.50-7.57 (2H, m), 7.58 (1H, t, J=1.0 Hz), 7.82-7.96 (3H, m), 8.10 (1H, dd, J=1.7, 8.6 Hz), 8.52 (1H, br); APCI-MS m/z: 240 [M+H]$^+$.

This compound was used as a starting material in Example 17. Oxazole derivatives used in Examples 9, 13 and 40 were synthesized according to this method.

Preparation 2

1) A mixture of isonicotinic acid chloride hydrochloride (2.34 g, 13.2 mmol), triethylamine (1.83 ml, 13.2 mmol) and tetrahydrofuran (10 ml) was added dropwise to a mixture of methyl ester of 3-amino-2-hydroxybenzoic acid hydrochloride (2.0 g, 12.0 mmol), N,N'-dimethylaniline (3.04 ml, 24.0 mmol) and tetrahydrofuran (20 ml) with stirring under ice cooling, and the mixture was stirred at the same temperature for 2 hrs. The reaction mixture was diluted with methylene chloride (200 ml), washed with water and brine in turn and then dried. The solvent was distilled off under reduced pressure, and the residue was purified by column chromatography on amine silica gel (Chromatolex (trademark) NH) (n-hexane/ethyl acetate=4 and chloroform/ethyl acetate=1) to give methyl ester of 2-hydroxy-3-isonicotinoylaminobenzoic acid (2.37 g, 73%) as pale yellow crystals.

m.p.: 157-158° C.; IR (Nujol): 3423, 1669, 1555, 1542 cm$^{-1}$; APCI-MS m/z: 273 [M+H]$^+$.

2) A mixture of methyl ester of 2-hydroxy-3-isonicotinoylamino-benzoic acid (500 mg, 1.84 mmol), p-toluenesulfonic acid mono-hydrate (349 mg, 1.84 mmol) and xylene (20 ml) was heated under reflux for 14 hrs. and then p-toluenesulfonic acid mono-hydrate (349 mg, 1.84 mmol) was further added and refluxed under heating for 2 hrs. The reaction mixture was cooled with ice, and ethyl acetate and 10% aqueous potassium carbonate solution were added thereto. The organic phase was separated, washed with water and brine in turn and then dried. The solvent was distilled off under reduced pressure, and the residue was triturated with a mixture of n-hexane/diisopropyl ether (4/1), filtered and dried to give methyl ester of [2-(4-pyridyl)-benzoxazol-7-yl]carboxylic acid (382 mg, 82%) as pale yellow crystals.

m.p.: 149-151° C.; IR (Nujol): 1725 cm$^{-1}$; APCI-MS m/z: 255 [M+H]$^+$.

3) Lithium aluminium hydride (53 mg, 1.42 mmol) was added to a solution of methyl ester of [2-(4-pyridyl)-benzoxazol-7-yl]carboxylic acid (360 mg, 1.42 mmol) in tetrahydrofuran (15 ml) with stirring under ice cooling in 10 min. and the mixture was stirred at the same temperature for 0.5 hrs. To the reaction mixture were added dropwise at the same temperature 10% aqueous tetrahydrofuran (2 ml) and 30% aqueous solution of sodium hydroxide (0.5 ml) in turn, and the mixture was stirred at room temperature for 2 hrs. The resultant insoluble materials were filtered off, and the solvent was distilled off from the filtrate under reduced pressure. The residue was diluted with ethyl acetate and washed with water and brine in turn and then dried. The solvent was distilled off under reduced pressure, and the resultant crystals were triturated with a mixture of n-hexane/diisopropyl ether (1/1), filtered and dried to give [2-(4-pyridyl)-benzoxazol-7-yl]methanol (216 mg, 67%) as colorless crystals.

m.p.: 146-147° C.; IR (Nujol): 3221, 1595, 1541 cm$^{-1}$; $^1$H-NMR (CDCl$_3$): δ 2.35 (1H, t, J=5.9 Hz), 5.08 (2H; d, J=5.9 Hz), 7.38-7.51 (2H, m), 7.76 (1H, dd, J=1.4, 7.8 Hz), 8.07-8.09 (2H, m), 8.78-8.81 (2H, m); APCI-MS m/z: 227 [M+H]$^+$.

This compound was used as a starting material in Example 33. Benzoxazole derivatives used in Examples 6, 22, 23, 25, 28, 30-38, 43, 62, 63 and 65 were synthesized according to this method.

Preparation 3

1) Triethylamine (7.1 ml, 51 mmol) was added dropwise at room temperature to a suspension of 3-hydroxybenzaldehyde (1.72 g, 14.1 mmol), 4-methoxyphenylboronic acid (3.16 g, 20.8 mmol), molecular sieves 4A powder (1.95 g) and copper (II) acetate (2.96 g, 16.3 mmol) in methylene chloride (100 ml), and the mixture was stirred for 27.5 hrs. The reaction mixture was diluted with ethyl acetate (200 ml), and the insoluble materials were filtered off and washed with ethyl acetate. The filtrate and washings were combined, washed with 10% hydrochloric acid and brine in turn and dried. The solvent was distilled off under reduced pressure, and the residue was purified by column chromatography on silica gel (n-hexane/ethyl acetate=7) to give 3-[(4-methoxy)phenoxy]benzaldehyde (596 mg, 19%) as a pale brown oil.

IR (Neat): 2835, 1699, 1584, 1504 cm$^{-1}$; GCEI-MS m/z: 228 (M$^+$).

2) Sodium borohydride (158 mg, 4.18 mmol) was added to a solution of 3-[(4-methoxy)phenoxy]benzaldehyde (573 mg, 2.51 mmol) in ethanol (10 ml) with stirring under ice cooling, and the mixture was stirred at room temperature for 25 min. The solvent was distilled off from the reaction mixture, and the residue was diluted with ethyl acetate, washed with water and brine in turn and dried. The solvent was distilled off and the residue was purified by column chromatography on silica gel (chloroform/ethyl acetate=20) to give 3-[(4-methoxy)phenoxy]benzyl alcohol (469 mg, 81%) as a colorless oil.

IR (Neat): 3356, 1611, 1586, 1504 cm$^{-1}$; $^1$H-NMR (CDCl$_3$): δ 1.67 (1H, t, J=5.3 Hz), 3.81 (3H, s), 4.65 (2H, br.d, J=4.6 Hz), 6.84-6.91 (3H, m), 6.93-7.06 (4H, m), 7.28 (1H, t, J=7.9 Hz); GCEI-MS m/z: 230 (M$^+$).

This compound was used as a starting material in Example 18.

Preparation 4

3-[(4-methoxy)phenoxy]benzyl alcohol obtained in Preparation 3 was subjected to demethylation reaction by a conventional method to give 3-[(4-hydroxy)phenoxy]benzyl alcohol as a pale yellow oil.

IR (Neat): 3350, 1603, 1585, 1505 cm$^{-1}$; $^1$H-NMR (CDCl$_3$+DMSO-d$_6$): δ 3.57 (1H, t, J=5.9 Hz), 4.60 (2H, d, J=5.5 Hz), 6.79-6.90 (5H, m), 6.92-6.96 (1H, m), 6.98-7.04 (1H, m), 7.24 (1H, t, J=7.8 Hz), 8.49 (1H, s); ESI-MS m/z: 215 [M−H]$^-$.

This compound was used as a starting material in Example 21.

Preparation 5

A solution of n-butyl lithium in hexane (1.5M; 8.9 ml, 13.4 mmol) was added dropwise to a solution of 2-bromo-6-methoxynaphthalene (3.0 g, 12.7 mmol) in tetrahydrofuran (45 ml) under argon atmosphere at −60° C. and the mixture was stirred at the same temperature for 70 min. To the mixture was added tri-n-butylborate (5.2 ml, 19.0 mmol) and the mixture was stirred at the same temperature for 1 hr. and then at 5° C. for 1.5 hrs. To the reaction mixture was added dropwise 20% hydrochloric acid (13 ml) at 5° C., and water was added thereto. The mixture was extracted with ethyl acetate. The organic layer was washed with water and brine in turn and dried. The solvent was distilled off under reduced pressure, and the residue was triturated with ethyl acetate and diethyl ether, filtered and dried to give (2-methoxy)-6-naphthalene boronic acid (1.50 g, 59%) as a colorless solid.

m.p.: 301-311° C.; IR (Nujol): 3290, 1625 cm$^{-1}$; $^1$H-NMR (DMSO-d$_6$): δ 3.87 (3H, s), 7.14 (1H, dd, J=2.6, 9.0 Hz), 7.28 (1H, d, J=2.6 Hz), 7.74 (1H, d, J=8.2 Hz), 7.79-7.84 (2H, m), 8.06(2H, s), 8.28 (1H, s).

This compound was used as a starting material in Example 45 and 55.

Preparation 6

A solution of boron tribromide in methylene chloride (1.0 M; 7 ml, 7 mmol) was added dropwise to a suspension of [2-(3-methoxyphenyl)-benzoxazol-7-yl]methanol (457 mg, 1.79 mmol) in methylene chloride (10 ml) at −78° C., and the mixture was stirred at the same temperature for 1 hr. After the removal of the cooling bath, the mixture was stirred at room temperature for 2.5 hrs. The reaction mixture was poured into ice-water (50 ml), and the organic layer was separated. The aqueous layer was extracted with ethyl acetate. The organic layers were combined and dried, and the solvent was distilled off under reduced pressure. The residue was purified by flash column chromatography on silica gel (n-hexane/ethyl acetate=3−1) to give 7-bromomethyl-2-(3-hydroxyphenyl)-benzoxazole (535 mg, 98%) as a brown solid.

m.p.: 225-228° C.; IR (Nujol): 3147, 1602, 1559 cm$^{-1}$; $^1$H-NMR (DMSO-d$_6$): δ 5.02 (2H, s), 7.04 (1H, ddd, J=0.9, 2.4, 8.0 Hz), 7.36-7.54 (3H, m), 7.62-7.71 (2H, m), 7.78 (1H, dd, J=1.2, 8.0 Hz), 10.0 (1H, s); APCI-MS m/z: 304/306 [M+H]$^+$.

This compound was used as a starting material in Example 48.

Preparation 7

A solution of n-butyl lithium in hexane (1.5M; 3.72 ml, 5.6 mmol) was added dropwise to a solution of 5-bromobenzo[b]furan (1.0 g, 5.0 mmol) in tetrahydrofuran (10 ml) under argon atmosphere at −60° C. and the mixture was stirred at the same temperature for 30 min. To the mixture was added trimethyl borate (0.69 ml, 6.0 mmol) and temperature of the mixture was raised to room temperature in 4 hrs. Water (5 ml) was added to the reaction mixture at 5° C. and tetrahydrofuran was distilled off under reduced pressure. To the residue was added 1N hydrochloric acid (pH 1) and the mixture was extracted with ethyl acetate. The organic layer was washed with brine and dried. The solvent was distilled off and the residue was triturated with a mixture of n-hexane/diethyl ether, filtered and dried to give 5-benzo[b]furan boronic acid (551 mg) as a pale brown solid.

This product was used as a starting material in Example 51 without purification. The boronic acid derivative used in Example 50 was synthesized according to this method.

Preparation 8

1) A mixture of ethyl ester of 2-bromobenzothiazole-7-carboxylic acid (572 mg, 2.00 mmol), piperidine (5 ml) and ethanol (1 ml) was stirred at 70-75° C. for 2.5 hrs. Diethyl ether (15 ml) was added to the mixture at room temperature and the precipitates were filtered off and washed with diethyl ether. The filtrate and washings were combined and the solvent was distilled off under reduced pressure. The residue was purified by column chromatography on silica gel (chloroform) to give ethyl ester of 2-piperidinobenzothiazole-7-carboxylic acid (526 mg, 90%) as pale orange crystals.

m.p.: 88-89° C.; IR (Nujol): 1791, 1595, 1541 cm$^{-1}$; APCI-MS m/z: 291 [M+H]$^+$ 2) Ethyl ester of 2-piperidinobenzothiazole-7-carboxylic acid (475 mg, 1.64 mmol) was reduced by using lithium aluminium hydride as in Preparation 2-3) to give 2-piperidinobenzothiazole-7-methanol (375 mg, 91%) as pale yellow crystals.

m.p.: 107-108° C.; IR (Nujol): 3261, 3200, 1595, 1541 cm$^{-1}$; APCI-MS m/z: 249 [M+H]$^+$.

This compound was used as a starting material in Example 61.

Preparation 9

1) Tetrakis(triphenylphosphine)palladium (144 mg, 0.125 mmol) and a solution of sodium bicarbonate (630 mg, 7.50 mmol) in degassed water (10 ml) were added in turn to a solution of ethyl ester of 2-bromobenzothiazole-7-carboxylic acid (715 mg, 2.50 mmol) and phenyl boronic acid (341 mg, 2.8 mmol) in degassed dimethoxyethane (20 ml) and the mixture was stirred at 50° C. for 10 min. Copper (I) iodide (24 mg, 0.125 mmol) was added to the mixture at room temperature and the mixture was heated under reflux for 4 hrs. Dimethoxyethane was distilled off under reduced pressure and the residue was extracted with ethyl acetate. The organic layer was washed with brine and dried and the solvent was distilled off under reduced pressure. The residue was purified by column chromatography on silica gel (n-hexane/ethyl acetate=10) to give ethyl ester of 2-phenylbenzothiazole-7-carboxylic acid (500 mg, 70%) as colorless crystals.

m.p.: 86.5-87.5° C.; IR (Nujol): 1716 cm$^{-1}$; APCI-MS m/z: 284 [M+H]$^+$.

2) Ethyl ester of 2-phenylbenzothiazole-7-carboxylic acid (425 mg, 1.50 mmol) was reduced by using lithium aluminium hydride as in Preparation 2-3) to give 2-phenylbenzothiazole-7-methanol (340 mg, 94%) as colorless crystals.

m.p.: 101-102° C.; IR (Nujol): 3241, 1572, 1507 cm$^{-1}$; APCI-MS m/z: 242 [M+H]$^+$.

This compound was used as a starting material in Example 64. The benzothiazole derivatives used in Examples 74 and 75 were synthesized according to this method.

Preparation 10

1) 2,6-Lutidine (1.83 ml, 15.7 mmol) and trifluoro-methanesulfonic anhydride (3.67 g, 13 mmol) were added dropwise in turn to a solution of methyl ester of 5-chloro-3-nitrosalicylic acid (2.32 g, 10.0 mmol) in methylene chloride (25 ml) with stirring under ice cooling and the mixture was stirred under ice cooling for 0.5 hrs. Methylene chloride (20 ml) and ice water (30 ml) were added to the reaction mixture and the aqueous layer was separated and extracted with methylene chloride. The organic layers were combined, washed with water and dried. The solvent was distilled off under reduced pressure and the residue was purified by column chromatography on silica gel (n-hexane/ethyl acetate=10) to give methyl ester of 5-chloro-2-trifluoromethanesulfonyloxy-3-nitrobenzoic acid (3.33 g, 91%) as a pale yellow oil.

IR (Neat): 3088, 2961, 1742, 1603, 1552 cm$^{-1}$; APCI-MS (m/z): 381 [M+NH$_4$]$^+$.

2) Triethylamine (0.33 ml, 2.37 mmol) and isoindoline (0.27 ml, 2.38 mmol) were added in turn to a solution of methyl ester of 5-chloro-2-trifluoromethanesulfonyloxy-3-nitrobenzoic acid (820 mg, 2.25 mmol) in dimethyl sulfoxide (5 ml) and the mixture was stirred at room temperature for 1 hr. The reaction mixture was cooled with ice and ice water (50 ml) was added thereto. The mixture was stirred and the precipitates were filtered, washed with water and dried. The resultant yellow crystals were purified by column chromatography on silica gel (n-hexane/ethyl acetate=15) to give methyl ester of 5-chloro-2-(1,2,3,4-tetrahydroisoquinolinio)-3-nitrobenzoic acid (608 mg, 81%) as yellow crystals.

m.p.: 114-115° C.; IR (Nujol): 1743, 1705, 1603, 1589, 1529, 1503 cm$^{-1}$; APCI-MS m/z: 333[M+H]$^+$.

3) 10% Palladium carbon (water 51.7%, 190 mg) was added to a solution of methyl ester of 5-chloro-2-(1,2,3,4-tetrahydroisoquinolinio)-3-nitrobenzoic acid (590 mg, 1.77 mmol) in methanol (6 ml) and tetrahydrofuran (9 ml) and, the mixture was stirred under hydrogen atmosphere at room temperature for 24 hrs. The catalyst was removed by filtration and the filtrate was concentrated to about 5 ml volume. The precipitating crystals were collected by filtration. To the crystals were added ethyl acetate (50 ml) and water (30 ml) and the mixture was adjusted to pH 8-9 by adding saturated sodium bicarbonate aqueous solution and extracted with ethyl acetate. The organic extract was washed with brine and dried. The solvent was distilled off under reduced pressure to give methyl ester of 1,2,3,4-tetrahydro-naphthalene[1,2-a]benzimidazole-7-carboxylic acid (96 mg, 20%) as pale yellow crystals.

m.p.: 152-153° C.; IR (Nujol): 1710, 1627, 1611, 1589, 1579, 1551 cm$^{-1}$; APCI-MS (m/z): 265[M+H]$^+$.

4) Methyl ester of 1,2,3,4-tetrahydronaphthalene[1,2-a]benzimidazole-7-carboxylic acid (80 mg, 0.30 mmol) was reduced by using lithium aluminium hydride as in Preparation 2-3) to give 1,2,3,4-tetrahydronaphthalene[1,2-a]benzimidazole-7-methanol (67 mg, crude 94%) as a pale grayish white solid. IR (Nujol): 3170, 1615, 1547 cm$^{-1}$; APCI-MS m/z: 237 [M+H]$^+$.

This compound was used as a starting material in Example 66. The benzimidazole derivative used in Example 73 was synthesized according to this method.

Preparation 11

1) 3-Biphenylphenylboronic acid (1089 mg, 5.50 mmol), tetrakis(triphenylphosphine)palladium (578 mg, 0.50 mmol) and potassium carbonate (2.07 g, 15.0 mmol) were added in turn to a solution of ethyl ester of 2-chloronicotinic acid (928 mg, 5.00 mmol) in degassed 1,4-dioxane (25 ml) and the mixture was heated under reflux for 18 hrs. Water was added to the mixture and the mixture was extracted with ethyl acetate. The organic layer was washed with water and brine in turn and dried. The solvent was distilled off under reduced pressure and the residue was purified by column chromatography on silica gel (n-hexane/ethyl acetate=5) to give ethyl ester of 2-(3-biphenyl)nicotinic acid (1.411 g, 93%) as a colorless oil.

IR (Neat): 2981, 1722, 1716 cm$^{-1}$; APCI-MS m/z: 304 [M+H]$^+$.

2) Ethyl ester of 2-(3-biphenyl)nicotinic acid (1.38 g, 4.55 mmol) was reduced by using lithium aluminium hydride as in Preparation 2-3) to give 2-(3-biphenyl)pyridine-3-methanol (1.115 g, 94%) as colorless crystals.

m.p: 91-93° C.; IR (Nujol): 3265, 1579, 1566 cm$^{-1}$; APCI-MS m/z: 262 [M+H]$^+$.

This compound was used as a starting material in Example 67. The pyridine derivatives used in Examples 68 and 76 were synthesized according to this method.

Preparation 12

1) 1,2,3,4-Tetrahydroisoquinoline (0,49 ml, 3.9 mmol) and triethylamine (0.47 ml, 3.34 mmol) were added in turn to a solution of ethyl ester of 2-chloronicotinic acid (557 mg, 3.0 mmol) in tetrahydrofuran (17 ml) and the mixture was heated under reflux for 18 hrs. After the mixture was cooled to room temperature, the precipitates were filtered off and the solvent of the filtrate was distilled off under reduced pressure. The residue was dissolved in ethyl acetate, washed with water and brine in turn and dried. The solvent was distilled off under reduced pressure and the residue was purified by column chromatography on amine silica gel (Chromatolex (trademark) NH) (n-hexane/ethyl acetate=19) to give ethyl ester of 2-(1,2,3,4-tetrahydroisoquinolinio)nicotinic acid (529 mg, 62%) as a colorless oil.

IR (Neat): 2979, 1711, 1584, 1555 cm$^{-1}$; APCI-MS m/z: 283 [M+H]$^+$.

2) Ethyl ester of 2-(1,2,3,4-tetrahydroisoquinolinio)nicotinic acid (511 mg, 1.81 mmol) was reduced by using lithium aluminium hydride as in Preparation 2-3) to give 2-(1,2,3,4-tetrahydroisoquinolinio)pyridine-3-methanol (386 mg, 89%) as colorless crystals.

m.p.: 95-97° C.; IR (Nujol): 3184, 1595, 1575 cm$^{-1}$; APCI-MS m/z: 241 [M+H]$^+$.

This compound was used as a starting material in Example 69.

Preparation 13

1) Methyl ester of 2-(2-methylthiopyrimidine-5-yl)benzoxazole-carboxylic acid was synthesized from 3-aminosalicylic acid hydrochloride and 2-methylthiopyrimidene-5-carboxylic acid chloride hydrochloride according to the method of Preparation 2.

m.p.: 190-191° C.; IR (Nujol): 1719 cm$^{-1}$; APCI-MS m/z: 302 [M+H]$^+$.

2) 77% m-Chloroperbenzoic acid (476 mg, 2.12 mmol) was added to a suspension of methyl ester of 2-(2-methylthiopyrimidin-5-yl)benzoxazole-7-carboxylic acid (400 mg, 1.33 mmol) in tetrahydrofuran (10 ml) under ice cooling and the mixture was stirred for 15 min. and then at room temperature for 3 hrs. To the reaction mixture was added dropwise 50% aqueous solution of dimethylamine at room temperature and the mixture was stirred at room temperature for 1 hr. The reaction mixture was cooled with ice and water (25 ml) was added thereto. The mixture was stirred for 15 min. and extracted with ethyl acetate. The organic layer was washed with water and brine in turn and dried. The solvent was distilled off under reduced pressure and the residue was purified by column chromatography on silica gel (chloroform/ethyl acetate=4) to give methyl ester of 2-(2-dimethylaminopyrimidin-5-yl)benzoxazole-7-carboxylic acid (328 mg, 83%) as colorless crystals.

m.p.: 199-201° C.; IR (Nujol): 1719, 1628, 1605 cm$^{-1}$; APCI-MS m/z: 299 [M+H]$^+$.

3) Methyl ester of 2-(2-dimethylaminopyrimidin-5-yl) benzoxazole-7-carboxylic acid (480 mg, 1.61 mmol) was reduced by using lithium aluminium hydride as in Preparation 2-3) to give 2-(2-dimethylamino-pyrimidin-5-yl)benzoxazole-7-methanol (234 mg, 54%) as yellow crystals.

m.p.: 212-215° C.; IR (Nujol): 3283, 1617 cm$^{-1}$; APCI-MS m/z: 271 [M+H]$^+$.

This compound was used as a starting material in Example 70.

Preparation 14

1) Methyl ester of 2-[2-[N-2-(hydroxy)ethyl-N-methyl] aminopyrimidin-5-yl]benzoxazole-7-carboxylic acid (322 mg, 74%) was synthesized from methyl ester of 2-(2-methylthiopyrimidin-5-yl)benzoxazole-7-carboxylic acid (400 mg, 1.33 mmol) according to the method of Preparation 13-2).

m.p.: 157-159° C.; IR (Nujol): 3529, 1713, 1626, 1601 cm$^{-1}$; APCI-MS m/z: 329 [M+H]$^+$.

2) A hydroxyl group of methyl ester of 2-[2-[N-2-(hydroxy)ethyl-N-methyl]aminopyrimidin-5-yl]benzoxazole-7-carboxylic acid (300 mg, 0.914 mmol) was tetrahydropyranylated by a conventional method to give methyl ester of 2-[2-[N-2-(tetrahydropyran-2-yloxy)ethyl-N-methyl]aminopyrimidin-5-yl]benzoxazole-7-carboxylic acid (286 mg, 69%) as colorless crystals.

m.p.: 126-128° C.; IR (Nujol): 1717, 1625, 1601 cm$^{-1}$; APCI-MS m/z: 413 [M+H]$^+$.

3) Methyl ester of 2-[2-[N-2-(tetrahydropyran-2-yloxy) ethyl-N-methyl]aminopyrimidin-5-yl]benzoxazole-7-carboxylic acid (275 mg, 0.667 mmol) was reduced by using lithium aluminium hydride as in Preparation 2-3) to give 2-[2-[N-2-(tetrahydropyran-2-yloxy)ethyl-N-methyl]aminopyrimidin-5-yl]benzoxazole-7-methanol (128 mg, 50%) as colorless crystals.

m.p.: 110-112° C.; IR (Nujol): 3287, 1622, 1603 cm$^{-1}$; APCI-MS m/z: 385 [M+H]$^+$.

This compound was used as a starting material in Example 72.

Preparation 15

1) Boron trifluoride ether complex (1.83 ml, 14.86 mmol) was added dropwise to a suspension of sodium borohydride (422 mg, 11.14 mmol) in tetrahydrofuran (30 ml) with stirring under ice cooling in 10 min. To this reaction mixture was added a solution of (±)-2-phenyl-1,4-benzoxazin-3-one-8-carboxylic acid (500 mg, 1.86 mmol) in tetrahydrofuran (6 ml) and the mixture was stirred at the same temperature for 5 min. and then at room temperature for 1.5 hrs. The reaction mixture was cooled with ice and water (20 ml) was added dropwise thereto. The mixture was neutralized with saturated sodium bicarbonate solution and then extracted with ethyl acetate. The extract was washed with water and brine in turn and dried. The solvent was distilled off under reduced pressure to give (±)-2-phenyl-1,4-benzoxazine-8-methanol (397 mg, 89%) as a pale orange oil.

IR (Neat): 3375, 1607 cm$^{-1}$.

2) Sodium carbonate (2.90 g, 27.35 mmol) was added to a solution of (±)-2-phenyl-1,4-benzoxazine-8-methanol (600 mg, 2.49 mmol) in diethyl ether (22 ml) with stirring under ice cooling. Trifluoroacetic anhydride (3.86 ml, 27.35 mmol) was added to the mixture and the mixture was stirred at the same temperature for 15 min. and at room temperature for 15 min. The reaction mixture was cooled with ice, poured into ice water and then extracted with ethyl acetate. The extract was washed with water and brine in turn and dried. The solvent was distilled off under reduced pressure. The residue was triturated with diisopropyl ether, filtered and dried to give (±)-4-trifluoroacetyl-8-trifluoro-acetoxymethyl-2-phenyl-1,4-benzoxazine (973 mg, 90%) as colorless crystals.

m.p.: 91-92° C.; IR (Nujol): 1781, 1705 cm$^{-1}$.

3) Glycine buffer (pH 10, 6.33 ml) was added dropwise to a solution of (±)-4-trifluoroacetyl-8-trifluoroacetoxymethyl-2-phenyl-1,4-benzoxazine (953 mg, 2.20 mmol) in methanol (19 ml) at room temperature and the mixture was stirred for 30 min. To the mixture was added water (70 ml) and the mixture was stirred at room temperature for 20 min. and then extracted with ethyl acetate. The extract was washed with water and brine in turn and dried. The solvent was distilled off under reduced pressure to give (±)-4-trifluoroacetyl-2-phenyl-1,4-benzoxazine-8-methanol (793 mg, quantitative yield) as a pale orange oil.

IR (Neat): 3400, 1704 cm$^{-1}$.

This compound was used as a starting material in Example 71.

Preparation 16

(5-Methoxy-2-phenyl)benzo[b]furan-7-carboxylic acid was reduced by using lithium aluminium hydride in a conventional manner to give (5-methoxy-2-phenyl) benzo[b]furan-7-methanol.

m.p.: 150-151° C.

This compound was used as a starting material in Example 80.

Preparation 17

Hydroxy group of 3-hydroxymethylflavone-8-carboxylic acid was acetylated by a conventional: method and then the carboxyl group was reduced to give 3-acetoxymethylflavone-8-methanol.

m.p.: 204-206° C.; IR (Nujol): 1739, 1616 cm$^{-1}$; ESI-MS m/z: 337 [M−H]$^-$.

This compound was used as a starting material in Example 81.

Preparation 18

Ethyl ester of 3-bromomethylflavone-8-carboxylic acid was reacted with dimethylamine in a conventional manner and the resultant product was reduced to give 3-dimethylaminomethylflavone-8-methanol.

m.p.: 149.5-150.5° C.; IR (Nujol): 3448, 1627 cm$^{-1}$; APCI-MS m/z: 310 [M+H]$^+$.

This compound was used as a starting material in Example 82.

Preparation 19

1) Hydroxy group of 3-acetoxymethylflavone-8-methanol synthesized in Preparation 17 was methoxymethylated by a conventional method and then the acetyl group was removed. The resultant alcohol was oxidized to give 8-methoxymethoxymethylflavone-3-carboxylic acid.

m.p.: 142-143° C.; IR (Nujol): 1731, 1621, 1606 cm$^{-1}$; ESI-MS m/z: 339 [M−H]$^-$.

2) 8-Methoxymethoxymethylflavone-3-carboxylic acid was reacted with diphenylphosphoryl azide and then with t-butanol. The resultant product was hydrolyzed with aqueous hydrochloric acid-dioxane to give 3-aminoflavone-8-methanol.

m.p.: 191.5-192.5° C.; IR (Nujol): 3391, 3302, 1606 cm$^{-1}$; APCI-MS m/z: 268 [M+H]$^+$.

This compound was used as a starting material in Example 83.

Preparation 20

Amino group of methyl ester of (5-amino-2-phenyl)benzo[b]furan-7-carboxylic acid was dimethylated by a conventional method and then the ester group was reduced by lithium aluminium hydride to give (5-dimethylamino-2-phenyl)benzo[b]furan-7-methanol.

m.p.: 115-116° C.; IR (Nujol): 3243, 1734, 1703 cm$^{-1}$; APCI-MS m/z: 268 [M+H]$^+$.

This compound was used as a starting material in Example 84.

Preparation 21

1) A mixture of methyl ester of 2-acetoamino-3-nitrobenzoic acid (1.444 g, 6.06 mmol) and 6N hydrochloric acid (30 ml) was heated under reflux for 15 min. The reaction mixture was cooled with ice, adjusted to pH 8 with 10% aqueous solution of potassium carbonate and then extracted with ethyl acetate. The extract was washed with water and brine in turn and dried. The solvent was distilled off under reduced pressure. The residue was purified by column chromatography on silica gel (n-hexane/ethyl acetate=1) to give methyl ester of 2-amino-3-nitrobenzoic acid (987 mg, 83%) as yellow crystals.

m.p.: 94-96° C.; APCI-MS m/z: 197 [M+H]$^+$.

2) 10% Palladium carbon (water content 51.7%, 250 mg) was added to a solution of methyl ester of 2-amino-3-nitrobenzoic acid (980 mg, 5.00 mmol) in methanol (20 ml)-tetrahydrofuran (10 ml) and the mixture was stirred under hydrogen atmosphere at room temperature for 3 hrs. The catalyst was removed by filtration and washed with tetrahydrofuran. The filtrate and washings were combined and the solvent was distilled off under reduced pressure to give methyl ester of 2,3-diaminobenzoic acid (814 mg, 98%) as a yellowish green solid.

m.p.: 65-67° C.; IR (Nujol): 3451, 3314, 1701, 1619 cm$^{-1}$; APCI-MS m/z: 167 [M+H]$^+$ 3) A solution of methyl ester of 2,3-diaminobenzoic acid (4.00 g, 24.07 mmol) and benzaldehyde (2.56 g, 24.07 mmol) in nitrobenzene (60 ml) was stirred at 155-160° C. for 3 hrs. After being cooled to room temperature, the reaction mixture was purified by column chromatography on silica gel (n-hexane/ethyl acetate=20 and 4) to give methyl ester of 2-phenylbenzimidazole-4-carboxylic acid (3.89 g, 64%) as a pale yellow crystals.

m.p.: 125-127° C.; IR (Nujol): 3364, 1709 cm$^{-1}$; APCI-MS m/z: 253 [M+H]$^+$.

4) To 60% sodium hydride (32 mg, 0.793 mmol) washed with n-hexane was added dropwise a solution of methyl ester of 2-phenylbenzimidazole-4-carboxylic acid (200 mg, 0.793 mmol) in DMF (1.2 ml) at room temperature. The mixture was stirred at room temperature for 1.5 hrs. and 2-(trimethylsilyl)ethoxymethyl chloride (0.15 ml, 0.841 mmol) was added dropwise thereto. The mixture was stirred at room temperature for 2 hrs., cooled with ice and then water was added thereto. The mixture was extracted with ethyl acetate and the extract was washed with water and brine in turn and dried. The solvent was distilled off under reduced pressure and the residue was purified by column chromatography on silica gel (n-hexane/ethyl acetate=7 and 2.5) to give methyl ester of 1-[2-(trimethylsilyl)ethoxymethyl]-2-phenylbenzimidazole-4 or 7-carboxylic acid (113 mg, 37%) and methyl ester of 1-[2-(trimethylsilyl)ethoxymethyl]-2-phenylbenzimidazole-4 or 7-carboxylic acid (133 mg, 44%) respectively in turn of the elution as a colorless oil. Physical data of the eluted compounds are shown in turn of the elution.

IR (Neat): 2952, 1722 cm$^{-1}$; APCI-MS m/z: 383 [M+H]$^+$.
IR (Neat): 2951, 1723 cm$^{-1}$; APCI-MS m/z: 383 [M+H]$^+$.

5) Methyl ester of 1-[2-(trimethylsilyl)ethoxymethyl]-2-phenylbenzimidazole-4 or 7-carboxylic acid (120 mg, 0.314 mmol) (compound eluted later) was reduced by using lithium aluminium hydride to give 1-[2-(trimethylsilyl)ethoxymethyl]-2-phenylbenzimidazole-4 or 7-methanol (94 mg, 85%) as colorless crystals.

m.p.: 96-100° C.; IR (Nujol): 3181 cm$^{-1}$; APCI-MS m/z: 355 [M+H]$^+$.

This compound was used as a starting material in Example 85.

Preparation 22

8-Methoxymethoxymethylflavone-3-carboxylic acid obtained in Preparation 19-1) was subjected to amidation by a conventional method and the methoxymethyl group was removed by using aqueous hydrochloric acid-methanol. The resultant product was treated with thionyl chloride to give 8-chloromethyl-3-dimethylcarbamoylflavone.

m.p.: 202-203° C.; IR (Nujol): 1638, 1630, 1616 cm$^{-1}$; APCI-MS m/z: 324 [M+H]$^+$.

This compound was used as a starting material in Example 86.

Preparation 23

8-Methoxymethoxymethylflavone-3-carboxylic acid obtained in Preparation 19-1) was subjected to methyl esterification by a conventional method and the methoxymethyl group was removed by using aqueous hydrochloric acid-methanol. The resultant product was treated with thionyl chloride to give 8-chloromethyl-3-methoxycarbonylflavone.

m.p.: 149.5-150.5° C.; IR (Nujol): 1732, 1637 cm$^{-1}$; APCI-MS m/z: 311 [M+H]$^+$.

This compound was used as a starting material in Example 87.

Preparation 24

Methoxymethyl group of 8-Methoxymethoxymethylflavone-3-carboxylic acid obtained in Preparation 19-1) was removed by a conventional method and the carboxy1 group was converted to diphenylmethyl ester. The resultant product was treated with thionyl chloride to give 8-chloromethyl-3-diphenylmethoxycarbonylflavone.

m.p.: 185.5-186° C.; IR (Nujol): 1731, 1629 cm$^{-1}$; ESI-MS m/z: 485 [M+Na]$^+$.

This compound was used as a starting material in Example 88.

Preparation 25

8-Hydroxymethyl-3-methylflavone was treated with thionyl chloride to give 8-chloromethyl-3-methylflavone.

m.p.: 112.5-113.5° C.; IR (Nujol): 1622, 1601 cm$^{-1}$; APCI-MS m/z: 285 [M+H]$^+$.

This compound was used as a starting material in Example 91.

Preparation 26

1) 2,6-Dibromonaphthalene (2.20 g, 7.70 mmol) was subjected to amination reaction using palladium catalyst to give 2-[bis-2-(benzyloxy)ethyl]amino-6-bromonaphthalene (2.29 g, 61%) as a yellow oil. IR (Neat): 1625, 1585 cm$^{-1}$; APCI-MS m/z: 490/492 [M+H]$^+$.

2) 2-[Bis-2-(benzyloxy)ethyl]amino-6-bromonaphthalene (205 mg, 0.42 mmol) was treated in the same manner as in Preparation 5 to give 2-[bis-2-(benzyloxy)ethyl]aminonaphthalene-6-boronic acid (124 mg, 65%) as a yellow oil. This product was used as a starting material in Example 94 without purification.

Preparation 27

1) 37% Aqueous formaldehyde (13.55 ml, 180.3 mmol) was added dropwise to a solution of 2-amino-5-bromopyridine (2.0 g, 11.56 mmol) in methanol (465 ml) at room temperature. To the mixture was added dropwise a solution of zinc chloride (3.94 g, 28.90 mmol) and sodium cyanoborohydride (3.63 g, 57.80 mmol) in methanol (155 ml) and the mixture was stirred at room temperature for 4 hrs. To the reaction mixture was added ice water (300 ml) at 5° C. and then methanol was distilled off under reduced pressure. The residue was extracted with ethyl acetate-tetrahydrofuran (1/1) and the extract was washed with water and brine in turn and dried. The solvent was distilled off under reduced pressure. The residue was purified by column chromatography on silica gel (n-hexane/ethyl acetate=24 and 5) to give 5-bromo-2-dimethylamino-pyridine (1.00 g, 43%) as colorless crystals.

m.p.: 39-41° C.; IR (Nujol): 1588 cm$^{-1}$; APCI-MS m/z: 201/203 [M+H]$^+$.

2) 5-Bromo-2-dimethylaminopyridine (402 mg, 2.00 mmol) was treated in a similar manner to that of Preparation 5 to give 2-dimethylaminopyridine-5-boronic acid (321 mg, crude 97%) as a pale brown powder. This product was used as a starting material in Examples 97 and 110 without purification.

Preparation 28

1) A mixture of 5-bromo-2-chloropyridine (600 mg, 3.12 mmol) and thiomorpholine (1.60 g, 15.59 mmol) was stirred at 100° C. for 16 hrs. Saturated sodium bicarbonate solution was added to the reaction mixture and the mixture was extracted with ethyl acetate. The extract was washed with water and brine in turn and dried. The solvent was distilled off under reduced pressure and the residue was purified by column chromatography on silica gel (n-hexane/ethyl acetate=50) to give 5-bromo-2-thiomorpholnopyridine (465 mg, 58%) as a colorless oil.

IR (Neat): 1581, 1481 cm$^{-1}$; APCI-MS m/z: 259/261 [M+H]$^+$.

2) Triethylamine (30 ml), bis(tributyltin) (3.05 ml, 6.04 mmol) and tetrakis(triphenylphosphine)palladium (315 mg, 0.272 mmol) were added in turn to a solution of 5-bromo-2-thiomorpholinopyridine (706 mg, 2.72 mmol) in degassed toluene (30 ml)-1,4-dioxane (30 ml) at room temperature, and the mixture was degassed and replaced with argon. The mixture was stirred at 95-100° C. for 14 hrs. After the mixture was cooled to room temperature, the solvent was distilled off under reduced pressure. The residue was purified by column chromatography on amine silica gel (Chromatolex (trademark) NH) (n-hexane/ethyl acetate=100) to give 5-tri-n-butyl-stannyl-2-thiomorpholinopyridine (467 mg, 37%) as a colorless oil.

IR (Neat): 1575, 1535, 1483 cm$^{-1}$; APCI-MS m/z: 467/469/471 [M+H]$^+$.

This compound was used as a starting material in Example 107.

Preparation 29

1) 50% Aqueous solution of dimethylamine (30 ml) was added to 5-bromo-2-chloropyridine (1.79 g, 10 mmol) and the mixture was stirred at room temperature under argon atmosphere for 5 hrs. Saturated sodium bicarbonate solution (15 ml) was added to the reaction mixture and the mixture was extracted with ethyl acetate. The extract was washed with brine and dried. The solvent was distilled off under reduced pressure and the residue was dried at 40° C. under reduced pressure for 2 hrs. to give 5-bromo-2-dimethylaminopyrimidine (1.83 g, 90%) as colorless crystals.

m.p.: 81-82° C.; IR (Nujol): 1586, 1527 cm$^{-1}$; APCI-MS m/z: 202/204 [M+H]

2) n-Butyl lithium (1.5 M n-hexane solution; 6.06 ml, 9.09 mmol) was added dropwise to a solution of 5-bromo-2-dimethylaminopyrimidine (1.75 g, 8.66 mmol) in tetrahydrofuran (18 ml) at −78° C. under argon atmosphere in 15 min. The mixture was stirred at the same temperature for 2 hrs. and then tri-n-butyltin chloride (2.5 ml) was added dropwise thereto. The mixture was stirred at the same temperature for 0.5 hrs. and then at room temperature for 1 hr. To the reaction mixture were added 10% aqueous potassium fluoride (50 ml) and ethyl acetate (50 ml) in turn and the mixture was stirred at room temperature for 0.5 hrs. The organic layer was separated and washed with water and brine in turn and dried. The solvent was distilled off under reduced pressure and the residue was purified by column chromatography on amine silica gel (Chromatolex (trademark) NH) (n-hexane) to give 5-tri-n-butylstannyl-2-dimethylaminopyrimidine (2.65 g, 74%) as a colorless oil.

IR (Neat): 2955, 2925, 2870, 2853, 1569, 1519 cm$^{-1}$; APCI-MS m/z: 410/412/414 [M+H]$^+$.

This compound was used as a starting material in Examples 108 and 109.

Preparation 30

Tris(dibenzylideneacetone)dipalladium (37 mg, 0.04 mmol) and triphenylphosphine (69 mg, 0.261 mmol) were added in turn to a solution of N-t-butoxycarbonyl-3,5-diiodo-L-tyrosine methyl ester (700 mg, 1.28 mmol) in degassed N-methylpyrrolidone (2.1 ml) under argon atmosphere and the mixture was stirred at 50° C. for 10 min. After the mixture was cooled to room temperature, copper (I) iodide (24 mg, 0.125 mmol) was added thereto. The reaction mixture was stirred at 50° C. for 10 min. After the mixture was cooled to room temperature, tetramethyltin (0.39 ml, 2.82 mmol) was added dropwise thereto and the mixture was stirred at 65° C. for 18 hrs. in a sealed tube. To the ice-cold reaction mixture were added water (10 ml) and saturated sodium fluoride aqueous solution in turn. The mixture was extracted with ethyl acetate. The extract was washed with water and brine in turn and dried. The solvent was distilled off under reduced pressure. The residue was purified by column chromatography on silica gel (n-hexane/ethyl acetate=5) to give N-t-butoxycarbonyl-3,5-dimethyl-L-tyrosine methyl ester (230 mg, 56%) as a brown oil.

IR (Neat): 3389, 1739, 1695 cm$^{-1}$; APCI-MS m/z: 324 [M+H]$^+$.

This compound was used as a starting material in Example 90.

Preparation 31

N-Chlorosuccinimide (9.79 g, 73.32 mmol) was added to a solution of 4-amino-N-trifluoroacetyl-L-phenylalanine ethyl ester (9.30 g, 30.6 mmol) in dimethylformamide (305 ml) and the mixture was stirred under argon atmosphere at 55° C. for 2.5 hrs. Ethyl acetate and water were added to the reaction mixture under ice cooling and the mixture was adjusted to pH8 with saturated sodium bicarbonate solution and extracted with ethyl acetate. The extract was washed with water and brine in turn and dried. The solvent was distilled off under reduced pressure and the residue was purified by column chromatography on silica gel (n-hexane/ethyl acetate=6) to give 4-amino-3,5-dichloro-N-trifluoroacetyl-L-phenylalanine ethyl ester (8.49 g, 74%) as colorless crystals.

m.p.: 124-125° C.; IR (Nujol): 3300, 1742, 1707 cm$^{-1}$; ESI-MS m/z: 371/373 [M−H]$^-$.

This compound was used as a starting material in Example 91.

The compounds obtained in the following Examples are shown in Tables 1-13. In the following Examples, physical data of intermediate are shown in column 1) and physical properties of object compounds are shown in column 2).

EXAMPLE 1

1) Diethylazodicarboxylate (197 μl, 1.25 mmol) was added dropwise to a solution of N-t-butoxycarbonyl-3,5-diiodo-L-tyrosine methyl ester (274 mg, 0.5 mmol), 3-bromo-1-propanol (76 mg, 0.55 mmol) and triphenylphosphine (328 mg, 1.25 mmol) in tetrahydrofuran (5 ml) under argon atmosphere at −15° C. and the mixture was stirred at the same temperature for 0.5 hrs., at 0-5° C. for 0.5 hrs., and then at room temperature for 23 hrs. The solvent of the reaction mixture was distilled off at room temperature under reduced pressure. The residue was purified by column chromatography on silica gel (n-hexane/ethyl acetate=9) to give O-(3-bromopropyl)-N-t-butoxycarbonyl-3,5-diiodo-L-tyrosine methyl ester (145 mg, 43%) as colorless crystals.

m.p.: 102-103° C.; IR (Nujol): 3345, 1751, 1722, 1684 cm$^{-1}$, APCI-MS m/z: 685 [M+NH$_4$]$^+$.

2) Trifluoroacetic acid (2 ml) was added to O-(3-bromopropyl)-N-t-butoxycarbonyl-3,5-diiodo-L-tyrosine methyl ester (131mg, 0.196 mmol) and the mixture was stirred at room temperature for 8 hrs. The solvent of the reaction mixture was distilled off under reduced pressure. The residue was dissolved in tetrahydrofuran (2 ml)-water (2 ml) and lithium hydroxide monohydrate (25 mg, 0.596 mmol) was added thereto with stirring under ice cooling. The mixture was stirred at the same temperature for 4.5 hrs. To the reaction mixture were added 1N hydrochloric acid (0.2 ml) and water (5 ml), and the mixture was stirred at room temperature for 30 min. The precipitates were collected by filtration, washed with water and dried under reduced pressure to give O-(3-bromopropyl)-3,5-diiodo-L-tyrosine(79 mg, 71%) as colorless crystals.

m.p.: 213-215° C. (dec.); IR (Nujol): 3385, 3272, 1603 cm$^{-1}$; $^1$H-NMR (DMSO-d$_6$+TFA+D$_2$O): δ 2.40 (2H, quintet, J=6.0Hz), 3.01 (1H, dd, J=6.0, 15 Hz), 3.09 (1H, dd, J=6.0, 15 Hz), 3.77 (2H, t, J=6.0 Hz), 4.02 (2H, t, J=6.0 Hz), 4.23 (1H, t, J=6.0 Hz), 7.76 (2H, s); ESI-MS m/z: 552 [M−H]$^-$. Elemental analysis for C$_{12}$H$_{14}$Br$_{12}$NO$_3$.0.6H$_2$O: Calculated: C, 25.25; H, 2.71; N, 2.48; Br, 14.15. Found: C, 25.27; H, 2.64; N, 2.57; Br, 14.41.

EXAMPLE 2

1) Diethylazodicarboxylate (40% toluene solution 0.55 ml) was added dropwise to a solution of N-trifluoroacetyl-3,5-diiodo-L-tyrosine methyl ester (272 mg, 0.5 mmol), 4-(4-hydroxyphenoxy)benzylalcohol (119 mg, 0.55 mmol) and triphenylphosphine (328 mg, 1.25 mmol) in tetrahydrofuran (5 ml) under argon atmosphere at −15° C., and the mixture was stirred at the same temperature for 1.5 hrs. The solvent of the reaction mixture was distilled off under reduced pressure. The residue was purified by column chromatography on silica gel (n-hexane/ethyl acetate=2) to give N-trifluoroacetyl-O-[4-(4-hydroxy-phenoxy)benzyl]-3,5-diiodo-L-tyrosine methyl ester (280 mg, 76%) as colorless crystals.

m.p.: 154-156° C. (dec.); IR (Nujol): 3395, 3285, 1725, 1702, 1607, 1557 cm$^{-1}$; $^1$H-NMR (CDCl$_3$): δ 3.06 (1H, dd, J=5.3, 14 Hz), 3.14 (1H, dd, J=5.8, 14 Hz), 3.83 (3H, s), 4.70 (1H,s), 4.81 (1H, m), 4.94 (2H, s), 6.79-6.87 (3H, m), 6.93-7.00 (4H, m), 7.52 (2H, s), 7.56-7.61 (2H, m); ESI-MS m/z: 740 [M–H]$^-$. Elemental analysis for C$_{25}$H$_{20}$F$_3$I$_2$NO$_6$: Calculated: C, 40.51; H, 2.72; N, 1.89; F, 7.69. Found: C, 40.69; H, 2.67; N, 1.96; F, 7.85.

2) Lithium hydroxide monohydrate (47 mg, 1.12 mmol) was added to a solution of N-trifluoroacetyl-O-[4-(4-hydroxy-phenoxy)benzyl]-3,5-diiodo-L-tyrosine methyl ester (235 mg, 0.317 mmol) in tetrahydrofuran (2 ml)-water (1 ml) under ice cooling and the mixture was reacted at room temperature for 7.5 hrs., and then at 0-5° C. for 16 hrs. The reaction mixture was diluted with water, adjusted to pH 4-5 under ice cooling with 1N hydrochloric acid (0.79 ml) and stirred at room temperature for 1.5 hrs. The precipitates were collected by filtration, washed with water and ethanol in turn and dried to give O-[4-(4-hydroxyphenoxy)benzyl]-3,5-diiodo-L-tyrosine (188 mg, 90%) as pale yellow crystals.

m.p.: 183-185° C. (dec.); IR (Nujol): 1608 cm$^{-1}$; $^1$H-NMR (DMSO-d$_6$+TFA+D$_2$O): δ 3.07 (1H, dd), 3.14 (1H, dd), 4.25 (1H, quasi-t), 4.92 (2H, s), 6.82-6.88 (2H, m), 6.92-7.01 (4H, m), 7.62 (2H,d, J=8.6 Hz), 7.82 (2H, s); ESI-MS m/z: 630 [M–H]$^-$. Elemental analysis for C$_{22}$H$_{19}$I$_2$NO$_5$.0.3C$_2$H$_5$OH.0.6H$_2$O: Calculated: C, 41.39; H, 3.38; N, 2.14; I, 38.70. Found: C, 41.43; H, 3.12; N, 2.16; I, 38.43.

EXAMPLE 3

According to the method of Example 2, an object compound was synthesized from N-trifluoroacetyl-3,5-diiodo-L-tyrosine methyl ester via the corresponding intermediate.

1) m.p.: 95-99° C.; IR (Nujol): 3250, 1738, 1705, 1563 cm$^{-1}$; ESI-MS m/z: 690 [M–H]$^-$. 2) m.p.: 180-182° C.; IR (Nujol): 3396, 1625, 1595 cm$^{-1}$; $^1$H-NMR (DMSO-d$_6$+TFA+D$_2$O): δ 1.61-1.72 (2H, m), 1.81-1.98 (4H, m),2.99 (1H, dd, J=7.2, 14 Hz), 3.08 (1H, dd, J=5.8, 14 Hz), 3.59 (2H,t, J=6.6 Hz), 3.90 (2H, t, J=6.0 Hz), 4.24 (1H, quasi-t), 7.75 (2H,s); ESI-MS m/z: 580 [M–H]$^-$. Elemental analysis for C$_{14}$H$_{18}$BrI$_2$NO$_3$.0.5H$_2$O: Calculated: C, 28.45; H, 3.24; N, 2.37; Br, 13.52; I, 42.94. Found: C, 28.59; H, 3.05; N, 2.36; Br, 13.53; I, 42.80.

EXAMPLE 4

According to the method of Example 2, an object compound was synthesized from N-trifluoroacetyl-3,5-diiodo-L-tyrosine methyl ester via the corresponding intermediate.

1) m.p.: 137-140° C.; IR (Nujol): 3289, 1737, 1700, 1559 cm$^{-1}$; ESI-MS m/z: 648 [M–H]$^-$. 2) m.p.: 216-218° C. (dec.); IR (Nujol): 3608, 3387, 3280, 1603 cm$^{-1}$; $^1$H-NMR (DMSO-d$_6$+TFA+D$_2$O): δ 2.99 (1H, dd, J=7.1, 14 Hz), 3.08 (1H, dd, J=6.0, 14 Hz), 3.88 (2H, t, J=5.5 Hz), 4.20-4.27 (3H, m), 7.76 (2H, s); ESI-MS m/z: 538 [M–H]$^-$. Elemental analysis for C$_{11}$H$_{12}$BrI$_2$NO$_3$.H$_2$O: Calculated: C, 23.68; H, 2.53; N, 2.51; Br, 14.32. Found: C, 23.98; H, 2.48; N, 2.72; Br, 14.11.

EXAMPLE 5

According to the method of Example 2, an object compound was synthesized from N-trifluoroacetyl-3,5-diiodo-L-tyrosine methyl ester via the corresponding intermediate.

1) m.p.: 91-94° C.; IR (Nujol): 3297, 1738, 1705, 1561 cm$^{-1}$; ESI-MS m/z: 676 [M–H]$^-$.

2) m.p.: 200-210° C. (dec.); IR (Nujol): 3400, 1596, 1531, 1508 cm$^{-1}$; $^1$H-NMR (DMSO-d$_6$+TFA+D$_2$O): δ 1.93-2.63 (2H, m), 2.07-2.17 (2H, m), 2.99 (1H, dd, J=7.0, 15 Hz), 3.07 (1H, dd, J=5.8, 15 Hz), 3.66 (2H,t, J=6.5 Hz), 3.93 (2H, t, J=5.8 Hz), 4.22 (1H, quasi-t), 7.75 (2H,s); ESI-MS m/z: 566 [M–H]$^-$. Elemental analysis for C$_{13}$H$_{16}$BrI$_2$NO$_3$: Calculated: C, 27.49; H, 2.84; N, 2.47; Br, 14.07; I, 44.69. Found: C, 27.59; H, 2.93; N, 2.37; Br, 13.64; I, 44.39.

EXAMPLE 6

1) Diethylazodicarboxylate (40% toluene solution 0.63 ml) was added dropwise to a solution of 3,5-dichloro-N-trifluoroacetyl-L-tyrosine methyl ester (252 mg, 0.7 mmol), [(2-phenyl)-benzoxazol-7-yl]methanol (193 mg, 0.857 mmol) and triphenylphosphine (374 mg, 1.43 mmol) in tetrahydrofuran (3 ml) under argon atmosphere at 5° C., and the mixture was stirred at the same temperature for 60 hrs. The solvent of the reaction mixture was distilled off under reduced pressure. The residue was purified by column chromatography on silica gel (n-hexane/ethyl acetate=4) to give 3,5-dichloro-N-trifluoroacetyl-O-[(2-phenyl)-benzoxazol-7-yl]methyl-L-tyrosine methyl ester (324 mg, 82%) as colorless crystals.

m.p.: 168-170° C.; IR (Nujol): 3308, 1741, 1703, 1555 cm$^{-1}$; ESI-MS m/z: 565 [M–H]$^-$.

2) 0.5 N Lithium hydroxide (4.5 ml, 2.25 mmol) was added to a solution of 3,5-dichloro-N-trifluoroacetyl-O-[(2-phenyl)-benzoxazol-7-yl]methyl-L-tyrosine methyl ester (246 mg, 0.434 mmol) in tetrahydrofuran (2 ml) at 5° C. and the mixture was reacted at 5° C. for 84 hrs. The reaction mixture was diluted with water, adjusted to pH 3-4 with 1N hydrochloric acid under ice cooling and allowed to stand at 5° C. The precipitates were collected by filtration, washed with water and then dried to give 3,5-dichloro-O-[(2-phenyl)-benzoxazol-7-yl]methyl-L-tyrosine (198 mg, 94%) as a colorless solid.

m.p.: 233-238° C. (dec.); IR (Nujol): 3431, 1615, 1553, 1317, 967, 871, 709 cm$^{-1}$; $^1$H-NMR (DMSO-d$_6$+TFA+D$_2$O): δ 3.03 (1H, dd, J=7.0, 14 Hz), 3.14 (1H, dd, J=6.0, 14 Hz), 4.29 (1H, br t, J=6.7 Hz), 5.42 (2H, s), 7.45 (2H, s), 7.43-7.50 (1H, m), 7.57 (1H, br d, J=6.6 Hz), 7.61-7.70 (3H, m), 7.86 (1H, dd, J=1.0, 8.0 Hz), 8.15-8.22 (2H, m); ESI-MS m/z: 455 [M–H]$^-$. Elemental analysis for C$_{23}$H$_{18}$Cl$_2$N$_2$O$_4$.1.5H$_2$O: Calculated: C, 57.04; H, 4.37; N, 5.78; Cl, 14.64. Found: C, 56.97; H, 4.32; N, 5.68; Cl, 14.56.

3) 3,5-Dichloro-O-[(2-phenyl)-benzoxazol-7-yl]methyl-L-tyrosine methyl ester hydrochloride was synthesized by a conventional method from 3,5-dichloro-O-[(2-phenyl)-benzoxazol-7-yl]methyl-L-tyrosine.

m.p.: 225-225.5° C. (dec.); IR (Nujol): 3480, 1755, 1619, 1548 cm$^{-1}$; $^1$H-NMR (DMSO-d$_6$): δ 3.06-3.20 (2H, m), 3.72 (3H, s), 4.37 (1H, t, J=6.7 Hz), 5.41 (2H, s), 7.45 (1H, t, J=7.7 Hz), 7.48 (2H, s), 7.54-7.59 (1H, m), 7.60-7.68 (3H, m), 7.85 (1H, dd, J=1.1, 7.9 Hz), 8.14-8.21 (2H, m), 8.67 (3H, br); APCI-MS m/z: 471 [M+H]$^+$.

Elemental analysis for C$_{24}$H$_{20}$Cl$_2$N$_2$O$_4$.HCl.0.2H$_2$O: Calculated: C, 56.37; H, 4.22; N, 5.48; Cl, 20.80. Found: C, 56.24; H, 4.05; N, 5.44; Cl, 20.98.

EXAMPLE 7

According to the method of Example 6, object compounds of the following Examples 7-39 were synthesized from 3,5-dichloro-N-trifluoroacetyl-L-tyrosine methyl ester via each corresponding intermediate.

1) m.p.: 159-161° C.; IR (Nujol):,3280, 2223, 1743, 1701, 1557 cm$^{-1}$; ESI-MS m/z: 549 [M−H]$^-$.

2) m.p.: 220-223° C. (dec.); IR (Nujol): 3372, 2223, 1664, 1634 cm$^{-1}$; $^1$H-NMR (DMSO-d$_6$+TFA+D$_2$O): δ 3.12 (1H, dd, J=7.1, 14 Hz), 3.21 (1H, dd, J=5.9, 14 Hz), 4.30 (1H, quasi-t), 5.10 (2H,s), 7.47 (2H, s), 7.59-7.75 (6H, m), 7.83 (1H, td, J=7.8, 1.4 Hz), 7.95 (1H, dd, J=1.0, 7.8 Hz); ESI-MS m/z: 439 [M−H]$^-$. Elemental analysis for C$_{23}$H$_{18}$Cl$_2$N$_2$O$_3$.0.8H$_2$O: Calculated: C, 60.62; H, 4.33; N, 6.15; Cl, 15.56. Found: C, 60.35; H, 4.25; N, 5.97; Cl, 15.95.

EXAMPLE 8

1) m.p.: 101-102° C.; IR (Nujol): 3290, 1738, 1705, 1564 cm$^{-1}$; ESI-MS m/z: 488 [M−H]$^-$.

2) m.p.: 215-217° C. (dec.); IR (Nujol): 1609 cm$^{-1}$; $^1$H-NMR (DMSO-d$_6$+TFA+D$_2$O): δ 3.11 (1H, dd, J=7.2, 14 Hz), 3.19 (1H, dd, J=5.9, 14 Hz), 4.28 (1H, quasi-t), 5.11 (2H, s), 7.00 (1H, m), 7.44 (2H, s), 7.53 (1H, dd, J=1.7, 8.4 Hz), 7.64 (1H, d, J=8.4 Hz), 7.84 (1H, br d), 7.99 (1H, d, J=2.2 Hz); ESI-MS m/z: 378 [M−H]$^-$. Elemental analysis for C$_{18}$H$_{15}$Cl$_2$NO$_2$: Calculated: C, 56.86; H, 3.98; N, 3.68; Cl, 18.65. Found: C, 56.77; H, 3.91; N, 3.65; Cl, 18.63.

EXAMPLE 9

1) m.p.: 112-115° C.; IR (Nujol): 3263, 1747, 1705, 1554 cm$^{-1}$; ESI-MS m/z: 529 [M−H]$^-$.

2) m.p.: 198-205° C. (dec.); IR (Nujol): 3400, 1587, 1555, 1279, 1007, 879, 800, 779, 713 cm$^{-1}$; $^1$H-NMR (DMSO-d$_6$+TFA+D$_2$O): δ 2.99-3.19 (4H, m), 4.25-4.32 (3H, m),7.40 (2H, s), 7.50-7.57 (3H, m), 7.94-8.01 (2H, m), 8.05 (1H, br s); ESI-MS m/z: 443 [M+Na]$^+$. Elemental analysis for C$_{20}$H$_{18}$Cl$_2$N$_2$O$_4$.H$_2$O: Calculated: C, 54.68; H, 4.59; N, 6.38; Cl, 16.14. Found: C, 54.80; H, 4.60; N, 6.49; Cl, 16.24.

EXAMPLE 10

1) m.p.: 124-125° C.; IR (Nujol): 3470, 3299, 1737, 1706, 1610, 1558, 1503 cm$^{-1}$; ESI-MS m/z: 556 [M−H]$^-$.

2) m.p.: 214-215° C. (dec.); IR (Nujol): 3410, 3360, 1613 cm$^{-1}$; $^1$H-NMR (DMSO-d$_6$+TFA+D$_2$O): δ 3.07 (1H, dd, J=7.3, 14 Hz), 3.17 (1H, dd, J=6.0, 14 Hz), 4.28 (1H, quasi-t), 4.94 (2H, s), 6.80-6.85 (2H, m), 6.89-6.97 (4H, m), 7.43 (2H, s), 7.47-7.52 (2H, m); ESI-MS m/z: 446 [M−H]$^-$. Elemental analysis for C$_{22}$H$_{19}$Cl$_2$NO$_5$.0.15H$_2$O: Calculated: C, 58.59; H, 4.31; N, 3.11; Cl, 15.72. Found: C, 58.59; H, 4.21; N, 3.08; Cl, 15.65.

EXAMPLE 11

1) m.p.: 119-122° C.; IR (Nujol): 3300, 3129, 1747, 1701, 1554 cm$^{-1}$; ESI-MS m/z: 515 [M−H]$^-$.

2) m.p.: 212-218° C. (dec.); IR (Nujol): 3395, 1601, 1584, 1280, 1017, 778, 711 cm$^{-1}$; $^1$H-NMR (DMSO-d$_6$+TFA+D$_2$O): δ 3.06 (1H, dd, J=7.3, 14 Hz), 3.17 (1H, dd, J=5.9, 14 Hz), 4.29 (1H, t, J=6.4 Hz), 5.04 (2H, s), 7.43 (2H, s), 7.54-7.60 (3H, m), 7.96-8.05 (2H, m), 8.27 (1H, s); ESI-MS m/z: 405 [M−H]$^-$. Elemental analysis for C$_{19}$H$_{16}$Cl$_2$N$_2$O$_4$.H$_2$O: Calculated: C, 53.66; H, 4.27; N, 6.59; Cl, 16.67. Found: C, 53.43; H, 4.01; NY 6.35; Cl, 16.68.

EXAMPLE 12

1) m.p.: 105-107° C.; IR (Nujol): 3270, 1743, 1705, 1555, 1505 cm$^{-1}$; ESI-MS m/z: 513 [M−H]$^-$.

2) m.p.: 231-233.5° C. (dec.); IR (Nujol): 3020, 1627, 1593, 1528, 1502, 1404, 1322, 1269, 877, 719 cm$^{-1}$; $^1$H-NMR (DMSO-d$_6$+TFA+D$_2$O): δ 3.09 (1H, dd, J=7.1, 15 Hz), 3.18 (1H, dd, J=6.0, 15 Hz), 4.27 (1H, t, J=6.8 Hz), 5.09 (2H, s), 6.32 (2H, t, J=2.2 Hz), 7.35 (2H, t, J=2.2 Hz), 7.41-7.46 (3H, m), 7.50-7.61 (2H, m), 7.68 (1H, br s); ESI-MS m/z: 403 [M−H]$^-$. Elemental analysis for C$_{20}$H$_{18}$Cl$_2$N$_2$O$_3$: Calculated: C, 59.27; H, 4.48; N, 6.91; Cl, 17.50. Found: C, 59.08; H, 4.28; N, 6.75; Cl, 17.52.

EXAMPLE 13

1) m.p.: 97-99.5° C.; IR (Nujol): 3264, 1737, 1703, 1557 cm$^{-1}$; ESI-MS m/z: 563 [M−H]$^-$.

2) m.p.: 221-224° C. (dec.); IR (Nujol): 3060, 1625, 1590, 1512, 1404, 1265, 1034, 1003, 875, 803, 777, 737 cm$^{-1}$; $^1$H-NMR (DMSO-d$_6$+TFA+D$_2$O): δ 2.99-3.19 (4H, m), 4.23-4.33 (3H, m),7.39 (2H, s), 7.48-7.59 (2H, m), 7.62-7.67 (1H, m), 7.90-7.95 (1H, m), 8.13 (1H, s); ESI-MS m/z: 455 [M−H]$^-$. Elemental analysis for C$_{20}$H$_{17}$Cl$_3$N$_2$O$_4$: Calculated: C, 52.71; H, 3.76; N, 6.15; Cl, 23.34. Found: C, 52.45; H, 3.58; N, 6.26; Cl, 23.05.

EXAMPLE 14

1) m.p.: 138-140° C.; IR (Nujol): 3271, 1743, 1704 cm$^{-1}$; ESI-MS m/z: 543 [M−H]$^-$.

2) m.p.: 202-206° C. (dec.); IR (Nujol): 3499, 3396, 1641, 1604, 1583 cm$^{-1}$; $^1$H-NMR (DMSO-d$_6$+TFA+D$_2$O): δ 2.38 (3H, s), 2.96-3.18 (4H, m), 4.22-4.29 (3H, m), 7.37 (2H,s), 7.48-7.56 (3H, m), 7.89-7.94 (2H, m); ESI-MS m/z: 433 [M−H]$^-$. Elemental analysis for C$_{21}$H$_{20}$Cl$_2$N$_2$O$_4$.1.2H$_2$O: Calculated: C, 55.20; H, 4.92; N, 6.16; Cl, 15.52. Found: C, 55.07; H, 4.75; N, 6.15; Cl, 15.69.

EXAMPLE 15

1) m.p.: 123-124° C.; IR (Nujol): 3271, 1740, 1705 cm$^{-1}$; ESI-MS m/z: 545 [M−H]$^-$.

2) m.p.: 205-210° C. (dec.); IR (Nujol): 3396, 1587 cm$^{-1}$; $^1$H-NMR (DMSO-d$_6$+TFA+D$_2$O): δ 3.03 (1H, dd, J=7.3, 14 Hz), 3.13 (1H, dd, J=6.0, 14 Hz), 4.22-4.33 (3H, m), 7.37 (2H, s), 7.48-7.53 (4H,m), 7.88-7.96 (2H, m); ESI-MS m/z: 435 [M−H]$^-$. Elemental analysis for C$_{20}$H$_{18}$Cl$_2$N$_2$O$_3$S.H$_2$O: Calculated: C, 52.75; H, 4.43; N,6.15; Cl, 15.57; S, 7.04. Found: C, 52.56; H, 4.39; N, 6.07; Cl, 15.42; S, 6.88.

EXAMPLE 16

1) m.p.: 112-113° C.; IR (Nujol): 3297, 1757, 1701 cm$^{-1}$; APCI-MS m/z: 514 [M+H]$^+$.

2) m.p.: 228-231° C. (dec.); IR (Nujol): 3406, 1593 cm$^{-1}$; $^1$H-NMR (DMSO-d$_6$+TFA+D$_2$O): δ 3.03 (1H, dd, J=7.3, 14 Hz), 3.14 (1H, dd, J=6.0, 14 Hz), 3.28 (2H, t, J=6.6 Hz), 4.22-4.34 (3H, m), 7.37 (2H, s), 7.47-7.54.(3H, m), 7.83-7.92 (4H, m); ESI-MS m/z: 402 [M−H]$^-$. Elemental analysis for C$_{21}$H$_{19}$Cl$_2$NO$_3$.H$_2$O: Calculated: C, 59.73; H, 5.01; N, 3.32; Cl, 16.79. Found: C, 59.67; H, 4.82; N, 3.21; Cl, 16.76.

EXAMPLE 17

1) m.p.: 144-147° C.; IR (Nujol): 3295, 1751, 1698, 1553 cm$^{-1}$; ESI-MS m/z: 579 [M−H]$^-$.

2) m.p.: 232-233° C. (dec.); IR (Nujol): 3380, 1630, 1586, 1405, 1265, 1193, 1003, 878, 800, 754, 741 cm$^{-1}$; $^1$H-NMR (DMSO-d$_6$+TFA+D$_2$O): δ 3.04 (1H, dd, J=7.3, 14 Hz), 3.04-3.20 (3H, m), 4.22-4.44 (3H, m), 7.39 (2H, s), 7.58-

7.66 (2H, m), 7.96-8.03 (1H, m), 8.05-8.14 (4H, m), 8.55 (1H, br s); ESI-MS m/z: 469 [M−H]⁻. Elemental analysis for C$_{24}$H$_{20}$Cl$_2$N$_2$O$_4$.0.9H$_2$O: Calculated: C, 59.12; H, 4.51; N, 5.75; Cl, 14.54. Found: C, 59.22; H, 4.29; N, 5.72; Cl, 14.41.

EXAMPLE 18

1) m.p.: 88-92° C.; IR (Nujol): 3295, 1758, 1701, 1558, 1505 cm⁻¹; ESI-MS m/z: 570 [M−H]⁻.

2) m.p.: 230-233° C. (dec.); IR (Nujol): 3060, 1625, 1589, 1505, 1403, 1319, 1264, 1248, 1210, 1037, 939, 876, 838, 801, 786 cm⁻¹; ¹H-NMR (DMSO-d$_6$+TFA+D$_2$O): δ 3.06 (1H, dd, J 7.1, 14.7 Hz), 3.16(1H, dd, J=6.0, 14.7 Hz), 3.77 (3H, s), 4.27 (1H, t, J=6.6 Hz), 4.98 (2H, s), 6.92-7.06 (5H, m), 7.10 (1H, br), 7.21 (1H, br d, J=7.9 Hz), 7.39 (1H, t, J=7.9 Hz), 7.41 (2H, s); ESI-MS m/z: 460 [M−H]⁻. Elemental analysis for C$_{23}$H$_{21}$Cl$_2$NO$_5$: Calculated: C, 59.75; H, 4.58; N, 3.03; Cl, 15.34. Found: C, 59.49; H, 4.41; N, 2.99; Cl, 15.23.

EXAMPLE 19

1) m.p.: 112-114° C.; IR (Nujol): 3269, 1746, 1706 cm⁻¹; APCI-MS m/z: 533 [M+H]⁺.

2) m.p.: 215-220° C. (dec.); IR (Nujol): 3395, 1583 cm⁻¹; ¹H-NMR (DMSO-d$_6$+TFA+D$_2$O): δ 3.06 (1H, dd, J=7.0, 14 Hz), 3.18 (1H, dd, J=6.0, 14 Hz), 4.30 (1H, quasi-t), 5.55 (2H, s), 7.43 (2H, s),7.50-7.55 (3H, m), 7.81 (1H, s), 7.92-7.97 (2H, m); ESI-MS m/z: 421 [M−H]⁻. Elemental analysis for C$_{19}$H$_{16}$Cl$_2$N$_2$O$_3$S.H$_2$O: Calculated: C, 51.71; H, 4.11; N, 6.35; Cl, 16.00; S, 7.23. Found: C, 51.57; H, 3.95; N, 6.44; Cl, 15.96; S, 7.20.

EXAMPLE 20

1) m.p.: 119-121° C.; IR (Nujol): 3273, 1741, 1702 cm⁻¹; ESI-MS m/z: 512 [M−H]⁻.

2) m.p.: 220-226° C. (dec.); IR (Nujol): 3390, 1585 cm⁻¹; ¹H-NMR (DMSO-d$_6$+TFA+D$_2$O): δ 3.05 (1H, dd, J=7.3, 14 Hz), 3.09 (1H, dd, J=6.2, 14 Hz), 3.62 (2H, t, 6.8 Hz), 4.23 (1H, quasi-t), 4.31 (2H, t, J=6.8 Hz), 7.36 (2H, s), 7.45-7.62 (4H, m), 7.85 (1H, br d), 7.95 (1H, m), 8.14 (1H, br d); ESI-MS m/z: 402 [M−H]⁻. Elemental analysis for C$_{21}$H$_{19}$Cl$_2$NO$_3$.H$_2$O: Calculated: C, 59.73; H, 5.01; N, 3.32; Cl, 16.79. Found: C, 59.51; H, 4.88; N, 3.35; Cl, 16.76.

EXAMPLE 21

1) m.p.: 109-111° C.; IR (Neat): 3400, 3320, 1740, 1713, 1557, 1506 cm⁻¹; ESI-MS m/z: 556[M−H]⁻.

2) m.p.: 193° C. (dec.); IR (Nujol): 3631, 3294, 1603, 1589, 1509, 1405, 1312, 1264, 1248, 1205, 974, 842, 786 cm⁻¹; ¹H-NMR (DMSO-d$_6$+TFA+D$_2$O): δ 3.05 (1H, dd, J=7.2, 14,Hz), 3.15 (1H, dd, J=5.8, 14 Hz), 4.0-4.5 (1H, overlapped with H$_2$O), 4.96 (2H, s), 6.78-6.85 (2H, m), 6.88-6.95 (3H, m), 7.08 (1H, br), 7.17 (1H, br d, J=7.9 Hz), 7.37 (1H, t, J=8.0 Hz), 7.41 (2H, s); ESI-MS m/z: 446 [M−H]⁻. Elemental analysis for C$_{22}$H$_{19}$Cl$_2$NO$_5$.0.8H$_2$O: Calculated: C, 57.11; H, 4.49; N, 3.03; Cl, 15.32. Found: C, 57.24; H, 4.34; N, 3.02; Cl, 15.09.

EXAMPLE 22

1) m.p.: 203-205° C.; IR (Nujol): 3256, 1747, 1702, 1613 cm⁻¹; ESI-MS m/z: 581 [M−H]⁻.

2) m.p.: 239-241° C. (dec.), IR (Nujol): 3457, 1614 cm⁻¹; ¹H-NMR (DMSO-d$_6$): δ 2.84 (1H, dd, J=7.9, 14 Hz), 3.08 (1H, dd, J=4.6, 14 Hz), 3.50 (1H, dd, J=4.6, 7.9 Hz), 5.32 (2H, s), 6.99 (2H, m),7.35-7.52 (4H, m), 7.74 (1H, dd, J=1.1, 7.9 Hz), 7.96 (2H, m); ESI-MS m/z: 471 [M−H]⁻. Elemental analysis for C$_{23}$H$_{18}$Cl$_2$N$_2$O$_5$.0.8H$_2$O: Calculated: C, 56.64; H, 4.05; N, 5.76; Cl, 14.54. Found: C, 57.05; H, 4.12; N, 5.56; Cl, 13.99.

EXAMPLE 23

1) m.p.: 120-122° C.; IR (Nujol): 3291, 1751, 1701, 1555 cm⁻¹; ESI-MS m/z: 579 [M−H]⁻.

2) m.p.: 205-215° C. (dec.); IR (Nujol): 3400, 3270, 1613, 1553, 1263, 1002, 794 cm⁻¹; ¹H-NMR (DMSO-d$_6$+TFA+D$_2$O): δ 3.00 (1H, dd, J=7.2, 14 Hz), 3.10 (1H, dd, J=6.2, 14 Hz), 3.48 (2H, t, J=6.2 Hz), 4.22 (1H, t, J=6.4 Hz), 4.44 (2H, t, J=6.3 Hz), 7.33 (2H, s), 7.34-7.45 (2H, m), 7.60-7.72 (4H, m), 8.19-8.25 (2H, m); ESI-MS m/z: 469 [M−H]⁻. Elemental analysis for C$_{24}$H$_{20}$Cl$_2$N$_2$O$_4$.0.6H$_2$O: Calculated: C, 59.79; H, 4.43; N, 5.81; Cl, 14.71. Found: C, 59.56; H, 4.15; N, 5.75; Cl, 14.72.

EXAMPLE 24

1) m.p.: 127-130° C.; IR (Nujol): 3283, 1739, 1703, 1557 cm⁻¹; ESI-MS m/z: 538 [M−H]⁻.

2) m.p.: 240-242° C. (dec.); IR (Nujol): 3400, 3260, 1622, 1274, 1191, 1002, 794, 757, 747 cm⁻¹; ¹H-NMR (DMSO-d$_6$+TFA+D$_2$O): δ 3.08 (1H, dd, J=7.0, 14 Hz), 3.18 (1H, dd, J=6.0, 14 Hz), 4.30 (1H, t, J=6.3 Hz), 5.44 (2H, s), 7.41-7.49 (4H, m), 753-7.60 (1H, m), 7.64-7.69 (1H, m), 7.72 (1H, br d, J=8.2 Hz), 8.18 (2H, br d, J=7.7 Hz); ESI-MS m/z: 428 [M−H]⁻. Elemental analysis for C$_{22}$H$_{17}$Cl$_2$NO$_4$.0.5H$_2$O: Calculated: C, 60.15; H, 4.13; N, 3.19; Cl, 16.14. Found: C, 60.33; H, 4.02; N, 3.15; Cl, 16.12.

EXAMPLE 25

1) m.p.: 138-142° C.; IR (Nujol): 3280, 1743, 1702 cm⁻¹; ESI-MS m/z: 595 [M−H]⁻.

2) m.p.: 237-240° C. (dec.); IR (Nujol): 3400, 1616 cm⁻¹; ¹H-NMR (DMSO-d$_6$+TFA+D$_2$O): α 3.02 (1H, dd, J=7.6, 14 Hz), 3.14 (1H, dd, J=6.2, 14 Hz), 3.89 (3H, s), 5.39 (2H, s), 7.19 (2H, m), 7.40-7.48 (3H, m), 7.52 (1H, dd, J=1.2, 7.7 Hz), 7.79 (1H, dd, J=1.2, 7.7Hz), 8.10 (2H, m); ESI-MS m/z: 487 [M+H]⁺. Elemental analysis for C$_{24}$H$_{20}$Cl$_2$N$_2$O$_5$.H$_2$O: Calculated: C, 57.04; H, 4.39; N, 5.54; Cl, 14.08. Found: C, 56.97; H, 4.15; N, 5.54; Cl, 14.06.

EXAMPLE 26

1) m.p.: 116-117° C.; IR (Nujol): 3295, 1750, 1735, 1701 cm⁻¹; ESI-MS m/z: 538 [M−H]⁻.

2) m.p.: 221-223° C. (dec.); IR (Nujol): 3050-2600, 1605 cm⁻¹; ¹H-NMR (DMSO-d$_6$): δ 2.32 (3H, s), 2.90 (1H, dd, J=7.7, 14 Hz), 3.09(1H, dd, J=4.8, 14 Hz), 3.47 (1H, dd, J=4.8, 7.7 Hz), 5.04 (2H, s),7.20-7.65 (12H, m); ESI-MS m/z: 428 [M−H]⁻. Elemental analysis for C$_{23}$H$_{21}$Cl$_2$NO$_3$.0.2H$_2$O: Calculated: C, 63.66; H, 4.97; N, 3.23; Cl, 16.34. Found: C, 63.77; H, 4.77; N, 3.22; Cl, 16.21.

EXAMPLE 27

1) m.p.: 97-98° C.; IR (Nujol): 3271, 1751, 1704, 1557 cm⁻¹; ESI-MS m/z: 524 [M−H]⁻.

2) m.p.: 210-212° C. (dec.); IR (Nujol): 3400, 1627 cm⁻¹; ¹H-NMR (DMSO-d$_6$): δ 2.85 (1H, dd, J=7.7, 14 Hz), 3.06 (1H, dd, J=4.8, 14 Hz), 3.43 (1H, dd, J=4.8, 7.7 Hz), 4.90 (2H, s), 7.0-8.0 (13H, m); ESI-MS m/z: 414 [M−H]⁻.

Elemental analysis for $C_{22}H_{19}Cl_2NO_4.0.7H_2O$: Calculated: C, 61.61; H, 4.79; N, 3.27; Cl, 16.53. Found: C, 61.62; H, 4.59; N, 3.28; Cl, 16.47.

EXAMPLE 28

1) m.p.: 158-161° C.; IR (Nujol): 3267, 1739, 1701, 1554 cm$^{-1}$; ESI-MS m/z: 595 [M−H]$^-$.

2) m.p.: 220-223° C. (dec.); IR (Nujol): 3400, 1601, 1552, 1305, 1259, 1237, 1195, 1033, 965, 957, 872, 798, 787, 729 cm$^{-1}$; $^1$H-NMR (DMSO-d$_6$+TFA+D$_2$O): δ 3.04 (1H, dd, J=7.2, 14 Hz), 3.14 (1H, dd, J=6.0, 14 Hz), 3.90 (3H, s), 4.29 (1H, t, J=6.5 Hz), 5.40 (2H, s), 7.24 (1H, dd, J=2.2, 7.9 Hz), 7.45 (2H, s), 7.48 (1H, d, J=7.7 Hz), 7.53-7.60 (2H, m), 7.65-7.69 (1H, m), 7.77 (1H, d, J=7.9 Hz), 7.86 (1H, br d, J=7.9 Hz); ESI-MS m/z: 485 [M−H]$^-$. Elemental analysis for $C_{24}H_{20}Cl_2N_2O_5.0.5H_2O$: Calculated: C, 58.08; H, 4.26; N, 5.64; Cl, 14.29. Found: C, 57.89; H, 4.19; N, 5.60; Cl, 14.35.

EXAMPLE 29

1) m.p.: 71-79° C.; IR (Nujol): 3285, 1741, 1705, 1557 cm$^{-1}$; ESI-MS m/z: 538 [M−H]$^-$.

2) m.p.: 205-208° C. (dec.); IR (Nujol): 3400, 1622, 1595 cm$^{-1}$; $^1$H-NMR (DMSO-d$_6$): δ 2.88 (1H, dd, J=7.7, 14 Hz), 3.08 (1H, dd, J=4.8, 14 Hz), 3.46 (1H, dd, J=4.8, 7.7 Hz), 4.20 (2H, s), 4.95 (2H, s), 7.14-7.38 (8H, m), 7.40 (2H, s), 7.56-7.59 (1H, m); ESI-MS m/z: 428 [M−H]$^-$. Elemental analysis for $C_{23}H_{21}Cl_2NO_3.0.5H_2O$: Calculated: C, 62.88; H, 5.05; N, 3.19; Cl, 16.14. Found: C, 62.89; H, 5.06; N, 3.11; Cl, 15.90.

EXAMPLE 30

1) m.p.: 218-219° C.; IR (Nujol): 3270, 1740, 1700 cm$^{-1}$; ESI-MS m/z: 599 [M−H]$^-$.

2) m.p.: 209-211° C.; IR (Nujol): 3640, 3400, 1620 cm$^{-1}$; $^1$H-NMR (DMSO-d$_6$+TFA+D$_2$O): δ 3.04 (1H, dd, J=7.3, 15 Hz), 3.14 (1H, dd, J=6.1, 15 Hz), 4.30 (1H, dd, J=6.1, 7.3 Hz), 5.41 (2H, s), 7.44 (2H, s), 7.47 (1H, dd, J=7.8, 7.8 Hz), 7.59 (1H, dd, J=1.1, 7.8 Hz), 7.70-7.75 (2H, m), 7.86 (1H, dd, 1.1, 7.8 Hz), 8.14-8.20 (2H, m); ESI-MS m/z: 489 [M−H]$^-$. Elemental analysis for $C_{23}H_{17}Cl_3N_2O_4.H_2O$: Calculated: C, 54.19; H, 3.76; N, 5.50; Cl, 20.86. Found: C, 54.13; H, 3.77; N, 5.34; Cl, 20.91.

EXAMPLE 31

1) m.p.: 150-152° C.; IR (Nujol): 3270, 1740, 1700 cm$^{-1}$; ESI-MS m/z: 599 [M−H]$^-$.

2) m.p.: 207-209° C. (dec.), IR (Nujol): 3400, 1580 cm$^{-1}$; $^1$H-NMR. (DMSO-d$_6$+TFA+D$_2$O): δ 3.04 (1H, dd, J=7.0, 14 Hz), 3.14 (1H, dd, J=5.9, 14 Hz), 4.28 (1H, dd, J=5.9, 7.0 Hz), 5.42 (2H, s), 7.44 (2H, s), 7.48 (1H, dd, J=7.7, 7.9 Hz), 7.60 (1H, dd, J=1.1, 7.7 Hz), 7.68 (1H, dd, J=7.3, 8.1 Hz), 7.73 (1H, ddd, J=1.7, 2.0, 8.1 Hz), 7.87 (1H, dd, J=1.1, 7.9 Hz), 8.10-8.13 (1H, m), 8.13 (1H, ddd, J=1.5, 1.7, 7.3 Hz); ESI-MS m/z: 489 [M−H]$^-$. Elemental analysis for $C_{23}H_{17}Cl_3N_2O_4.1.6H_2O$: Calculated: C, 53.07; H, 3.91; N, 5.38; Cl, 20.43. Found: C, 52.79; H, 3.56; N, 4.88; Cl, 20.59.

EXAMPLE 32

1) m.p.: 199-200° C.; IR (Nujol): 3260, 1740, 1700, 1615, 1600 cm$^{-1}$; ESI-MS m/z: 583[M−H]$^-$.

2) m.p.: 233-236° C. (dec.); IR (Nujol): 3360, 1620, 1600 cm$^{-1}$; $^1$H-NMR (DMSO-d$_6$+TFA+D$_2$O): δ 3.05 (1H, dd, J=7.1, 15 Hz), 3.14 (1H, dd, J=5.9, 15 Hz), 4.27 (1H, dd, J=5.9, 7.1 Hz), 5.42 (2H, s), 7.44 (2H, s), 7.43-7.53 (3H, m), 7.57 (1H, d, J=7.3 Hz), 7.84 (1H, d, J=7.9 Hz), 8.19-8.26 (2H, m); ESI-MS m/z: 473 [M−H]$^-$.

EXAMPLE 33

1) m.p.: 183-185° C.; IR (Nujol): 3280, 1749, 1704 cm$^{-1}$; ESI-MS m/z: 566 [M−H]$^-$.

2) m.p.: 214-218° C. (dec.); IR (Nujol): 3374, 1614. cm$^{-1}$; $^1$H-NMR (DMSO-d$_6$+TFA+D$_2$O): δ 3.15 (1H, dd, J=7.2, 14 Hz), 3.25 (1H, dd, J=6.2, 14 Hz), 4.27 (1H, t-like), 5.45 (2H, s), 7.45 (2H, s), 7.57 (1H, t, J=8.0 Hz), 7.70 (1H, dd, J=1.1, 8.0 Hz), 7.99 (1H, dd, J=1.1, 8.0 Hz), 8.37 (2H, m), 9.01 (2H, m); ESI-MS m/z: 458 [M+H]$^+$. Elemental analysis for $C_{22}H_{17}Cl_2N_3O_4.H_2O$: Calculated: C, 55.48; H, 4.02; N, 8.86; Cl, 14.89. Found: C, 55.34; H, 3.80; N, 8.66; Cl, 14.78.

EXAMPLE 34

1) m.p.: 174-176° C.; IR (Nujol): 3262, 1737, 1703 cm$^{-1}$; ESI-MS m/z: 555 [M−H]$^-$.

2) m.p.: 227-230° C. (dec.); IR (Nujol): 1644, 1612 cm$^{-1}$; $^1$H-NMR (DMSO-d$_6$+TFA+D$_2$O): δ 3.05 (1H, dd, J=7.2, 14 Hz), 3.15 (1H, dd, J=6.0, 14 Hz), 4.27 (1H, t-like), 5.38 (2H, s), 6.84 (1H, dd, J=1.8, 3.5 Hz), 7.40 (1H, dd, J=0.7, 3.5 Hz), 7.43 (2H, s), 7.46 (1H, t, J=7.7 Hz), 7.54 (1H, dd, J=1.2, 7.7 Hz), 7.82 (1H, dd, J=1.2, 7.7 Hz), 7.82 (1H, dd, J=1.2, 7.7 Hz), 8.07 (1H, dd, J=0.7, 1.8); ESI-MS m/z: 445 [M−H]$^-$. Elemental analysis for $C_{21}H_{16}Cl_2N_2O_5$: Calculated: C, 56.37; H, 3.61; N, 6.26; Cl, 15.85. Found: C, 56.08; H, 3.48; N, 6.13; Cl, 16.14.

EXAMPLE 35

1) m.p.: 168-170° C.; IR (Nujol): 3269, 1747, 1704, 1607 cm$^{-1}$; ESI-MS m/z: 609 [M−H]$^-$.

2) m.p.: 210-213° C. (dec.); IR (Nujol): 3363, 1607 cm$^{-1}$; $^1$H-NMR (DMSO-d$_6$+TFA+D$_2$O): δ 2.47 (3H, s), 3.05 (1H, dd, J=7.2, 14 Hz), 3.14 (1H, dd, J=6.4, 14 Hz), 3.88 (3H, s), 5.33 (2H, s), 7.15-7.20 (2H, m), 7.33 (1H, br s), 7.43 (2H, s), 7.58 (1H, br s), 8.05-8.10 (2H, m); ESI-MS m/z: 501 [M+H]$^+$. Elemental analysis for $C_{25}H_{22}Cl_2N_2O_5.1.5H_2O$: Calculated: C, 56.83; H, 4.77; N, 5.30; Cl, 13.42. Found: C, 56.77; H, 4.62; N, 5.25; Cl, 13.45.

EXAMPLE 36

1) m.p.: 179.5-180.5° C.; IR (Nujol): 3107, 1740, 1699, 1616, 1557 cm$^{-1}$; ESI-MS m/z: 579 [M−H]$^-$.

2) m.p.: 221-231° C. (dec.); IR (Nujol): 3381, 1583, 1557, 1522 cm$^{-1}$; $^1$H-NMR (DMSO-d$_6$+TFA+D$_2$O): δ 2.43 (3H, s), 3.03 (1H, dd, J=7.2, 15 Hz), 3.13 (1H, dd, J=6.0, 15 Hz), 4.28 (1H, t-like), 5.40 (2H, s), 7.42-7.48 (5H, m), 7.54 (1H, dd, J=1.1, 7.8 Hz), 7.83 (1H, dd, J=1:1,7.8 Hz), 8.06 (2H, d, J=8.2 Hz); ESI-MS m/z: 469 [M−H]$^-$.

EXAMPLE 37

1) m.p.: 132-133° C.; IR (Nujol): 3285, 1746, 1699, 1615, 1553, 1511 cm$^{-1}$; ESI-MS m/z: 608[M–H]$^{-}$.

2) m.p.: 219-222° C. (dec.); IR (Nujol): 3463, 1609, 1509 cm$^{-1}$; $^1$H-NMR (DMSO-d$_6$+TFA+D$_2$O): δ 2.98-3.07 (7H, m), 3.14 (1H, dd, J=5.8, 15 Hz), 4.28 (1H, t-like), 5.37 (2H, s), 6.86-6.91 (2H, m), 7.38 (1H, t, J=7.7 Hz), 7.42-7.47 (3H, m), 7.71 (1H, dd, J=1.5, 7.7 Hz), 7.94-8.01 (2H m); ESI-MS m/z: 498 [M–H]$^{-}$. Elemental analysis for C$_{25}$H$_{23}$Cl$_2$N$_3$O$_4$.1.5H$_2$O: Calculated: C, 56.93; H, 4.97; N, 7.97; Cl, 13.44. Found: C, 56.93; H, 4.95; N, 7.83; Cl, 13.49.

EXAMPLE 38

1) m.p.: 159-163° C.; IR (Nujol): 3258, 1738, 1700 cm$^{-1}$; ESI-MS m/z: 565 [M–H]$^{-}$.

2) m.p.: 219-223° C. (dec.); IR (Nujol): 1615 cm$^{-1}$; $^1$H-NMR (DMSO-d$_6$+TFA+D$_2$O): δ 3.06 (1H, dd, J=6.8, 15 Hz), 3.16 (1H, dd, J=5.8, 15 Hz), 4.29 (1H, t-like), 5.47 (2H, s), 7.44 (2H, s), 7.50 (1H, t, J=7.9 Hz), 7.61-7.68 (4H, m), 7.82 (1H, br d), 8.18-8.22 (2H, m); ESI-MS m/z: 455 [M–H]$^{-}$. Elemental analysis for C$_{23}$H$_{18}$Cl$_2$N$_2$O$_4$.0.8H$_2$O: Calculated: C, 58.56; H, 4.19; N, 5.94; Cl, 15.03. Found: C, 58.53; H, 3.97; N, 6.11; Cl, 14.91.

EXAMPLE 39 m.p.: 202-204° C. (dec.); IR (Nujol): 3400, 3290, 1635 cm$^{-1}$; $^1$H-NMR (DMSO-d$_6$+TFA+D$_2$O): δ 2.08 (3H, s), 2.97 (1H, dd, J=7.2, 15 Hz), 3.06 (1H, dd, J=6.2, 15 Hz), 4.23 (1H, t-like), 5.35 (2H, s), 7.24 (2H, s), 7.51-7.62 (4H, m), 7.68-7.73 (2H, m), 7.96 (1H, br d), 8.15(1H, br d); ESI-MS m/z: 496 [M–H]$^{-}$. Elemental analysis for C$_{26}$H$_{21}$Cl$_2$NO$_5$.1.5H$_2$O: Calculated: C, 59.44; H, 4.60; N, 2.67; Cl, 13.50. Found: C, 59.52; H, 4.13; N, 2.65; Cl, 13.50.

EXAMPLE 40

1) O-[2-[2-(3-Benzyloxyphenyl)-oxazol-4-yl]ethyl]-3,5-dichloro-N-trifluoroacetyl-L-tyrosine methyl ester was synthesized from 3,5-dichloro-N-trifluoroacetyl-L-tyrosine methyl ester by a similar manner to that of Example 6-1).

m.p.: 111-113° C.; IR (Nujol): 3270, 1745, 1706, 1555 cm$^{-1}$; ESI-MS m/z: 635 [M–H]$^{-}$.

2) A mixture of O-[2-[2-(3-benzyloxyphenyl)-oxazol-4-yl]ethyl]-3,5-dichloro-N-trifluoroacetyl-L-tyrosine methyl ester (316 mg, 0.496 mmol), hydrochloric acid (3 ml) and acetic acid (1.5 ml) was heated under reflux for 6 hrs. The reaction mixture was cooled to room temperature and the solvent was distilled off under reduced pressure. Water (30 ml) was added to the residue and the mixture was adjusted to pH 4-5 with 10% aqueous sodium hydroxide. The precipitates were collected by filtration, washed with water, suspended in ethanol (20 ml) and triturated. The resultant product was collected by filtration, washed with ethanol and dried under reduced pressure to give 3,5-dichloro-O-[2-[2-(3-hydroxyphenyl)-oxazol-4-yl]-L-tyrosine (115 mg, 52%) as a pale brown solid.

m.p.: 230-233° C. (dec.); IR (Nujol): 3400, 1601, 1266, 1013, 876, 733 cm$^{-1}$; $^1$H-NMR (DMSO-d$_6$+TFA+D$_2$O): δ 2.99-3.10 (3H, m), 3.13 (1H, dd, J=6.0, 14 Hz), 4.1-4.3 (3H, overlapped with H$_2$O), 6.89-6.95 (1H, m), 7.30-7.44 (5H, m), 8.01 (1H, s); ESI-MS m/z: 435 [M–H]$^{-}$. Elemental analysis for C$_{20}$H$_{18}$Cl$_2$N$_2$O$_5$.0.6H$_2$O: Calculated: C, 53.61; H, 4.32; N, 6.25; Cl, 15.82. Found: C, 53.67; H, 4.35; N, 6.26; Cl, 15.57.

EXAMPLE 41

1) O-[3-(t-Butoxycarbonylamino)propyl]-3,5-dichloro-N-trifluoroacetyl-L-tyrosine methyl ester was synthesized from 3,5-dichloro-N-trifluoroacetyl-L-tyrosine methyl ester by a similar manner to that of Example 6-1).

m.p.: 90-91.5° C.; IR (Nujol): 3355, 3303, 1738, 1701, 1681, 1553, 1537 cm$^{-1}$; APCI-MS m/z: 534 [M+NH$_4$]$^{+}$.

2) 8% Hydrochloric acid/dioxane (10 ml) was added to O-[3-(t-butoxycarbonylamino)propyl]-3,5-dichloro-N-trifluoroacetyl-L-tyrosine methyl ester (891 mg, 1.72 mmol) and the mixture was stirred at room temperature for 3 hrs. The solvent of the reaction mixture was distilled off under reduced pressure. To the residue was added a mixture of methanol and diisopropyl ether. The insoluble material was triturated, collected by filtration, washed with diisopropyl ether and dried under reduced pressure to give O-(3-aminopropyl)-3,5-dichloro-N-trifluoroacetyl-L-tyrosine methyl ester hydrochloride (782 mg, 100%) as a colorless powder.

IR (Nujol): 3308, 1744, 1704, 1556 cm$^{-1}$; ESI-MS m/z: 417 [M+H]$^{+}$.

3) A solution of benzoyl chloride (94 mg, 0.669 mmol) in ethyl acetate (2 ml) was added dropwise to a two-layer solution of O-(3-aminopropyl)-3,5-dichloro-N-trifluoroacetyl-L-tyrosine methyl ester hydrochloride (209 mg, 0.461 mmol) and sodium bicarbonate (150 mg, 1.79 mmol) in ethyl acetate (3 ml)-water (2 ml) with stirring under ice cooling and the mixture was stirred at the same temperature for 1 hr. The reaction mixture was diluted with ethyl acetate (20 ml) and the organic layer was separated, washed with brine and dried. The solvent was distilled off under reduced pressure. The residue was purified by flash column chromatography on silica gel (n-hexane/ethyl acetate=2–1) to give O-(3-benzoylaminopropyl)-3,5-dichloro-N-trifluoroacetyl-L-tyrosine methyl ester (253 mg, 100%) as a colorless oil.

IR (Neat): 3300, 3069, 2955, 1748, 1723, 1643, 1539 cm$^{-1}$; ESI-MS m/z: 519 [M–H]$^{-}$.

4) The protective groups of O-(3-benzoylaminopropyl)-3,5-dichloro-N-trifluoroacetyl-L-tyrosine methyl ester were removed by hydrolysis in a similar manner to Example 6-2) to give O-[(3-benzoylamino)propyl]-3,5-dichloro-L-tyrosine.

m.p.: 219-224° C. (dec.); IR (Nujol): 3657, 3300, 3232, 1631, 1578, 1555, 1403, 1379, 1265, 1209, 1048, 926, 875, 802, 705 cm$^{-1}$; $^1$H-NMR (DMSO-d$_6$+TFA+D$_2$O): δ 2.00-2.14 (2H, m), 3.03 (1H, dd, J=7.4, 14.5 Hz), 3.14 (1H, dd, J=5.8, 14.5 Hz), 3.50 (2H, t, J=7.0 Hz), 4.04 (2H, t, J=6.2 Hz), 4.27 (1H, t, J=6.5 Hz), 7.39 (2H, s), 7.43-7.57. (3H, m), 7.80-7.86 (2H, m); ESI-MS m/z: 409 [M–H]$^{-}$. Elemental analysis for C$_{19}$H$_{20}$Cl$_2$N$_2$O$_4$.0.5H$_2$O: Calculated: C, 54.30; H, 5.04; N, 6.67; Cl, 16.87. Found: C, 54.05; H, 4.76; N, 6.55; Cl, 16.74.

EXAMPLE 42

Following object compounds were synthesized from 3,5-dichloro-N-trifluoroacetyl-L-tyrosine methyl ester in a similar manner to Example 41-1)-4).

1) Pale yellow oil: IR (Neat): 3263, 2976, 1751, 1727, 1694, 1667, 1556 cm$^{-1}$; ESI-MS m/z: 529.

2) Colorless foam: IR (Neat+CHCl$_3$) 3310, 3199, 2957, 1747, 1717, 1557 cm$^{-1}$; ESI-MS m/z: 431 [M+H]$^{+}$.

3) Colorless oil: IR (Neat): 3230, 3065, 2953, 1749, 1723, 1617 cm$^{-1}$; ESI-MS m/z: 533 [M–H]$^{-}$.

4) m.p.: 189-193° C. (dec.); IR (Nujol), 1265, 1072, 1041, 795, 722 cm$^{-1}$; $^1$H-NMR (DMSO-d$_6$+TFA+D$_2$O): δ 1.90-2.20 (2H, m), 2.90-3.20 (2H, m), 2.94 (3H, br s), 3.49 (1H, br), 3.68 (1H, br), 4.05 (2H, br), 4.27 (1H, br), 7.30-7.49 (7H, m); ESI-MS m/z: 423 [M−H]⁻.

Elemental analysis for $C_{20}H_{22}Cl_2N_2O_4 \cdot 0.1H_2O$: Calculated: C, 56.24; H, 5.24; N, 6.56; Cl, 16.60. Found: C, 56.10; H, 5.20; N, 6.45; Cl, 16.49.

EXAMPLE 43

1) 3,5-Dichloro-N-trifluoroacetyl-O-[2-[4-[bis-[2-(tetrahydropyran-2-yloxy) ethyl]amino]phenyl]-benzoxazol-7-yl]methyl-L-tyrosine methyl ester was synthesized from 3,5-dichloro-N-trifluoroacetyl-L-tyrosine methyl ester in a similar manner to Example 6-1).

Pale yellow oil: IR (Neat): 3264, 2943, 1749, 1722, 1611, 1505 cm⁻¹; ESI-MS m/z: 836 [M−H]⁻.

2) A mixture of 3,5-dichloro-N-trifluoroacetyl-O-[2-[4-[bis-[2-(tetrahydropyran-2-yloxy)ethyl]amino]phenyl]-benzoxazol-7-yl]-methyl-L-tyrosine methyl ester (501 mg, 0.60 mmol), p-toluenesulfonic acid mono-hydrate (11 mg, 0.06 mmol) and methanol (60 ml) was stirred at room temperature for 18 hrs. The reaction mixture was neutralized with aqueous sodium bicarbonate, and the methanol was distilled off under reduced pressure. The residue was extracted with chloroform and the extract was washed with brine and dried. The solvent was distilled off under reduced pressure. The residue was purified by column chromatography on silica gel (chloroform/methanol=30–20) to give 3,5-dichloro-N-trifluoroacetyl-O-[2-[4-[bis-(2-hydroxyethyl)amino]phenyl]-benzoxazol-7-yl]methyl-L-tyrosine methyl ester (269 mg, 67%) as a pale yellow powder.

m.p.: 18.9-191° C.; IR (Nujol): 3270, 1750, 1700, 1610, 1600 cm⁻¹; ESI-MS m/z: 670[M+H]⁺, 692 [M+Na]⁺.

3) Triethylamine (81 mg, 0.80 mmol) and methanesulfonyl chloride (80 mg, 0.69 mmol) were added in turn to a solution of 3,5-dichloro-N-trifluoroacetyl-O-[2-[4-[bis-(2-hydroxyethyl)amino]phenyl]-benzoxazol-7-yl]methyl-L-tyrosine methyl ester (179 mg, 0.27 mmol) in methylene chloride (10 ml) and the mixture was stirred at room temperature for 24 hrs. Triethylamine (27 mg, 0.27 mmol) and methanesulfonyl chloride (12 mg, 0.11 mmol) were further added to the mixture. The reaction mixture was stirred at room temperature for 2 hrs., diluted with methylene chloride, washed with water and dried. The solvent was distilled off under reduced pressure. To the residual colorless powder were added methanol (6 ml) and lithium chloride (340 mg, 8.0 mmol) and the mixture was heated under reflux for 24 hrs. After cooling to room temperature, the reaction mixture was diluted with chloroform and water and then the organic layer was separated, washed with brine and dried. The solvent was distilled off under reduced pressure. The residue was purified by column chromatography on silica gel (chloroform/ethyl acetate=80) to give 3,5-dichloro-O-[2-[4-[bis-(2-chloroethyl)amino]phenyl]-benzoxazol-7-yl] methyl-N-trifluoroacetyl-L-tyrosine methyl ester (138 mg, 73%) as colorless powder.

IR (Nujol): 3280, 1745, 1720, 1615, 1605 cm⁻¹; ESI-MS m/z: 704 [M−H]⁻.

4) Protecting groups of 3,5-dichloro-O-[2-[4-[bis-(2-chloroethyl)amino]phenyl]-benzoxazol-7-yl]methyl-N-trifluoroacetyl-L-tyrosine methyl ester were removed by hydrolysis in a similar manner to Example 6-2) to give 3,5-dichloro-O-[2-[4-[bis-(2-chloroethyl)amino]phenyl]-benzoxazol-7-yl]methyl-L-tyrosine as a pale yellow powder.

IR (Nujol): 1620, 1605 cm⁻¹; ¹H-NMR (DMSO-d₆+TFA+D₂O): δ 3.04 (1H, dd, J=7.3, 15 Hz), 3.14 (1H, dd, J=6.0, 15 Hz), 3.77-3.91 (4H, m), 4.28 (1H, dd, J=6.0, 7.3 Hz), 5.37 (2H, s), 6.98 (2H,d, J=9.0 Hz), 7.39 (1H, dd, J=7.7, 7.7 Hz), 7.44 (2H, s), 7.46 (1H, dd, J=1.1, 7.7 Hz), 7.74 (1H, dd, J=1.1, 7.7 Hz), 7.99 (2H, d, J=9.0 Hz); ESI-MS m/z: 594 [M−H]⁻. Elemental analysis for $C_{27}H_{25}Cl_4N_3O_4 \cdot 2H_2O$: Calculated: C, 51.20; H, 4.61; N, 6.63; Cl, 22.39. Found: C, 51.40; H, 4.46; N, 6.52; Cl, 22.55.

EXAMPLE 44

1) Pyridine (0.584 ml, 7.22 mmol) and triethylamine (0.968 ml, 6.94 mmol)were added in turn to a suspension of 3,5-dichloro-N-trifluoroacetyl-L-tyrosine methyl ester (500 mg, 1.39 mmol), 1-naphthlene boronic acid (765 mg, 4.44 mmol), molecular sieves 4A powder (720 mg) and cppoer (II) acetate (390 mg, 2.08 mmol) in 1,2-dichloroethane(20 ml), and the mixture was stirred under air atmosphere (without argon) at room temperature for 24 hrs. The reaction mixture was diluted with ethyl acetate, and the insoluble materials were filtered off (celite (Trade mark)) and washed with ethyl acetate. The filtrate and washings were combined, washed with 10% hydrochloric acid and brine in turn and dried. The solvent was distilled off under reduced pressure. The residue was purified by column chromatography on silica gel (n-hexane/diethyl ether=2) to give 3,5-dichloro-N-trifluoroacetyl-O-(1-naphthyl)-L-tyrosine methyl ester (151 mg, 22%) as colorless crystals.

IR (Nujol): 3313, 1715 cm⁻¹; ESI-MS m/z: 484 [M−H]⁻.

2) Protecting groups of 3,5-dichloro-N-trifluoroacetyl-O-(1-naphthyl)-L-tyrosine methyl ester were removed by hydrolysis in a similar manner to Example 6-2) to give 3,5-dichloro-O-(1-naphthyl)-L-tyrosine.

m.p.: 218-221° C. (dec.); IR (Nujol): 1630, 1598 cm⁻¹; ¹H-NMR (DMSO-d₆+TFA+D₂O): δ 3.14 (1H, dd, J=7.9, 14 Hz), 3.30 (1H, dd, J=5.7, 14 Hz), 4.37 (1H, m), 6.46 (1H, d, J=7.8 Hz), 7.36 (1H, t, J=7.8 Hz), 7.56-7.70 (5H, m), 7.96-8.04 (1H, m), 8.32-8.38 (1H, m); ESI-MS m/z: 374 [M−H]⁻.

EXAMPLE 45

1) 3,5-Dichloro-N-trifluoroacetyl-O-[(6-methoxy)-2-naphthyl]-L-tyrosine methyl ester was synthesized from 3,5-dichloro-N-trifluoroacetyl-L-tyrosine methyl ester in a similar manner to Example 44-1).

m.p.: 188-189° C.; IR (Nujol): 3301, 1757, 1702 cm⁻¹; ESI-MS m/z: 514 [M−H]⁻.

2) A mixture of 3,5-dichloro-N-trifluoroacetyl-O-[(6-methoxy)-2-naphthyl]-L-tyrosine methyl ester (160 mg, 0.31 mmol), 47% hydrobromic acid (3 ml) and acetic acid (2 ml) was heated under reflux for 5 hrs. The reaction mixture was diluted with water (10 ml), adjusted to pH 4-5 with 4N sodium hydroxide under ice cooling and then stirred at room temperature for 30 min. The precipitates were collected by filtration, washed with water and dried under reduced pressure to give 3,5-dichloro-O-[(6-hydoxy)-2-naphthyl]-L-tyrosine (92 mg, 76%) as a pale orange powder.

m.p.: 241-245° C. (dec.); IR (Nujol): 1613 cm⁻¹; ¹H-NMR (DMSO-d₆+TFA+D₂O): δ 3.13 (1H, dd, J=7.9, 14 Hz), 3.28 (1H, dd, J=5.7, 14 Hz), 6.92 (1H, d, J=2.6 Hz), 7.08 (1H, dd, J=2.4, 8.8 Hz), 7.15 (1H, d, J=2.4 Hz), 7.18 (1H, dd, J=2.6, 9.0 Hz), 7.57 (2H, s), 7.58 (1H, d, J=8.8 Hz), 7.73 (1H, d, J=9.0 Hz); ESI-MS m/z: 390 [M−H]⁻. Elemental analysis for $C_{19}H_{15}Cl_2NO_4 \cdot 0.7H_2O$: Calculated: C, 56.37; H, 4.08; N, 3.46; Cl, 17.51. Found: C, 56.17; H, 3.87; N, 3.38; Cl, 17.48.

EXAMPLE 46

1) 3,5-Dichloro-N-trifluoroacetyl-O-[2-[3-(4-methoxyphenoxy)phenyl]ethyl]-L-tyrosine methyl ester was obtained in a similar manner to Example 44-1) as a pale orange oil from 3,5-dichloro-N-trifluoroacetyl-O-[2-(3-hydroxyphenyl)ethyl]-L-tyrosine methyl ester synthesized in a similar manner to Example 6-1).

IR (Neat): 3319, 2954, 1747, 1719, 1584, 1555, 1504 cm$^{-1}$; APCI-MS m/z: 586 [M+H]$^+$.

2) Trimethylsilyl chloride (0.25 ml, 1.97 mmol) was added dropwise to a solution of 3,5-dichloro-N-trifluoroacetyl-O-[2-[3-(4-methoxyphenoxy)phenyl]ethyl]-L-tyrosine methyl ester (190 mg, 0.324 mmol) and sodium iodide (292 mg, 1.95 mmol) in acetonitrile (3 ml) at room temperature. The mixture was stirred under argon atmosphere at room temperature for 22 hrs. and then heated under reflux for 9 hrs. The reaction mixture was poured into water (30 ml) and 10% aqueous sodium thiosulfate (20 ml) was added thereto. The mixture was extracted with ethyl acetate and the extract was washed with brine and then dried. The solvent was distilled off under reduced pressure. The residue was purified by column chromatography on silica gel (n-hexane/ethyl acetate=3) to give 3,5-dichloro-N-trifluoroacetyl-O-[2-[3-(4-hydroxyphenoxy)-phenyl]ethyl]-L-tyrosine methyl ester (120 mg, 65%) as a colorless oil.

IR (Neat): 3319, 1745, 1713, 1556, 1506 cm$^{-1}$; ESI-MS m/z: 570 [M–H]$^-$.

3) Protecting groups of 3,5-dichloro-N-trifluoroacetyl-O-[2-[3-(4-hydroxyphenoxy)phenyl]ethyl]-L-tyrosine methyl ester were removed by hydrolysis in a similar manner to Example 6-2) to give 3,5-dichloro-O-[2-[3-(4-hydroxyphenoxy)phenyl]-ethyl]-L-tyrosine.

m.p.: 190° C. (dec.); IR (Nujol): 3400, 1600, 1585, 1505, 1265, 1239, 1207, 1142, 989, 800 cm$^{-1}$; $^1$H-NMR (DMSO-d$_6$+TFA+D$_2$O): δ 2.98-3.12 (3H, m), 3.13 (1H, dd, J=5.9, 14 Hz), 4.10-4.22 (1H, overlapped with H$_2$O), 4.25 (2H, t, J=6.5 Hz), 6.73-6.82 (3H, m), 6.84-6.92 (3H, m), 7.02 (1H, br d, J=7.5 Hz), 7.27 (1H, t, J=7.9 Hz), 7.36 (2H, s); ESI-MS m/z: 460 [M–H]$^-$. Elemental analysis for C$_{23}$H$_{21}$Cl$_2$NO$_5$.0.7H$_2$O: Calculated: C, 58.17; H, 4.75; N, 2.95; Cl, 14.93. Found: C, 58.09; H, 4.47; N, 2.90; Cl, 14.77.

EXAMPLE 47

1) Potassium carbonate (180 mg, 1.30 mmol) and 7-chloromethyl-2-phenylbenzo[b]furan. (171 mg, 0.705 mmol) were added in turn to a solution of 3,5-dichloro-N-trifluoroacetyl-L-tyrosine methyl ester (221 mg, 0.614 mmol) in acetone (3 ml) with stirring under ice cooling and the mixture was stirred under argon atmosphere at the same temperature for 5 hrs. Dimethylformamide (2 ml) and n-tetrabutylammonium iodide (23 mg, 0.062 mmol) were added to the mixture and stirred at room temperature for 21 hrs. The reaction mixture was poured into ice-water (50 ml) and extracted with ethyl acetate. The extract was washed with water and saturated brine solution in turn and dried. The solvent was distilled off under reduced pressure. The residue was purified by flash column chromatography on silica gel (n-hexane/ethyl acetate=5) to give 3,5-dichloro-N-trifluoroacetyl-O-[(2-phenylbenzo[b]fur-7-yl)methyl]-L-tyrosine methyl ester (182 mg, 52%) as colorless crystals.

m.p.: 141-145° C.; IR (Nujol): 3270, 1736, 1707, 1557 cm$^{-1}$; ESI-MS m/z: 564 [M–H]$^-$.

2) Protecting groups of 3,5-dichloro-N-trifluoroacetyl-O-[(2-phenylbenzo[b]fur-7-yl)methyl]-L-tyrosine methyl ester were removed by hydrolysis in a similar manner to Example 6-2) to give 3,5-dichloro-O-[(2-phenylbenzo[b]fur-7-yl)methyl]-L-tyrosine.

m.p.: 220-223° C. (dec.); IR (Nujol): 3400, 1624, 1269, 972, 910, 811, 799, 772, 742 cm$^{-1}$; $^1$H-NMR (DMSO-d$_6$+TFA+D$_2$O): δ 3.03 (1H, dd, J=7.3, 14.5 Hz), 3.14(1H, dd, J=6.1, 14.5 Hz), 4.24-4.32 (1H, m), 5.40 (2H, s), 7.32 (1H, t, J=7.6 Hz), 7.40-7.57 (7H, m), 7.69-7.74 (1H, m), 7.90 (2H, d, J=7.1 Hz); ESI-MS m/z: 454 [M–H]$^-$. Elemental analysis for C$_{24}$H$_{19}$Cl$_2$NO$_4$.1.3H$_2$O: Calculated: C, 60.09; H, 4.54; N, 2.92; Cl, 14.78. Found: C, 60.07; H, 4.26; N, 2.88; Cl, 14.55.

EXAMPLE 48

By a similar method to Example 47, an object compound was synthesized from 3,5-dichloro-N-trifluoroacetyl-L-tyrosine methyl ester via the corresponding intermediate.

1) m.p.: 252-255° C.; IR (Nujol)3265, 3115, 1739, 1703, 1605, 1556 cm$^{-1}$; ESI-MS m/z: 581 [M–H]$^-$.

2) Amorphous powder; IR (Nujol): 3370, 1603, 1584, 1554, 1313, 1259, 1235, 964, 788, 732 cm$^{-1}$; $^1$HNMR (DMSO-d$_6$+TFA+D$_2$O): δ 3.05 (1H, dd, J=7.1, 15 Hz), 3.15 (1H, dd, J=6.0, 15 Hz), 4.28 (1H, t, J=6.5 Hz), 5.41 (2H, s), 7.07 (1H, dd, J=1.9, 8.0 Hz), 7.44 (2H, s), 7.42-7.50(2H,m), 7.53-7.66 (3H, m), 7.84 (1H, br d, J=7.7 Hz); ESI-MS m/z: 471 [M–H]$^-$. Elemental analysis for C$_{23}$H$_{18}$Cl$_2$N$_2$O$_5$.0.7H$_2$O: Calculated: C, 56.85; H, 4.02; N, 5.76; Cl, 14.59. Found: C, 56.94; H, 4.19; N, 5.65; Cl, 14.44.

EXAMPLE 49

1) Pyridine (0.22 ml, 2.72 mmol) was added to a suspension of N-trifluoroacetyl-3-hydroxy-L-phenylalanine ethyl ester (159 mg, 0.521 mmol), 2-naphthaleneboronic acid (186 mg, 1.08 mmol), molecular sieves 4A powder (204 mg) and copper (II) acetate (153 mg, 0.842 mmol) in methylene chloride (7 ml) and the mixture was stirred under air atmosphere (without argon) at room temperature for 16 hrs. The reaction mixture was diluted with ethyl acetate (30 ml) and the insoluble materials were filtered off (celite (Trade mark)) and washed with ethyl acetate. The filtrate and washings were combined and washed with 10% hydrochloric acid and brine in turn and then dried. The solvent was distilled off under reduced pressure. The resultant residue was purified by column chromatography on silica gel (n-hexane/ethyl acetate=10) to give N-trifluoroacetyl-3-(2-naphthyloxy)-L-phenylalanine ethyl ester (200 mg, 89%) as pale yellow crystals.

m.p.: 78-80° C.; IR (Nujol): 3308, 1753, 1703, 1630, 1583, 1557 cm$^{-1}$; ESI-MS m/z: 430 [M–H]$^-$.

2) 0.5 N Lithium hydroxide (1.6 ml, 0.8 mmol) was added to a solution of N-trifluoroacetyl-3-(2-naphthyloxy)-L-phenylalanine ethyl ester (94 mg, 0.219 mmol) in tetrahydrofuran (2 ml) at 5° C. and the mixture was reacted at 5° C. for 69 hrs. The reaction mixture was adjusted to pH 3-4 with 1N hydrochloric acid and the precipitates were collected by filtration. The resultant solid was washed with water and ethanol in turn and then dried to give 3-(2-naphthyloxy)-L-phenylalanine (57 mg, 78%) as a colorless solid.

m.p.: 210-214° C. (dec.); IR (Nujol): 3400, 3200, 1637, 1582, 1267, 1171, 862 cm$^{-1}$; $^1$H-NMR (DMSO-d$_6$+TFA+ D$_2$O): δ 3.05-3.20 (2H, m), 4.23 (1H, t, J=6.7 Hz), 6.99-7.12 (3H, m), 7.31 (1H, dd, J=2.6, 9.0 Hz), 7.38-7.55 (4H, m), 7.81 (1H, br d, J=7.9 Hz), 7.92 (1H, br d, J=7.9 Hz), 7.97 (1H, d, J=8.8 Hz); ESI-MS m/z: 306 [M–H]$^-$. Elemental analysis for $C_{19}H_{17}NO_3 \cdot 1.35 H_2O$: Calculated: C, 68.81; H, 5.99; N, 4.22. Found: C, 68.58; H, 5.70; N, 4.18.

3) 3-(2-naphthyloxy)-L-phenylalanine methyl ester hydrochloride was synthesized from 3-(2-naphthyloxy)-L-phenylalanine by a conventional method.

m.p.: 209-211° C. (dec.); IR (Nujol): 1741, 1611, 1582 cm$^{-1}$; $^1$H-NMR (DMSO-d$_6$): δ 3.13 (1H, dd, J=7.0, 14 Hz), 3.16 (1H, dd, J=6.1, 14 Hz), 3.64 (3H, s), 4.30 (1H, t-like), 6.98-7.09 (3H, m), 7.30 (1H, dd, J=2.4, 8.9 Hz), 7.36-7.53 (4H, m), 7.81 (1H, br d, J=7.9 Hz), 7.92 (1H, br d, J=7.9 Hz), 7.98 (1H, d, J=8.9 Hz), 8.55(2H, br); APCI-MS m/z: 322 [M+H]$^+$. Elemental analysis for $C_{20}H_{19}NO_3 \cdot HCl$: Calculated: C, 67.13; H, 5.63; N, 3.92; Cl, 9.91. Found: C, 66.98; H, 5.70; N, 4.17; Cl, 9.66.

EXAMPLE 50

1) Yellow oil: IR (CHCl$_3$) 3300, 1745, 1720 cm$^{-1}$; ESI-MS m/z: 431 [M−H]$^-$.

2) m.p.: 162-164° C. (dec.); IR (Nujol): 3550, 3480, 1730 cm$^{-1}$; $^1$H-NMR (D$_2$O): δ 3.26 (1H, dd, J=7.1, 14 Hz), 3.35 (1H, dd, J=6.0, 14 Hz), 4.26 (1H, dd, J=6.0, 7.1 Hz), 7.17 (1H, d, J=1.6 Hz), 7.20 (1H, dd, J=1.5, 8.1 Hz), 7.27 (1H, d, J=7.7 Hz), 7.53 (1H, dd, J=7.7, 8.1 Hz), 7.60 (1H, d, J=2.5 Hz), 7.94 (1H, dd, J=2.5, 9.3 Hz), 8.00 (1H, dd, J=5.5, 8.5 Hz), 8.26 (1H, d, J=9.3 Hz), 8.90 (1H, d, J=8.5 Hz), 8.99 (1H, dd, J=1.5, 5.5 Hz); APCI-MS m/z: 309 [M+H]$^+$. Elemental analysis for $C_{18}H_{16}N_2O_3 \cdot 2HCl \cdot 1.4H_2O$: Calculated: C, 53.19; H, 5.16; N, 6.89; Cl, 17.44. Found: C, 53.66; H, 5.07; N, 6.66; Cl, 17.11.

EXAMPLE 51

1) Brown oil: IR (Neat) 3320, 1740, 1715 cm$^{-1}$; ESI-MS m/z: 420 [M−H]$^-$.

2) m.p.: 233-235° C. (dec.); IR (Nujol): 3670, 3350, 1620, 1580 cm$^{-1}$; $^1$H-NMR (DMSO-d$_6$): δ 2.84 (1H, dd, J=8.6, 15 Hz), 3.14 (1H, dd, J=4.6, 15 Hz), 3.37 (1H, dd, J=4.6, 8.6 Hz), 6.76-6.81 (1H, m), 6.92 (1H, dd, J=0.9, 2.2 Hz), 6.95-6.98 (1H, m), 7.02 (1H, d, J=7.1 Hz), 7.03 (1H, dd, J=2.2, 8.8 Hz), 7.26 (1H, dd, J=7.1, 7.9 Hz), 7.29 (1H, d, J=2.4 Hz), 7.60 (1H, d, J=8.8 Hz), 8.02 (1H, d, J=2.2 Hz); APCI-MS m/z: 298 [M+H]$^+$. Elemental analysis for $C_{17}H_{15}NO_4 \cdot LiCl \cdot 2H_2O$: Calculated: C, 54.34; H; 5.10; N, 3.73; Cl, 9.44; Li, 1.85: Found: C, 54.36; H, 4.92; N, 3.57; Cl, 9.39; Li, 1.91.

EXAMPLE 52

1) Colorless oil: IR (Neat) 3409, 3103, 2983, 1714, 1605, 1579, 1552 cm$^{-1}$; ESI-MS m/z: 419 [M−H]$^-$.

2) m.p.: 205-210° C. (dec.); IR (Nujol): 3619, 3405, 1620, 1579 cm$^{-1}$; $^1$H-NMR (DMSO-d$_6$): δ 2.80 (1H, dd, J=8.4, 14 Hz), 3.12 (1H, dd, J=4.3, 14 Hz), 3.35 (1H, dd, J=4.3, 8.4 Hz), 6.38 (1H, m), 6.68-6.71 (1H, m), 6.83 (1H, dd, J=2.3, 8.6 Hz), 6.90 (1H, m), 6.95 (1H, br d), 7.18-7.23 (2H, m), 7.37 (1H, t, J=2.8 Hz), 7.40 (1H, d, J=8.6 Hz), 11.2(1H, s); ESI-MS m/z: 295 [M−H]$^-$. Elemental analysis for $C_{17}H_{16}N_2O_3 \cdot H_2O$: Calculated: C, 64.96; H, 5.77; N, 8.91. Found: C, 65.08; H, 5.51; N, 8.74.

EXAMPLE 53

1) Colorless oil: IR (Neat) 3323, 3064, 3034, 2983, 2937, 1716, 1599, 1584, 1570, 1505 cm$^{-1}$; ESI-MS m/z: 456 [M−H]$^-$.

2) m.p.: 203-206° C. (dec.); IR (Nujol): 3627, 3385, 2619, 1613, 1583, 1572, 1549 cm$^{-1}$; $^1$H-NMR (DMSO-d$_6$): δ 2.86 (1H, dd, J=8.2, 14 Hz), 3.14 (1H, dd, J=4.6, 14 Hz), 3.39 (1H, dd, J=4.6, 8.2 Hz), 6.88-6.92 (1H, m), 6.98-7.09 (3H, m), 7.28-7.48 (7H, m), 7.62-7.67 (2H, m); ESI-MS m/z: 332 [M−H]$^-$. Elemental analysis for $C_{21}H_{19}NO_3 \cdot 0.6H_2O$: Calculated: C, 73.28; H, 5.92; N, 4.07. Found: C, 73.13; H, 5.96; N, 4.04.

EXAMPLE 54

1) Colorless oil: IR (Neat) 3321, 1715 cm$^{-1}$; ESI-MS m/z: 430 [M−H]$^-$.

2) m.p.: 180-186° C. (dec.); IR (Nujol): 3329, 1628 cm$^{-1}$; $^1$H-NMR (DMSO-d$_6$): δ 2.85 (1H, dd, J=8.2, 14 Hz), 3.15 (1H, dd, J=4.3, 14 Hz), 3.39 (1H, dd, J=4.3, 8.2 Hz), 6.79-6.85 (1H, m), 7.01 (1H, dd, J=0.9, 7.7 Hz), 7.05-7.10 (2H, m), 7.25-7.32 (1H, m), 7.45 (1H, t, J=8.0 Hz), 7.51-7.61 (2H, m), 7.71 (1H, d, J=8.4 Hz), 7.96-8.00,(1H, m), 8.08-8.13 (1H, m); ESI-MS m/z: 306 [M−H]$^-$. Elemental analysis for $C_{19}H_{17}NO_3 \cdot 0.9H_2O$: Calculated: C, 70.53; H, 5.86; N, 4.33. Found: C, 70.51; H, 5.69; N, 4.28.

EXAMPLE 55

1) According to the method of Example 49, N-t-butoxycarbonyl-3-[2-(6-methoxy)naphthyloxy]-L-phenylalanine methyl ester was synthesized from N-t-butoxycarbonyl-3-hydroxy-L-phenylalanine methyl ester.

Pale yellow foam; IR (Neat+CHCl$_3$) 3375, 1745, 1714, 1604, 1584, 1508 cm$^{-1}$; APCI-MS m/z: 469 [M+NH$_4$]$^+$.

2) 25% Hydrochloric acid/ethyl acetate(1.5 ml) was added to a solution of N-t-butoxycarbonyl-3-[2-(6-methoxy) naphthyl-oxy]-L-phenylalanine methyl ester (415 mg, 0.919 mmol) in ethyl acetate (5 ml) and the mixture was stirred at room temperature for 22 hrs. The reaction mixture was diluted with diethyl ether (6 ml) and the precipitates were collected by filtration, washed with diethyl ether and then dried under reduced pressure to give 3-[2-(6-methoxy)naphthyloxy]-L-phenylalanine methyl ester hydrochloride (328 mg, 92%) as colorless crystals.

m.p.: 194-196° C.; IR (Nujol): 1743 cm$^{-1}$; APCI-MS m/z: 352 [M+H]$^+$.

3) 3-[2-(6-Methoxy)naphthyloxy]-L-phenylalanine methyl ester hydrochloride was subjected to hydrolysis reaction in a similar manner to Example 49-2) to give 3-[2-(6-methoxy)naphthyloxy]-L-phenylalanine.

m.p.: 202-206° C. (dec.); IR (Nujol): 3105, 1632, 1607, 1579, 1509 cm$^{-1}$; $^1$H-NMR-(DMSO-d$_6$+TFA+D$_2$O): δ 3.05-3.18 (2H, m), 3.87 (3H, s), 4.21 (1H, t, J=6.4 Hz), 6.96-7.07 (3H, m), 7.18 (1H, dd, J=2.4, 9.0 Hz), 7.27 (1H, dd, J=2.4, 9.0 Hz), 7.34-7.42 (3H, m), 7.75 (1H, d, J=9.0 Hz), 7.88 (1H, d, J=9.0 Hz); ESI-MS m/z: 336 [M−H]$^-$. Elemental analysis for $C_{20}H_{19}NO_4 \cdot 0.7H_2O$: Calculated: C, 68.64; H, 5.87; N, 4.00. Found: C, 68.78; H, 5.58; N, 3.96.

EXAMPLE 56

1) Trimethylsilyl iodide (0.29 ml, 2.04 mmol) was added to a suspension of 3-[2-(6-methoxy)naphthyloxy]-L-phenylalanine methyl ester hydrochloride (79 mg, 0.204 mmol) in acetonitrile (3 ml) and the mixture was reacted under argon atmosphere at 65-70° C. for 17 hrs. To the mixture was added trimethylsilyl iodide (0.29 ml)and the mixture was further stirred at the same temperature for 7 hrs. To the ice-cold reaction mixture was added saturated sodium sulfite solution (20 ml). The mixture was extracted with ethyl acetate and the extract was washed with brine and dried. The solvent was distilled off under reduced pressure and the residue was purified by preparative thin layer chromatography on silica gel (chloroform/methanol=20) to give 3-[2-(6-hydroxy)-naphthyloxy]-L-phenylalanine methyl ester (22 mg, 32%) as pale yellow solid.

APCI-MS m/z: 338 [M+H]$^+$.

2) 3-[2-(6-Hydroxy)naphthyloxy]-L-phenylalanine methyl ester was hydrolyzed in a similar manner to Example 49-2) to give 3-[2-(6-hydroxy)naphthyloxy]-L-phenylalanine.

m.p.: 210-220° C. (dec.); IR (Nujol): 3400, 2720, 1602, 1581, 1509 cm$^{-1}$; $^1$H-NMR (DMSO-d$_6$): δ 2.85 (1H, dd, J=8.3, 14 Hz), 3.14 (1H, dd, J=4.4, 14 Hz), 3.39 (1H, dd, J=4.4, 8.3 Hz), 6.85 (1H, dd, J=2.0, 8.0 Hz), 6.99-7.35 (7H, m), 7.66 (1H, d, J=9.0 Hz), 7.71 (1H, d, J=9.0 Hz), 9.80 (1H, br); ESI-MS m/z: 322 [M–H]$^-$.

EXAMPLE 57

1) N-Trifluoroacetyl-3-(4-methoxyphenoxy)-L-phenylalanine ethyl ester was synthesized from N-trifluoroacetyl-3-hydroxy-L-phenylalanine ethyl ester in a similar manner to Example 49-1).

Pale brown oil: IR (Neat) 3322, 2985, 1714, 1586, 1550, 1504 cm$^{-1}$; ESI-MS m/z: 410 [M–H]$^-$.

2) N-Trifluoroacetyl-3-(4-hydroxyphenoxy)-L-phenylalanine ethyl ester was synthesized from N-trifluoroacetyl-3-(4-methoxyphenoxy-L-phenylalanine ethyl ester in a similar manner to Example 56-1).

m.p.: 109-111° C.; IR (Nujol): 3427, 3309, 1722, 1701, 1615, 1583, 1551, 1507 cm$^{-1}$; ESI-MS m/z:396 [M–H]$^-$.

3) In a similar manner to Example 49-1), 3-[4-(4-hydroxyphenoxy)-phenoxy]-L-phenylalanine was synthesized by deprotecting by a conventional method from N-trifluoroacetyl-3-(4-hydroxyphenoxy)-L-phenylalanine ethyl ester via N-trifluoroacetyl-3-[4-(4-methoxyphenoxy)phenoxy]-L-phenylalanine ethyl ester. N-Trifluoroacetyl-3-[4-(4-methoxyphenoxy)phenoxy]-L-phenylalanine ethyl ester: m.p.: 67-71° C.; IR (Nujol): 3324, 1745, 1707, 1559, 1507, 1501 cm$^{-1}$; APCI-MS m/z: 504 [M+H]$^+$.

3-[4-(4-hydroxyphenoxy)phenoxy]-L-phenylalanine: m.p.: 234-237° C. (dec.); IR (Nujol): 3262, 3120, 1606, 1579, 1502, 1233, 1213, 829 cm$^{-1}$; $^1$H-NMR (DMSO-d$_6$+TFA+D$_2$O): δ 3.10 (2H, d, J=7.0 Hz), 4.19 (1H, t, J=6.3 Hz), 6.77-6.84 (2H, m), 6.85-6.98 (6H, m), 6.99-7.05 (3H, m), 7.34 (1H, t, J=7.9 Hz); ESI-MS m/z: 364 [M–H]$^-$.

Elemental analysis for C$_{21}$H$_{19}$NO$_5$.0.32H$_2$O: Calculated: C, 67.96; H, 5.33; N, 3.77. Found: C, 67.69; H, 5.03; N, 3.72.

EXAMPLE 58

1) 2-(Bromomethyl)naphthalene (453 mg, 1.97 mmol), potassium carbonate (340 mg, 2.46 mmol) and potassium iodide (14 mg, 0.084 mmol) were added in turn to a solution of N-trifluoroacetyl-3-hydroxy-L-phenylalanine ethyl ester (500 mg, 1.64 mmol) in methyl ethyl ketone (20 ml) and the mixture was stirred under argon atmosphere at 60° C. for 14 hrs. The reaction mixture was cooled to room temperature and the insoluble materials were filtered off and washed with ethyl acetate. The filtrate and washings were combined and washed with water and brine and then dried. The solvent was distilled off under reduced pressure. The residue was purified, by column chromatography on silica gel (n-hexane/ethyl acetate=12) to give N-trifluoroacetyl-3-[(2-naphthyl)methoxy]-L-phenylalanine ethyl ester (576 mg, 79%) as colorless crystals.

m.p.: 103-111° C.; IR (Nujol): 1743, 1707 cm$^{-1}$; ESI-MS m/z: 444 [M–H]$^-$.

2) N-Trifluoroacetyl-3-[(2-naphthyl)methoxy]-L-phenylalanine ethyl ester was hydrolyzed in a similar manner to Example 49-2) to give 3-[(2-naphthyl)methoxy]-L-phenylalanine.

m.p.: 201-204° C. (dec.); IR (Nujol): 1616, 1595 cm$^{-1}$; $^1$H-NMR (DMSO-d$_6$+TFA+D$_2$O): δ 3.10 (2H, d-like), 4.21 (1H, t-like), 5.27 (2H, s), 6.86 (1H, d, J=7.7 Hz), 6.97-7.04 (2H, m), 7.24-7.32 (1H, m), 7.50-7.62 (3H, m), 7.90-8.01 (4H, m); ESI-MS m/z: 320 [M–H]$^-$. Elemental analysis for C$_{20}$H$_{19}$NO$_3$: Calculated: C, 74.75; H, 5.96; N, 4.36. Found: C, 75.02; H, 5.91; N, 4.40.

EXAMPLE 59

1) In a similar manner to Example 58-1), N-t-butoxycarbonyl-3-[(2naphthoyl)methoxy]-L-phenylalanine methyl ester was synthesized from N-t-butoxycarbonyl-3-hydroxy-L-phenylalanine methyl ester.

m.p.: 111-112° C.; IR (Nujol): 3369, 1750, 1707, 1677 cm$^{-1}$; APCI-MS m/z: 464 [M+H]$^+$, 481 [M+NH$_4$]$^+$.

2) Palladium hydroxide carbon (50% water content, 180 mg) was added to a solution of N-t-butoxycarbonyl-3-[(2-naphthoyl)methoxy]-L-phenylalanine methyl ester (400 mg, 0.863 mmol) in methanol (13 ml) and the mixture was stirred in hydrogen stream at room temperature for 20 hrs. The catalyst was filtered off and the solvent of the filtrate was distilled off under reduced pressure. The residue was purified by column chromatography on silica gel (n-hexane/ethyl acetate=7) to give N-t-butoxycarbonyl-3-[2-[2-(5,6,7,8-tetrahydro-naphthyl)]ethoxy]-L-phenylalanine methyl ester (132 mg, 34%) and methyl ester of N-t-butoxycarbonyl-3-[2-(2-naphthyl)ethoxy]-L-phenylalanine (134 mg, 34%) (in turn of elution).

N-t-Butoxycarbonyl-3-[2-[2-(5,6,7,8-tetrahydro-naphthyl)]ethoxy]-L-phenylalanine methyl ester: Colorless oil: IR (Neat): 3400, 2928, 1745, 1717, 1601, 1584 cm$^{-1}$; $^1$H-NMR (CDCl$_3$): δ 1.40 (9H, s), 1.72-1.90 (4H, m), 2.74-3.12 (8H, m), 3.70 (3H, s), 4.11 (2H, t, J=7.0 Hz), 4.50-4.60 (1H, 4.96 (1H, br d), 6.64-6.73 (2H, m), 6.74-6.82 (1H, m), 6.97-7.01 (2H, m), 7.05-7.10 (1H, m), 7.14-7.23 (1H, m); APCI-MS m/z: 471 [M+NH$_4$]$^+$. N-t-Butoxycrbonyl-3-[2-(2-naphthyl)ethoxy]-L-phenylalanine methyl ester: Colorless oil: IR (Neat): 3373, 2975, 2951, 2871, 1745, 1715, 1601, 1584 cm$^{-1}$; $^1$H-NMR (CDCl$_3$): δ 1.38 (9H, s), 2.94-3.12 (2H, m), 3.24 (2H, t, J=7.0 Hz), 3.68 (3H, s), 4.24 (2H, t, J=7.0 Hz), 4.50-4.60 (1H, m), 4.96 (1H, br d), 6.66-6.72 (2H, m), 6.77-6.82 (1H, m), 7.18 (1H, t, J=7.9 Hz), 7.38 (3H, m), 7.72 (1H, br s), 7.76-7.84 (3H, m); APCI-MS m/z: 467 [M+NH$_4$]$^+$.

3) Trifluoroacetic acid (3 ml) was added to a solution of N-t-butoxycarbonyl-3-[2-(2-naphthyl)ethoxy]-L-phenylalanine methyl ester (125 mg, 0.278 mmol) in methylene chloride (3 ml) under ice cooling and the mixture was stirred at the same temperature for 30 min. The solvent of the reaction mixture was distilled off at room temperature under reduced pressure. The residue was triturated with n-hexane and collected by filtration. The resultant solid was dissolved in tetrahydrofuran (1.2 ml)-water (0.6 ml). Lithium hydroxide mono-hydrate (41 mg, 0.973 mmol) was added to the solution with stirring under ice cooling and the mixture was reacted at the same temperature for 12 hrs. The reaction mixture was diluted with water (2 ml) and adjusted to pH 3-4 with 1N HCl. After the addition of water (25 ml), the mixture was stirred at room temperature for 1 hr. The precipitates were collected by filtration, washed with water and then dried under reduced pressure to give 3-[2-(2-naphthyl)ethoxy]-L-phenylalanine (55 mg, 59%) as colorless crystals.

m.p.: 210-214° C. (dec.); IR (Nujol): 1669, 1603 cm$^{-1}$; $^1$H-NMR (DMSO-d$_6$+TFA+D$_2$O): δ 3.01-3.14 (2H, m), 3.22 (2H, t, J=6.7 Hz), 4.20 (1H, quasi-t), 4.29 (2H, t, J=6.7 Hz), 6.79-6.91 (3H, m),7.25 (1H, t, J=7.9 Hz), 7.44-7.54 (3H, m), 7.82-7.91 (4H, m); ESI-MS m/z: 334[M−H]$^-$. Elemental analysis for C$_{21}$H$_{21}$NO$_3$.0.2H$_2$O: Calculated: C, 74.40; H, 6.36; N, 4.13. Found: C, 74.52; H, 6.27; N, 4.13.

EXAMPLE 60

Protecting groups of N-t-butoxycarbonyl-3-[2-[2-(5,6,7,8-tetrahydronaphthyl)]ethoxy]-L-phenylalanine methyl ester were removed in a similar manner to Example 59-3) to give 3-[2-[2-(5,6,7,8-tetrahydro-naphthyl)]ethoxy]-L-phenylalanine.

m.p.: 198-202° C. (dec.); IR (Nujol): 1668, 1601 cm$^{-1}$; $^1$H-NMR (DMSO-d$_6$+TFA+D$_2$O): δ 1.66-2.02 (4H, m), 2.62-2.87 (4H, m),2.94 (2H, t, J=6.8 Hz), 3.00-3.12 (2H, m), 4.04-4.24 (3H, m), 6.78-6.91 (3H, m), 6.95-7.09 (3H, m), 7.20-7.29 (1H, m); ESI-MS m/z: 338 [M−H]$^-$. Elemental analysis for C$_{21}$H$_{25}$NO$_3$.0.2H$_2$O: Calculated: C, 73.53; H, 7.46; N, 4.08. Found: C, 73.54; H, 7.34; N, 4.09.

According to the method of Example 6, the object compounds of the following Examples 61-76 and Examples 80-85 were synthesized from 3,5-dichloro-N-trifluoroacetyl-L-tyrosine methyl ester via each corresponding intermediate.

EXAMPLE 61

1) m.p.: 198-200° C.; IR (Nujol): 3277, 1737, 1702, 1595, 1545 cm$^{-1}$; APCI-MS m/z: 590 [M+H]$^+$ 2) m.p.: 221-222° C. (dec.); IR (Nujol): 1593, 1545 cm$^{-1}$; $^1$H-NMR (DMSO-d$_6$+TFA+D$_2$O): δ 1.68 (6H, br s), 3.08 (1H, dd, J=7.3, 14 Hz), 3.18 (1H, dd, J=5.9, 14 Hz), 3.66 (4H, br s), 4.31 (1H, t-like), 5.16 (2H, s), 7.27 (1H, br d), 7.42 (1H, t-like), 7.47 (2H, s), 7.51 (1H, br d); ESI-MS m/z: 478 [M−H]$^-$. Elemental analysis for C$_{22}$H$_{23}$Cl$_2$N$_3$O$_3$S.0.65H$_2$O: Calculated: C, 53.69; H, 4.98; N, 8.54; Cl, 14.41; S, 6.51. Found: C, 53.67; H, 4.89; N, 8.41; Cl, 14.44; S, 6.46.

EXAMPLE 62

1) Colorless oil: IR (Neat) 3319, 1750, 1720 cm$^{-1}$; ESI-MS m/z: 571 [M−H]$^-$.

2) m.p.: 204-211° C. (dec.); IR (Nujol): 3382, 1605, 1581, 1566, 1522 cm$^{-1}$; ESI-MS m/z: 461 [M−H]$^-$. Elemental analysis for C$_{23}$H$_{24}$Cl$_2$N$_2$O$_4$1.1H$_2$O: Calculated: C, 57.17; H, 5.47; N, 5.80; Cl, 14.67. Found: C, 57.26; H, 5.37; N, 5.54; Cl, 14.64.

EXAMPLE 63

1) m.p.: 128.5-130° C.; IR (Nujol): 3268, 1739, 1705 cm$^{-1}$; ESI-MS m/z: 579 [M−H]$^-$.

2) m.p.: 198-200.5° C. (dec.); IR (Nujol): 3406, 1626, 1599, 1569, 1536 cm$^{-1}$; ESI-MS m/z: 471 [M+H]$^+$. Elemental analysis for C$_{24}$H$_{20}$Cl$_2$N$_2$O$_4$1.4H$_2$O: Calculated: C, 58.05; H, 4.63; N. 5.64; Cl, 14.28. Found: C, 58.17; H, 4.54; N, 5.31; Cl, 14.27.

EXAMPLE 64

1) m.p.: 186-188° C.; IR (Nujol): 3259, 1737, 1699, 1557 cm$^{-1}$; ESI-MS m/z: 581 [M−H]$^-$.

2) m.p.: 223-226° C. (dec.); IR (Nujol): 3395, 1585 cm$^{-1}$; $^1$H-NMR (DMSO-d$_6$+TFA+D$_2$O): δ 3.09 (1H, dd, J=7.2, 14 Hz), 3.19 (1H, dd, J=6.1, 14 Hz), 4.32 (1H, t-like), 5.30 (2H, s), 7.48 (2H, s), 7.57-7.66 (5H, m), 8.11-8.16 (3H, m); ESI-MS m/z: 471 [M−H]$^-$. Elemental analysis for C$_{23}$H$_{18}$Cl$_2$N$_2$O$_3$S.H$_2$O: Calculated: C, 56.22; H, 4.10; N, 5.70; Cl, 14.43; S, 6.52. Found: C, 56.10; H, 4.08; N, 5.32; Cl, 14.45; S, 6.47.

EXAMPLE 65

1) m.p.: 150-154° C.; IR (Nujol): 3277, 1746, 1701, 1616, 1604, 1553, 1512 cm$^{-1}$; ESI-MS m/z: 609 [M−H]$^-$.

2) m.p.: 233-236° C. (dec.); IR (Nujol): 3426, 1605, 1555, 1519 cm$^{-1}$; $^1$H-NMR (DMSO-d$_6$+TFA+D$_2$O): δ 3.06 (1H, dd, J=7.3, 14Hz), 3.16 (1H, dd, J=6.1, 14 Hz), 3.28 (6H, s), 4.29 (1H, t-like), 5.39 (2H, s), 7.26 (1H, d, J=9.5 Hz), 7.45 (2H, s), 7.46 (1H, dd, J=7.7, 7.7 Hz), 7.55 (1H, br d), 7.82 (1H, br d), 8.38 (1H, dd, J=2.2, 9.5 Hz), 8.67 (1H, d, J=2.2 Hz); ESI-MS m/z: 501 [M+H]$^+$. Elemental analysis for C$_{24}$H$_{22}$Cl$_2$N$_4$O$_4$.2H$_2$O: Calculated: C, 53.64; H, 4.88; N, 10.43; Cl, 13.19. Found: C, 53.35; H, 4.72; N, 9.83; Cl, 13.14.

EXAMPLE 66

1) m.p.: 128-130° C.; IR (Nujol): 3280, 1739, 1702, 1562, 1555 cm$^{-1}$; ESI-MS m/z: 592[M+H]$^+$.

2) m.p.: 204-214° C. (dec.); IR (Nujol): 3377, 1609, 1555, 1533 cm$^{-1}$; $^1$H-NMR (DMSO-d$_6$+TFA+D$_2$O): δ 3.07 (1H, dd, J=7.0, 14 Hz), 3.15 (1H, dd, J=6.3, 14 Hz), 3.50 (2H, t, J=7.1 Hz), 4.27 (1H, t-like), 5.07 (2H, t, J=7.1 Hz), 5.62 (2H, s), 7.43 (2H, s), 7.51-7.79 (5H, m), 7.93 (1H, dd, J=1.5, 7.9 Hz), 8.20 (1H, br d); ESI-MS m/z: 480 [M−H]$^-$. Elemental analysis for C$_{25}$H$_{21}$Cl$_2$N$_3$O$_3$.2H$_2$O: Calculated: C, 57.92; H, 4.86; N, 8.11; Cl, 13.68. Found: C, 57.98; H, 4.62; N, 7.89; Cl, 13.83.

EXAMPLE 67

1) Colorless amorphous solid: IR (Neat+CHCl$_3$) 3319, 1748, 1721 cm$^{-1}$; ESI-MS m/z: 603 [M+H]$^+$.

2) m.p.: 194-198° C. (dec.); IR (Nujol): 3395, 1583, 1557, 1506 cm$^{-1}$; $^1$H-NMR (DMSO-d$_6$+TFA+D$_2$O): δ 2.96 (1H, dd, J=7.1, 14 Hz), 3.07 (1H, dd, J=6.1, 14 Hz), 5.16 (2H, s), 7.34 (2H, s), 7.40-7.56 (3H, m), 7.66-7.78 (4H, m), 7.92-8.00 (2H, m), 8.07 (1H, dd, J=5.7, 8.0 Hz), 8.78 (1H, dd, J=1.6, 8.0 Hz), 8.95 (1H, dd, J=1.6, 5.7 Hz); ESI-MS m/z: 491 [M−H]$^-$. Elemental analysis for C$_{27}$H$_{22}$Cl$_2$N$_2$O$_3$.H$_2$O: Calculated: C, 63.41; H, 4.73; N, 5.48; Cl, 13.86. Found: C, 63.37; H, 4.70; N, 5.20; Cl, 13.87.

EXAMPLE 68

1) Colorless amorphous solid: IR (Neat+CHCl$_3$) 1747, 1720 cm$^{-1}$; ESI-MS m/z: 577 [M+H]$^+$.

2) m.p.: 205-210° C. (dec.); IR (Nujol): 3396, 1624, 1584, 1557, 1505 cm$^{-1}$; $^1$H-NMR (DMSO-d$_6$+D$_2$O): δ 2.84 (1H, dd, J=8.0, 14 Hz), 3.08 (1H, dd, J=4.2, 14 Hz), 3.47 (1H,dd, J=4.2, 8.0 Hz), 5.09 (2H, s), 7.32 (2H, s), 7.54-7.63 (3H, m), 7.73 (1H, dd, J=1.7, 8.4 Hz), 7.94-8.05 (3H, m), 8.11 (1H, br s), 8.22 (1H, dd, J=1.7, 7.8 Hz), 8.73 (1H, dd, J=1.7, 4.8 Hz); ESI-MS m/z: 465 [M−H]$^-$. Elemental analysis for $C_{25}H_{20}Cl_2N_2O_3 \cdot 0.8H_2O$: Calculated: C, 62.33; H, 4.52; N, 5.81; Cl, 14.72. Found: C, 62.39; H, 4.43; N, 5.62; Cl, 14.58.

EXAMPLE 69

1) m.p.: 111-115° C.; IR (Nujol): 3270, 1750, 1701 cm$^{-1}$; ESI-MS m/z: 582 [M+H]$^+$.

2) m.p.: 174-179° C. (dec.); IR (Nujol): 3400, 1588, 1555, 1511 cm$^{-1}$; $^1$H-NMR (DMSO-d$_6$+TFA+D$_2$O): δ 3.02-3.20 (4H, m), 3.82 (2H, t, J=5.7 Hz), 4.26 (1H, t-like), 4.77 (2H, s), 5.21 (2H, s), 7.18-7.31 (5H, m), 7.42 (2H, s), 8.24 (1H, dd, J=1.7, 6.0 Hz), 8.30 (1H, dd, J=1.7, 7.4 Hz); ESI-MS m/z: 472 [M+H]$^+$. Elemental analysis for $C_{24}H_{23}Cl_2N_3O_3 \cdot 1.2H_2O$: Calculated: C, 58.35; H, 5.18; N, 8.51; Cl, 14.35. Found: C, 58.15; H, 4.79; N, 8.28; Cl, 14.27.

EXAMPLE 70

1) m.p.: 195-196° C.; IR (Nujol): 3275, 1743, 1703 cm$^{-1}$; ESI-MS m/z: 612 [M+H]$^+$.

2) m.p.: 218-221° C. (dec.); IR (Nujol): 3412, 3195, 1681, 1614, 1543, 1520 cm$^{-1}$; $^1$H-NMR (DMSO-d$_6$+TFA+D$_2$O): δ 3.04 (1H, dd, J=7.0, 14 Hz), 3.14 (1H, dd, J=5.3, 14 Hz), 3.24 (6H, s), 4.28 (1H, t-like), 5.37 (2H, s), 7.30-7.45 (3H, m), 7.51 (1H, dd, J=1.1, 7.8Hz), 7.76 (1H, dd, J=1.1, 7.8 Hz), 8.96 (2H, s); ESI-MS m/z: 502 [M+H]$^+$. Elemental analysis for $C_{23}H_{21}Cl_2N_5O_4 \cdot 1.4H_2O$: Calculated: C, 52.36; H, 4.55; N, 13.27; Cl, 13.44. Found: C, 52.13; H, 4.51; N, 13.06; Cl, 13.25.

EXAMPLE 71

1) m.p.: 138-141° C.; IR (Nujol): 3280, 1754, 1704 cm$^{-1}$; ESI-MS m/z: 677 [M-H]$^-$.

2) m.p.: 199-204° C. (dec.); IR (Nujol): 3380, 1607, 1554 cm$^{-1}$; $^1$H-NMR (DMSO-d$_6$+TFA+D$_2$O): δ 2.95-3.16 (2H, m), 3.26 (1H, dd, J=9.0, 12 Hz), 3.60 (1H, dd, J=2.5, 12 Hz), 4.26 (1H, t-like), 5.00-5.06 (1H, m), 6.79-6.88 (2H, m), 6.94 (1H, dd, J=2.6, 6.8 Hz), 7.34 (2H, s), 7.36-7.47 (5H, m); ESI-MS m/z: 471 [M-H]$^-$. Elemental analysis for $C_{24}H_{22}Cl_2N_2O_4 \cdot 0.6H_2O$: Calculated: C, 59.54; H, 4.83; N, 5.79; Cl, 14.64. Found: C, 59.45; H, 4.64; N, 5.69; Cl, 14.51.

EXAMPLE 72

1) After condensation reaction, tetrahydropyranyl group was removed with p-toluenesulfonic acid in methanol.

Semi-solid: APCI-MS m/z: 642 [M+H]$^+$ 2) m.p.: 212-215° C. (dec.); IR (Nujol): 3345(br), 1617, 1599, 1572, 1534, 1522 cm$^{-1}$; $^1$H-NMR (DMSO-d$_6$+TFA+ D$_2$O): δ 3.03 (1H, dd, J=7.7, 15 Hz), 3.17 (1H, dd, J=6.9, 15 Hz), 3.65 (2H, t-like), 3.79 (2H, t-like), 5.37 (2H, s), 7.40-7.46 (3H, m), 7.52 (1H, br d), 7.77 (1H, dd, J=1.1, 7.9 Hz), 8.98 (2H, s); ESI-MS m/z: 530 [M-H]$^-$. Elemental analysis for $C_{24}H_{23}Cl_2N_5O_5 \cdot H_2O \cdot 0.1HCl$: Calculated: C, 52.03; H, 4.57; N, 12.64; Cl, 13.44. Found: C, 51.82; H, 4.52; N, 12.94; Cl, 13.45.

EXAMPLE 73

1) m.p.: 187-189° C.; IR (Nujol): 3165, 1750, 1731, 1715, 1621, 1577, 1556, 1543 cm$^{-1}$; APCI-MS m/z: 578 [M+H]$^+$.

2) m.p.: 200-208° C. (dec.); IR (Nujol): 3365, 1616, 1549 cm$^{-1}$; $^1$H-NMR (DMSO-d$_6$+TFA+D$_2$O): δ 3.07 (1H, dd, J=7.0, 14 Hz), 3.16 (1H, dd, J=6.4, 14 Hz), 4.28 (1H, t-like), 5.61 (2H, s), 5.90 (2H, s), 7.44 (2H, s), 7.56-7.63 (2H, m), 7.76-7.88 (2H, m), 7.96-8.01 (2H, m), 8.22 (1H, br d); ESI-MS m/z: 466 [M-H]$^-$. Elemental analysis for $C_{24}H_{19}Cl_2N_3O_3 \cdot 1.5H_2O$: Calculated: C, 58.19; H, 4.48; N, 8.48; Cl, 14.31. Found: C, 58.38; H, 4.53; N, 8.13; Cl, 14.04.

EXAMPLE 74

1) m.p.: 181-184° C.; IR (Nujol): 3269, 1747, 1703, 1597, 1559 cm$^{-1}$; ESI-MS m/z: 643[M-H]$^-$.

2) m.p.: 210-215° C. (dec.); IR (Nujol): 3381, 1591, 1558 cm$^{-1}$; $^1$H-NMR (DMSO-d$_6$+TFA+D$_2$O): δ 3.04 (1H, dd, J=7.3, 14Hz), 3.19 (1H, dd, J=6.0, 14 Hz), 4.03 (3H, s), 4.17 (3H, s), 5.29 (2H, s), 7.47 (2H, s), 7.50-7.64 (2H, m), 8.10 (1H, d, J=8.1 Hz), 9.29 (1H, s); ESI-MS m/z: 533 [M-H]$^-$.

EXAMPLE 75

1) m.p.: 168-170° C.; IR (Nujol): 3271, 1748, 1705, 1611, 1590, 1557, 1521 cm$^{-1}$; ESI-MS m/z: 600 [M-H]$^-$.

2) m.p.: 200-202° C. (dec.); IR (Nujol): 3386, 1605, 1557, 1519 cm$^{-1}$; $^1$H-NMR (DMSO-d$_6$+TFA+D$_2$O): δ 2.58 (3H, s), 2.80 (3H, s), 3.08 (1H, dd, J=7.2, 14 Hz), 3.18 (1H, dd, J=6.0, 14 Hz), 4.30 (1H, t-like), 5.30 (2H, s), 7.47 (2H, s), 7.59 (1H, br d), 7.64 (1H, t-like), 8.12 (1H, dd, J=1.4, 7.8 Hz); ESI-MS m/z: 490 [M-H]$^-$. Elemental analysis for $C_{22}H_{19}Cl_2N_3O_4S \cdot 0.9H_2O$: Calculated: C, 51.96; H, 4.12; N, 8.26; Cl, 13.94; S, 6.30. Found: C, 52.12; H, 4.07; N, 8.01; Cl, 13.79; S, 6.19.

EXAMPLE 76

1) Colorless powder: IR (Nujol): 3300, 3180, 1747, 1716, 1571, 1555 cm$^{-1}$; ESI-MS m/z: 601 [M-H]$^-$.

2) m.p.: 186-190° C. (dec.); IR (Nujol): 3396, 3267, 1599, 1585, 1571, 1555, 1518 cm$^{-1}$; $^1$H-NMR (DMSO-d$_6$+TFA+ D$_2$O): δ 3.03 (1H, dd, J=7.5, 14 Hz), 3.15 (1H, dd, J=5.8, 14 Hz), 4.27 (1H, t-like), 5.16 (2H, s), 7.40 (2H, s), 7.42-7.57 (3H, m), 7.77-7.83 (4H, m), 7.89-7,93 (2H, d, J=8.4 Hz), n 7.98 (1H, dd, J=5.4, 8.0 Hz), 8.68 (1H, dd, J=1.5, 8.0 Hz), 8.92 (1H, dd, J=1.5, 5.4 Hz); ESI-MS m/z: 491 [M-H]$^-$. Elemental analysis for $C_{27}H_{22}Cl_2N_2O_3 \cdot 0.55H_2O$: Calculated: C, 64.43; H, 4.63; N, 5.57; Cl, 14.09. Found: C, 64.45; H, 4.42; N, 5.49; Cl, 13.38.

EXAMPLE 77

The object compound of Example 39 was esterified by a conventional method to give the object compound of Example 77.

m.p.: 194-195.5° C. (dec.); IR (Nujol): 1738, 1625 cm$^{-1}$; $^1$H-NMR (DMSO-d$_6$): δ 1.14 (3H, t, J=7.0 Hz), 2.07 (3H, s), 3.04 (2H, d, J=7.0 Hz), 4.08-4.22 (2H, m), 4.29 (1H, t, J=7.0 Hz), 5.34 (2H, s), 7.29 (2H, s), 7.52 (1H, t, J=7.5 Hz), 7.53-7.61 (3H, m), 7.72 (2H, dd-like), 7.96 (1H, dd, J=1.5, 7.5 Hz), 8.13 (1H, dd, J=1.5, 7.5 Hz), 8.54 (3H, br s); APCI-MS m/z: 526 [free M+H]$^+$. Elemental analysis for $C_{28}H_{25}Cl_2NO_5 \cdot HCl \cdot 0.5H_2O$: Calculated: C, 58.81; H, 4.76; N, 2.45; Cl, 18.60. Found: C, 58.80; H, 4.53; N, 2.20; Cl, 18.71.

EXAMPLE 78

The object compound of Example 67 was esterified by a conventional method to give the object compound of Example 78.

m.p.: 57-71° C. (dec.); IR (Nujol): 3383, 1742 cm$^{-1}$; APCI-MS m/z: 521 [M+H]$^+$. Elemental analysis for $C_{29}H_{26}Cl_2N_2O_3.1.7HCl.1.7H_2O$: Calculated: C, 56.72; H, 5.10; N, 4.56; Cl, 21.36. Found: C, 56.58; H, 4.85; N, 4.56; Cl, 21.21.

EXAMPLE 79

The object compound of Example 61 was esterified by a conventional method to give the object compound of Example 79.

m.p.: –158° C.; IR (Nujol): 3381, 1744, 1625, 1537 cm$^{-1}$; $^1$H-NMR (DMSO-d$_6$): δ 1.18 (3H, t, J=7.0 Hz), 1.66 (6H, br s), 3.10-3.23 (2H, m), 3.66 (4H, br s), 4.30-4.40 (1H, m), 5.12 (2H, s), 7.72 (1H, d, J=6.6 Hz), 7.37 (1H, t-like), 7.50 (2H, s), 7.53 (1H, d, J=8.1 Hz), 8.60-8.80 (3H, br); APCI-MS m/z: 508 [free M+H]$^+$.

EXAMPLE 80

1) m.p.: 190-192° C.; IR (Nujol): 3257, 1749, 1704, 1608, 1563 cm$^{-1}$; ESI-MS m/z: 594 [M–H]$^-$.

2) m.p.: 215-217° C. (dec.); IR (Nujol): 3250, 1623, 1610, 1556 cm$^{-1}$; $^1$H-NMR (DMSO-d$_6$+TFA+D$_2$O): δ 3.03 (1H, dd, J=7.3, 14Hz), 3.14 (1H, dd, J=6.8, 14 Hz), 3.83 (3H, s), 5.35 (2H, s), 7.07 (1H, d, J=2.6 Hz), 7.22 (1H, d, J=2.6 Hz), 7.40 (1H, s), 7.42-7.44 (1H, m), 7.44 (2H, s), 7.48-7.55 (2H, m), 7.84-7.90 (2H, m); ESI-MS m/z: 484 [M–H]$^-$. Elemental analysis for $C_{25}H_{21}Cl_2NO_5.0.3H_2O$: Calculated: C, 61.06; H, 4.43; N, 2.85; Cl, 14.42. Found: C, 61.10; H, 4.21; N, 2.64; Cl, 14.27.

EXAMPLE 81

1) m.p.: 181-182° C.; IR (Nujol): 1749, 1733, 1703, 1639, 1602 cm$^{-1}$; ESI-MS m/z: 664 [M–H]$^-$.

2) m.p.: 218-221° C. (dec.); IR (Nujol): 1625 cm$^{-1}$; $^1$H-NMR (DMSO-d$_6$+TFA+D$_2$O): δ 2.96 (1H, dd, J=7.5, 15 Hz), 3.05 (1H, dd, J=6.0, 15 Hz), 4.22 (1H, br t, J=6.5 Hz), 4.35 (2H, s), 5.39 (2H, s), 7.23 (2H, s), 7.52-7.66 (4H, m), 7.90 (1H, dd-like, J=1.5, 8.0 Hz), 7.98 (1H, dd, J=1.5, 7.5 Hz), 8.16 (1H, dd, J=1.5, 8.0 Hz); ESI-MS m/z: 512 [M–H]$^-$. Elemental analysis for $C_{26}H_{21}Cl_2NO_6.H_2O$: Calculated: C, 58.66; H, 4.35; N, 2.63; Cl, 13.32. Found: C, 58.62; H, 4.38; N, 2.40; Cl, 13.04.

EXAMPLE 82

1) m.p.: 169-170° C.; IR (Nujol): 1738, 1704, 1636, 1605 cm$^{-1}$; ESI-MS m/z: 649 [M–H]$^-$.

2) m.p.: 191-195° C. (dec.); IR (Nujol): 1640, 1633 cm$^{-1}$; $^1$H-NMR (DMSO-d$_6$+TFA+D$_2$O): δ 2.66 (6H, s), 2.98 (1H, dd, J=7.0, 15 Hz), 3.08 (1H, dd, J=6.5, 15 Hz), 4.22 (1H, t, J=6.5 Hz), 4.24 (2H, s), 5.32 (2H, s), 7.26 (2H, s), 7.59-7.74 (6H, m), 8.11(1H, dd, J=1.5, 7.5 Hz), 8.23 (1H, dd, J=1.5, 8.0 Hz); APCI-MS m/z: 541 [M+H]$^+$. Elemental analysis for $C_{28}H_{26}Cl_2N_2O_5.H_2O$: Calculated: C, 60.11; H, 5.04; N, 5.01; Cl, 12.67. Found: C, 60.27; H, 5.01; N, 4.71; Cl, 12.21.

EXAMPLE 83

1) m.p.: 192-193° C.; IR (Nujol): 3395, 3317, 3273, 1746, 1707, 1621, 1608 cm$^{-1}$; ESI-MS m/z: 607 [M–H]$^-$.

2) m.p.: 226-230° C. (dec.); IR (Nujol): 1612, 1606 cm$^{-1}$; $^1$H-NMR (DMSO-d$_6$+TFA+D$_2$O): δ 2.96 (1H, dd, J=7.0, 15 Hz), 3.06 (1H, dd, J=6.0, 15 Hz), 4.22 (1H, br t, J=7.0 Hz), 5.43 (2H, s), 7.54 (1H, t, J=7.5 Hz), 7.55-7.60 (3H, m), 7.86-7.90 (2H, m), 7.96 (1H, dd, J=1.5, 7.5 Hz), 8.19 (1H, dd, J=1.5, 8.0 Hz); ESI-MS m/z: 497 [M–H]$^-$. Elemental analysis for $C_{25}H_{20}Cl_2N_2O_5.0.75H_2O$: Calculated: C, 58.55; H, 4.23; N, 5.46; Cl, 13.83. Found: C, 58.66; H, 4.28; N, 5.35; Cl, 13.53.

EXAMPLE 84

1) m.p.: 179-180° C.; IR (Nujol): 3277, 1749, 1708 cm$^{-1}$; ESI-MS m/z: 607 [M–H]$^-$.

2) m.p.: 226-230° C. (dec.); IR (Nujol): 1612 cm$^{-1}$; ESI-MS m/z: 497 [M–H]$^-$. Elemental analysis for $C_{26}H_{24}Cl_2N_2O_4.0.9H_2O$: Calculated: C, 60.57; H, 5.02; N, 5.43; Cl, 13.75. Found: C, 60.62; H, 4.99; N, 5.47; Cl, 13.73.

EXAMPLE 85

1) Colorless amorphous solid; IR (Neat+CHCl$_3$) 3319, 1721 cm$^{-1}$; ESI-MS m/z: 694 [M–H]$^-$.

2) After removing 2-(trimethylsilyl)ethoxymethyl group with hydrochloric acid by a conventional method, the intermediate was hydrolyzed in a similar manner to Example 6-2).

m.p.: 183-187° C. (dec.); IR (Nujol): 3350, 1601, 1556 cm$^{-1}$; $^1$H-NMR (DMSO-d$_6$+D$_2$O): δ 2.95 (1H, dd, J=7.9, 14 Hz), 3.14 (1H, dd, J=5.0, 14 Hz), 3.72 (1H, dd, J=5.0, 7.9 Hz), 5.49 (2H, s), 7.27 (1H, dd, J=7.7, 7.7 Hz), 7.42 (2H, s), 7.47-7.62 (5H, m), 8.18 (2H, br d); ESI-MS m/z: 456 [M+H]$^+$. Elemental analysis for $C_{23}H_{19}Cl_2N_3O_3.1.7H_2O$: Calculated: C, 56.73; H, 4.64; N, 8.63; Cl, 14.56. Found: C, 57.28; H, 4.56; N, 8.12; Cl, 14.35.

EXAMPLE 86

1) According to the method of Example 47-1), N-t-butoxycarbonyl-3,5-dichloro-O-[(3-dimethylcarbamoylflavon-8-yl)methyl]-L-tyrosine ethyl ester was synthesized from N-t-butoxycarbonyl-3,5-dichloro-L-tyrosine ethyl ester.

Colorless powder; IR (Nujol): 1740, 1712, 1645, 1636, 1605 cm$^{-1}$; APCI-MS m/z: 683 [M+H]$^+$.

2) Protective groups of N-t-butoxycarbonyl-3,5-dichloro-O-[(3-dimethylcarbamoylflavon-8-yl)methyl]-L-tyrosine ethyl ester were removed by a conventional method to give the object compound of Example 86.

m.p.: 213-216° C. (dec.); IR (Nujol): 3400, 1739, 1624 cm$^{-1}$; $^1$H-NMR (DMSO-d$_6$): δ 2.82 (3H, s), 2.91 (3H, s), 2.96 (1H, dd, J=7.0, 15 Hz), 3.07 (1H, dd, J=6.0, 15 Hz), 4.17 (1H, t, J=7.0 Hz), 5.43 (2H, s), 7.29 (2H, s), 7.50-7.63 (4H, m), 7.73 (2H, dd-like, J=1.5, 7.5 Hz), 8.03 (1H, dd, 1.5, 7.5 Hz), 8.13 (1H, dd, J=1.5, 8.0 Hz), 8.30 (3H, br); ESI-MS m/z: 553 [M–H]$^-$. Elemental analysis for $C_{28}H_{24}Cl_2N_2O_6.1.05HCl.2H_2O$: Calculated: C, 53.26; H, 4.50; N, 4.18; Cl, 17.28. Found: C, 53.40; H, 4.65; N, 4.45; Cl, 17.17.

According to the method of Example 86, the object compounds of Examples 87-89 were synthesized from N-t-butoxycarbonyl-3,5-dichloro-L-tyrosine ethyl ester (Examples 87 and 88) or 3,5-dichloro-N-trifluoroacetyl-L-tyrosine methyl ester (Example 89) via corresponding intermediates, respectively.

EXAMPLE 87

1) m.p.: 165-166° C.; IR (Nujol): 1740, 1731, 1682, 1649, 1630, 1603 cm$^{-1}$; APCI-MS m/z: 670 [M+H]$^+$.

2) m.p.: 222.5-224° C. (dec.); IR (Nujol): 3441, 1739, 1625 cm$^{-1}$; $^1$H-NMR (DMSO-d$_6$): δ 2.96 (1H, dd, J=6.5, 14 Hz), 3.07 (1H, dd, J=6.0, 14 Hz), 3.73 (3H, s), 4.18 (1H, t, J=6.5 Hz), 5.42 (2H, s), 7.28 (2H, s), 7.54-7.65 (4H, m), 7.67-7.72 (2H, m), 8.04 (1H, dd, J=1.5, 7.5 Hz), 8.14 (1H, dd, J=1.5, 8.0 Hz), 8.36 (1H, br); ESI-MS m/z: 540 [M−H]⁻. Elemental analysis for $C_{27}H_{21}Cl_2NO_7 \cdot HCl \cdot H_2O$: Calculated: C, 54.33; H, 4.05; N, 2.35; Cl, 17.82. Found: C, 54.33; H, 3.78; N, 2.52; Cl, 18.07.

EXAMPLE 88

1) Colorless powder; IR (Nujol): 1736, 1715, 1645, 1625, 1603 cm⁻¹; APCI-MS m/z: 822 [M+H]⁺.

2) m.p.: 214-217° C. (dec.); IR (Nujol): 1727, 1623, 1600 cm⁻¹; ¹H-NMR (DMSO-d₆): δ 2.96 (1H, dd, J=6.0, 14 Hz), 3.06 (1H, dd, J=6.0, 14 Hz), 4.17 (1H, br t), 5.42 (2H, s), 7.27 (2H, s), 7.53-7.63 (4H, m), 7.79 (2H, d, J=7.5 Hz), 8.02 (1H, d, J=7.5. Hz), 8.14 (1H, d, J=8.0 Hz), 7.50-8.50 (3H, br), 12.0-14.0 (1H, br); ESI-MS m/z: 526 [M−H]⁻.

EXAMPLE 89

1) m.p.: 228.5-229.5° C.; IR (Nujol): 1756, 1706, 1646, 1603 cm⁻¹; ESI-MS m/z: 592 [M−H]⁻.

2) m.p.: 225-228° C. (dec.); IR (Nujol): 1634 cm⁻¹; ¹H-NMR (DMSO-d₆+TFA+D₂O): δ 2.98 (1H, dd, J=7.0, 15 Hz), 3.08 (1H, dd, J=6.5, 15 Hz), 4.24 (1H, t, J=6.5 Hz), 5.52 (2H, s), 7.04 (1H, s), 7.32 (2H, s), 7.53-7.63 (4H, m), 7.96-8.03 (3H, m), 8.12 (1H, dd, J=2.0, 8.0 Hz).

EXAMPLE 90

1) 60% Sodium hydride (20 mg, 0.495 mmol) was added to a solution of N-t-butoxycarbonyl-3,5-dimethyl-L-tyrosine methyl ester (160 mg, 0.495 mmol) in dimethyl sulfoxide (2 ml) at 18° C. and the mixture was stirred at the same temperature for 30 minutes. To the mixture was added dropwise a solution of 7-chloromethyl-2-phenylbenzoxazole (241 mg, 0.990 mmol) in dimethyl sulfoxide (3 ml) and the mixture was stirred at room temperature for 90 minutes. The reaction mixture was poured into a mixture of ice water and ethyl acetate and then extracted with ethyl acetate. The extract was washed with water and saturated saline solution in turn and dried. The solvent was distilled off under reduced pressure. The residue was purified by column chromatography on silica gel (n-hexane/ethyl acetate=4) to give N-t-butoxycarbonyl-3,5-dimethyl-O-[(2-phenyl)benzoxazol-7-yl]methyl-L-tyrosine methyl ester (185 mg, 70%) as colorless crystals.

m.p.: 116-117° C.; IR (Nujol): 3355, 1759, 1691 cm⁻¹; APCI-MS m/z: 531 [M+H]⁺.

2) Protecting groups of N-t-butoxycarbonyl-3,5-dimethyl-O-[(2-phenyl)benzoxazol-7-yl]methyl-L-tyrosine methyl ester were removed by a conventional method to give the object compound of Example 90.

m.p.: 203-210° C. (dec.); IR (Nujol): 3450(br), 1595, 1552 cm⁻¹; ¹H-NMR (DMSO-d₆+TFA+D₂O): δ 2.33 (6H, s), 2.99 (1H, dd, J=6.6, 14 Hz), 3.04 (1H, dd, J=6.2, 14 Hz), 4.17 (1H, t-like), 5.15 (2H, s), 6.98 (2H, s), 7.48 (1H, dd, J=7.7, 7.7 Hz), 7.58 (1H, br d), 7.63-7.69 (3H, m), 7.85 (1H, dd, J=1.1, 7.7 Hz), 8.18-8.22 (2H, m); ESI-MS m/z: 417 [M+H]⁺. Elemental analysis for $C_{23}H_{24}N_2O_4 \cdot 0.8H_2O$: Calculated: C, 69.69; H, 5.99; N, 6.50. Found: C, 69.63; H, 5.73; N, 6.31.

EXAMPLE 91

1) A mixture of 4-amino-3,5-dichloro-N-trifluoroacetyl-L-phenylalanine ethyl ester (6.0 g, 16.0 mmol) and 8-chloromethyl-3-methylflavone (5.35 g, 18.8 mmol) was stirred at 110° C. for 19 hrs. The reaction mixture was cooled to room temperature, diluted with ethyl acetate, washed with saturated sodium bicarbonate solution, water and saturated saline solution in turn and then dried. The solvent was distilled off under reduced pressure. The residue was purified by column chromatography on silica gel (n-hexane/ethyl acetate=3) to give 3,5-dichloro-4-[(3-methylflavon-8-yl)methyl]amino-N-trifluoro-acetyl-L-phenylalanine ethyl ester (2.9 g, 29%) as colorless crystals.

m.p.: 140-141° C.; IR (Nujol): 3261, 1716, 1623 cm⁻¹; ESI-MS m/z: 619 [M−H]⁻.

2) 3 5-Dichloro-4-[(3-methylflavon-8-yl)methyl]amino-N-trifluoroacetyl-L-phenylalanine ethyl ester was hydrolyzed in a similar manner to Example 6-2) to give the object compound of Example 91.

m.p.: 207-210° C. (dec.); IR (Nujol): 1621, 1598 cm⁻¹; ESI-MS m/z: 495 [M−H]⁻. Elemental analysis for $C_{26}H_{22}Cl_2N_2O_4 \cdot 0.6H_2O$: Calculated: C, 61.45; H, 4.60; N, 5.51; Cl, 13.95. Found: C, 61.44; H, 4.55; N, 5.41; Cl, 13.83.

EXAMPLE 92

The object compound of Example 91 was esterified by a conventional method to give the object compound of Example 92.

m.p.: 186-190° C. (dec.); IR (Nujol): 1741, 1632 cm⁻¹; APCI-MS m/z: 525 [M+H]⁺. Elemental analysis for $C_{28}H_{26}Cl_2N_2O_4 \cdot HCl \cdot 0.8H_2O$: Calculated: C, 58.36; H, 5.00; N, 4.86; Cl, 18.46. Found: C, 58.42; H, 4.98; N, 4.80; Cl, 18.64.

EXAMPLE 93

According to the method of Example 49, the object compound of Example 93 was synthesized from N-trifluoroacetyl-3-hydroxy-L-phenylalanine ethyl ester. Physical data of the intermediate and object compound are shown in the following.

1) m.p.: 109.5-110.5° C.; IR (Nujol): 3321, 1746, 1707, 1560 cm⁻¹; ESI-MS m/z: 456 [M−H]⁻.

2) m.p.: 214-217° C. (dec.); IR (Nujol): 1567, 1555 cm⁻¹; ¹H-NMR (DMSO-d₆+TFA+D₂O): δ 3.15 (2H, br d), 4.22 (1H, t, J=6.4 Hz), 6.98-7.15 (5H, m), 7.33-7.51 (4H, m), 7.64-7.72 (4H, m); ESI-MS m/z: 332 [M−H]⁻. Elemental analysis for $C_{21}H_{19}NO_3 \cdot 0.25H_2O$: Calculated: C, 74.65; H, 5.82; N, 4.15. Found: C, 74.63; H, 5.70; N, 3.98.

EXAMPLE 94

1) 3-[5-Bis[2-(benzyloxy)ethyl]amino-naphth-2-yl]-N-trifluoroacetyl-L-phenylalanine ethyl ester was synthesized in a similar manner to Example 49 from N-trifluoroacetyl-3-hydroxy-L-phenylalanine ethyl ester and 5-bis[2-(benzyloxy)ethyl]amino-2-naphthaleneboronic acid.

Yellow oil; IR (Neat) 3330, 1725, 1715, 1600 cm⁻¹; APCI-MS m/z:715 [M+H]⁺.

2) Ethanol (10 ml), formic acid (1.94 ml, 52 mmol) and 20% palladium hydroxide (145 mg) were added to 3-[5-bis [2-(benzyloxy)ethyl]amino-naphth-2-yl]-N-trifluoroacetyl-L-phenylalanine ethyl ester (739 mg, 1.03 mmol) and the mixture was heated under reflux for 3 days. After the mixture was cooled to room temperature, the catalyst was filtered off and the solvent of the filtrate was distilled off under reduced pressure. The residue was purified by column chromatography on silica gel (ethyl acetate/chloroform=1 and 2) to give 3-[5-bis[2-(hydroxy)ethyl]amino-naphth-2-yl]-N-trifluoroacetyl-L-phenylalanine ethyl ester (395 mg, 71%) as a dark yellow foam.

IR (CHCl$_3$) 3310, 1720 cm$^{-1}$; ESI-MS m/z: 535 [M+H]$^+$.

3) 3-[5-Bis[2-(hydroxy)ethyl]amino-naphth-2-yl]-N-trifluoroacetyl-L-phenylalanine ethyl ester was hydrolyzed in a similar manner to Example 49-2) to give the object compound of Example 94.

m.p.: 181-185° C. (dec.); IR (Nujol): 3350, 3200, 1630, 1600, 1575 cm$^{-1}$; $^1$H-NMR (DMSO-d$_6$): δ 2.89 (1H, dd, J=7.5, 15 Hz), 3.13 (1H, dd, J=4.4, 15 Hz), 3.47-3.63 (9H, m), 6.80-6.85 (1H, m), 6.92-7.05 (3H, m), 7.07-7.20 (2H, m), 7.24-7.32 (2H, m), 7.58-7.67 (2H, m); ESI-MS m/z: 411 [M+H]$^+$. Elemental analysis for C$_{23}$H$_{26}$N$_2$O$_5$.0.3HCl.0.04TFA.1.5H$_2$O: Calculated: C, 61.20; H, 6.53; N, 6.18; Cl, 2.35; F, 0.50. Found: C, 61.44; H, 6.26; N, 5.87; Cl, 2.19; F, 0.49.

EXAMPLE 95

1) A solution of mesyl chloride (172 mg, 1.50 mmol) in methylene chloride (1 ml) was added to a solution of 3-[5-bis[2-(hydroxy)ethyl]amino-naphth-2-yl]-N-trifluoroacetyl-L-phenylalanine ethyl ester (268 mg, 0.50 mmol) in methylene chloride (9 ml) and the mixture was stirred at room temperature for 3 hrs. To the mixture was added water and the mixture was extracted with methylene chloride. The extract was washed with water and dried. The solvent was distilled off under reduced pressure. To the residue were added methanol (10 ml) and lithium chloride (638 mg, 15 mmol) and the mixture was stirred at room temperature for 1 hr. and heated under reflux for 5 hrs. After the mixture was cooled to room temperature, silica gel (3 g) was added thereto and the solvent was distilled off under reduced pressure. The residue was purified by column chromatography on silica gel (n-hexane/ethyl acetate=5) to give 3-[5-bis[2-(chloro)ethyl]amino-naphth-2-yl]-N-trifluoroacetyl-L-phenylalanine ethyl ester (207 mg, 72%) as a pale yellow oil.

IR (Neat) 3400, 3330, 1740, 1730, 1715, 1640, 1600 cm$^{-1}$; ESI-MS m/z: 569 [M−H]$^-$ 2) 3-[5-Bis[2-(chloro)ethyl]amino-naphth-2-yl]-N-trifluoroacetyl-L-phenylalanine ethyl ester was hydrolyzed in a similar manner to Example 49-2) to give the object compound of Example 95.

m.p.: 177-180° C.; IR (Nujol): 3400, 1635, 1600, 1580 cm$^{-1}$; $^1$H-NMR (DMSO-d$_6$): δ 2.85 (1H, dd, J=8.2, 14 Hz), 3.13 (1H, dd, J=4.6, 14 Hz), 3.44 (1H, dd, J=4.6, 8.2 Hz), 3.75-3.87 (8H, m), 6.81-6.86 (1H, m), 6.96-6.99 (1H, m), 7.01-7.09 (2H, m), 7.15 (1H, dd, J=2.6, 8.8 Hz), 7.21 (1H, dd, J=2.4, 9.1 Hz), 7.25-7.33 (2H, m), 7.69 (1H, d, J=9.1 Hz), 7.73 (1H, d, J=9.1 Hz); ESI-MS m/z: 447 [M+H]$^+$. Elemental analysis for C$_{23}$H$_{24}$Cl$_2$N$_2$O$_3$.H$_2$O: Calculated: C, 59.36; H, 5.63; N, 6.02; Cl, 15.24. Found: C, 59.16; H, 5.42; N, 5.88; Cl, 15.55.

EXAMPLE 96

1) According to the method of Example 49-1), from N-trifluoroacetyl-3-hydroxy-L-phenylalanine ethyl ester (1.47 g, 4.82 mmol) as the starting material was obtained 3-(3-bromophenoxy)-N-trifluoroacetyl-L-phenylalanine ethyl ester (1.59 g, 82%) as a colorless oil.

IR (Neat) 3322, 1715, 1579 cm$^{-1}$; ESI-MS m/z: 458/460 [M−H]$^-$.

A solution of 4-(tributylstannyl)pyridine (288 mg, 0.782 mmol) in degassed 1,4-dioxane (1 ml) and tetrakis(triphenyl-phosphine)palladium (46 mg, 0.04 mmol) were added in turn to a solution of 3-(3-bromophenoxy)-N-trifluoroacetyl-L-phenylalanine ethyl ester (360 mg, 0.782 mmol) in degassed 1,4-dioxane (6 ml) at room temperature and the mixture was stirred under heating for 8 hrs. After the mixture was cooled to room temperature, ethyl acetate was added thereto and the mixture was washed with saturated sodium fluoride solution, water and brine in turn and then dried. The solvent was distilled off under reduced pressure. The residue was purified by column chromatography on silica gel (n-hexane/ethyl acetate=1) to give N-trifluoroacetyl-3-[3-(4-pyridyl)phenoxy]-L-phenylalanine ethyl ester (235 mg, 66%) as colorless resinous substance.

IR (Neat+CHCl$_3$) 1741, 1720 cm$^{-1}$; ESI-MS m/z: 457 [M−H]$^-$.

2) N-Trifluoroacetyl-3-[3-(4-pyridyl)phenoxy]-L-phenylalanine ethyl ester was hydrolyzed in a similar manner to Example 49-2) to give the object compound of Example 96.

m.p.: 182-185° C. (dec.); IR (Nujol): 3406, 1617, 1596, 1577, 1547 cm$^{-1}$; $^1$H-NMR (DMSO-d$_6$): δ 2.87 (1H, dd, J=8.1, 14 Hz), 3.14 (1H, dd, J=4.4, 14 Hz), 3.39 (1H, dd, J=4.4, 8.1 Hz), 6.89-6.93 (1H, m), 7.02-7.13(3H, m), 7.32 (1H, dd, J=7.9, 7.9 Hz), 7.43-7.58 (3H, m), 7.69-7.72 (2H, m), 8.60-8.63 (2H, m); APCI-MS m/z: 335 [M+H]$^+$. Elemental analysis for C$_{20}$H$_{18}$N$_2$O$_3$.0.7H$_2$O: Calculated: C, 69.23; H, 5.64; N, 8.07. Found: C, 69.29; H, 5.79; N, 7.87.

The object compounds of the following Example 97, Examples 99-103 and Examples 105-108 were synthesized according the method of Example 96 from 3-(3-bromophenoxy)-N-trifluoro-acetyl-L-phenylalanine ethyl ester via each corresponding intermediate. In Examples 97, 101 and 106, corresponding boronic acid was used instead of the tin compound, sodium acetate was used as a base and aqueous dimethoxyethane was used as a solvent.

EXAMPLE 97

1) Colorless resinous substance; IR (Neat+CHCl$_3$) 3321, 2983, 1717, 1605 cm$^{-1}$; ESI-MS m/z: 500 [M−H]$^-$.

2) m.p.: 214-218° C. (dec.); IR (Nujol): 3627, 1611, 1575, 1524 cm$^{-1}$; $^1$H-NMR (DMSO-d$_6$+TFA+D$_2$O): δ 3.14 (2H, d, J=6.6 Hz), 3.27 (6H, s), 4.21 (1H, t, J=6.6 Hz), 6.97-7.11 (4H, m), 7.32-7.55 (5H, m), 8.22 (1H, br d), 8.34 (1H, dd, J=2.4, 9.7 Hz); ESI-MS m/z: 378 [M+H]$^+$. Elemental analysis for C$_{22}$H$_{23}$N$_3$O$_3$.H$_2$O: Calculated: C, 66.82; H, 6.37; N, 10.63. Found: C, 66.77; H, 6.39; N, 10.51.

EXAMPLE 98

The hydrochloride of the object compound of Example 97 was synthesized by a conventional method.

m.p.: 223-228° C. (dec.); IR (Nujol): 3373, 1734 cm$^{-1}$; ESI-MS m/z: 376 [free M−H]$^-$.

EXAMPLE 99

1) Colorless oil; IR (Neat) 3310, 1738, 1722 cm$^{-1}$; ESI-MS m/z: 457[M−H]$^-$.

2) m.p.: 187-192° C. (dec.); IR (Nujol): 3276, 1611, 1585, 1567, 1540 cm$^{-1}$; $^1$H-NMR (DMSO-d$_6$+D$_2$O): δ 2.89 (1H, dd, J=8.4, 14 Hz), 3.17 (1H, dd, J=4.2, 14 Hz), 3.50 (1H, dd, J=4.2, 8.4 Hz), 6.84-6.93 (1H, m), 7.04-7.07 (1H, m), 7.09-7.14 (2H, m), 7.32-7.40 (2H, m), 7.52 (1H, dd, J=8.0, 8.0 Hz), 7.11 (1H, t-like), 7.80-7.97 (3H, m), 8.63-8.65 (1H, m); ESI-MS m/z: 335 [M+H]$^+$. Elemental analysis for C$_{20}$H$_{18}$N$_2$O$_3$.0.1H$_2$O: Calculated: C, 71.46; H, 5.46; N, 8.33. Found: C, 71.39; H, 5.43; N, 8.08.

EXAMPLE 100

1) Colorless oil; IR (Neat) 3319, 1739, 1722, 1715 cm$^{-1}$; ESI-MS m/z: 457 [M−H]$^−$.

2) m.p.: 200-204° C. (dec.); IR (Nujol): 3417, 1661, 1580 cm$^{-1}$; $^1$H-NMR (DMSO-d$_6$+TFA+D$_2$O): δ 3.07-3.19 (2H, m), 4.23 (1H, t-like), 6.99-7.19 (4H, m), 7.41 (1H, dd, J=7.8, 7.8 Hz), 7.55-7.66 (3H, m), 8.08 (1H, dd, J=5.7, 8.4 Hz), 8.80-8.89 (2H, m), 9.22 (1H,d, J=2.2 Hz); ESI-MS m/z: 335 [M+H]$^+$. Elemental analysis for C$_{20}$H$_{18}$N$_2$O$_3$.0.95H$_2$O: Calculated: C, 68.34; H, 5.71; N, 7.97. Found: C, 68.64; H, 5.51; N, 7.62.

EXAMPLE 101

1) Colorless oil; IR (Neat) 3321, 1721 cm$^{-1}$; ESI-MS m/z: 514 [M−H]$^−$.

2) m.p.: 227-230° C. (dec.); IR (Nujol): 3416, 1681, 1635, 1605, 1581, 1564, 1517 cm$^{-1}$; $^1$H-NMR (DMSO-d$_6$): δ 2.86 (1H, dd, J=8.3, 14 Hz), 3.15 (1H, dd, J=4.6, 14 Hz), 3.43 (1H, dd, J=4.6, 8.3 Hz), 6.88-6.94 (1H, m), 6.93-7.10 (3H, m), 7.32 (1H, dd, J=7.8, 7.8 Hz), 7.36-7.38 (1H, m), 7.46-7.52 (2H, m), 7.76-7.80 (2H, m), 7.97-8.02 (2H, m); ESI-MS m/z: 376 [M−H]$^−$. Elemental analysis for C$_{22}$H$_{19}$NO$_5$.0.7H$_2$O: Calculated: C, 67.75; H, 5.27; N, 3.59. Found: C, 67.77; H, 5.36; N, 3.57.

EXAMPLE 102

1) Colorless oil; IR (Neat) 3324, 1717 cm$^{-1}$; ESI-MS m/z: 490 [M−H]$^−$.

2) m.p.: 193-198° C. (dec.); IR (Nujol): 1593, 1581, 1565, 1521 cm$^{-1}$; $^1$H-NMR (DMSO-d$_6$): δ 2.85 (1H, dd, J=8.4, 14 Hz), 3.14 (1H, dd, J=4.5, 14 Hz), 3.37 (1H, dd, J=4.5, 8.4 Hz), 6.88-6.92 (1H, m), 7.00-7.09 (3H, m), 7.28-7.36 (2H, m), 7.40-7.50 (4H, m), 7.62-7.66 (1H, m), 7.72 (1H, t-like); ESI-MS m/z: 366 [M−H]$^−$. Elemental analysis for C$_{21}$H$_{18}$ClNO$_3$.0.1H$_2$O: Found: C, 68.24; H, 4.96; N, 3.79; Cl, 9.59. Found: C, 68.42; H, 4.78; N, 3.72; Cl, 9.15.

EXAMPLE 103

1) Colorless oil; IR (Neat) 3323, 1716 cm$^{-1}$; ESI-MS m/z: 490 [M−H]$^−$.

2) m.p.: 204-208° C. (dec.); IR (Nujol): 3280, 1585 cm$^{-1}$; $^1$H-NMR (DMSO-d$_6$+TFA+D$_2$O): δ 3.10 (1H, dd, J=6.8, 14 Hz), 3.14 (1H, dd, J=6.2, 14 Hz), 4.23 (1H, t-like), 6.98-7.10 (4H, m), 7.31 (1H, t-like), 7.37-7.54 (5H, m), 7.66-7.71 (2H, m); ESI-MS m/z: 366 [M−H]$^−$. Elemental analysis for C$_{21}$H$_{18}$ClNO$_3$.0.1H$_2$O: Calculated: C, 68.24; H, 4.96; N, 3.79; Cl, 9.59. Found: C, 68.53; H, 4.78; N, 3.92; Cl, 9.39.

EXAMPLE 104

The object compound of Example 103 was esterified by a conventional method.

m.p.: 160-162° C.; IR (Nujol): 1746 cm$^{-1}$; APCI-MS m/z: 396 [M+H]$^+$. Elemental analysis for C$_{23}$H$_{22}$ClNO$_3$.HCl: C, 63.90; H, 5.36; N, 3.24; Cl, 16.40. Found: C, 63.80; H, 5.32; N, 3.29; Cl, 16.24.

EXAMPLE 105

1) m.p.: 73-75° C.; IR (Nujol): 1751, 1706 cm$^{-1}$; ESI-MS m/z: 499 [M−H]$^−$ 2) m.p.: 226-229° C. (dec.); IR (Nujol): 1626, 1612, 1575, 1531 cm$^{-1}$; $^1$H-NMR (DMSO-d$_6$+TFA+D$_2$O): δ 3.06-3.20 (8H, m), 4.12-4.26 (1H with HOD), 6.96-7.10 (4H, m), 7.28-7.31 (1H, m), 7.37-7.51 (5H, m), 7.70-7.77 (2H, m); ESI-MS m/z: 375 [M−H]$^−$. Elemental analysis for C$_{23}$H$_{24}$N$_2$O$_3$.0.9H$_2$O: Calculated: C, 70.35; H, 6.62; N, 7.13. Found: C, 70.39; H, 6.40; N, 7.10.

EXAMPLE 106

1) Colorless resinous substance; IR (Neat+CHCl3) 3320, 1740, 1719 cm$^{-1}$; ESI-MS m/z: 507 [M−H]$^−$.

2) m.p.: 185-190° C. (dec.); IR (Nujol): 1601, 1577 cm$^{-1}$; $^1$H-NMR (DMSO-d$_6$): δ 2.88 (1H, dd, J=8.1, 14 Hz), 3.14 (1H, dd, J=4.8, 14 Hz), 3.41 (1H, dd, J=4.8, 8.1 Hz), 6.92-6.97 (1H, m), 7.06-7.12 (3H, m), 7.33 (1H, dd, J=7.7, 7.7 Hz), 7.52-7.67 (4H, m), 7.74-7.80 (1H, m), 8.01-8.11 (2H, m), 8.74 (1H, d, J=2.2 Hz), 9.24 (1H, d, J=2.4 Hz); ESI-MS m/z: 383 [M−H]$^−$. Elemental analysis for C$_{24}$H$_{20}$N$_2$O$_3$.0.6H$_2$O: Calculated: C, 72.93; H, 5.41; N, 7.10. Found: C, 72.87; H, 5.11; N, 6.88.

EXAMPLE 107

1) Colorless resinous substance; IR (Neat+CHCl$_3$) 3321, 1719, 1602 cm$^{-1}$; ESI-MS m/z: 558 [M−H]$^−$.

2) m.p.: 196-202° C. (dec.); IR (Nujol): 1601, 1575, 1505 cm$^{-1}$; $^1$H-NMR (DMSO-d$_6$): δ 2.58-2.63 (4H, m), 2.84 (1H, dd, J=8.4, 14 Hz), 3.14 (1H, dd, J=4.4, 14 Hz), 3.38 (1H, dd, J=4.4, 8.4 Hz), 3.90-3.97 (4H, m) 6.86-6.94 (3H, m), 7.00-7.08 (2H, m), 7.25-7.44 (4H, m), 7.84 (1H, dd, J=2.6, 9.0 Hz), 8.43 (1H, d, J=2.6 Hz); ESI-MS m/z: 434 [M−H]$^−$. Elemental analysis for C$_{24}$H$_{25}$N$_3$O$_3$S.0.7H$_2$O: Calculated: C, 64.32; H, 5.94; N, 9.38; S, 7.15. Found: C, 64.61; H, 5.73; N, 9.35; S, 6.84.

EXAMPLE 108

1) m.p.: 126.5-127.5° C.; IR (Nujol): 3289, 1741, 1701, 1604, 1579, 1541 cm$^{-1}$; ESI-MS m/z: 501 [M−H]$^−$.

2) m.p.: 191-194° C. (dec.); IR (Nujol): 3380, 1605, 1577, 1533 cm$^{-1}$; $^1$H-NMR (DMSO-d$_6$+TFA+D$_2$O): δ 3.05-3.19 (2H, m), 3.18 (6H, s), 4.22 (1H, t, J=6.4 Hz), 6.94-7.10 (4H, m), 7.30-7.49 (4H, m), 8.70 (2H, s); ESI-MS m/z: 377 [M−H]$^−$. Elemental analysis for C$_{21}$H$_{22}$NO$_3$.0.9H$_2$O: Calculated: C, 63.91; H, 6.08; N, 14.20. Found: C, 64.03; H, 5.83; N, 14.13.

EXAMPLE 109

1) According to the method of Example 49-1), 3-(4-bromophenoxy)-N-t-butoxycarbonyl-L-phenylalanine methyl ester (547 mg, 94%) was obtained as colorless oil from N-t-butoxycarbonyl-3-hydroxy-L-phenylalanine methyl ester (328 mg, 4.82 mmol).

IR (Neat) 3376, 2977, 1745, 1714, 1608, 1577 cm$^{-1}$; APCI-MS m/z: 467 [M+NH$_4$]$^+$, 450 [M+H]$^+$.

Tetrakis(triphenylphosphine)palladium (67 mg, 0.058 mmol) was added to a solution of 3-(4-bromophenpxy)-N-t-butoxycarbonyl-L-phenylalanine methyl ester (262 mg, 0.582 mmol) and 5-(tributylstannyl)-2-(dimethylamino)pyrimidine (264 mg, 0.640 mmol) in degassed 1,4-dioxane (5 ml) at room temperature and the mixture was heated with stirring for 6 hrs. After the mixture was cooled to room temperature, ethyl acetate was added thereto. The mixture was washed with saturated sodium fluoride solution, water and brine in turn and dried. The solvent was distilled off under reduced pressure. The residue was purified by column chromatography on amine silica gel (Chromatolex (trade name) NH) (n-hexane/ethyl acetate=5) to give N-t-butoxy-carbonyl-3-[4-(2-dimethylaminopyrimidin-5-yl)-phenoxy]-L-phenylalanine ethyl ester (121 mg, 42%) as colorless resinous substance.

IR (Neat+CHCl$_3$) 3340, 3375, 1746, 1713, 1601 cm$^{-1}$; APCI-MS m/z: 493 [M+H]$^+$.

2) N-t-Butoxycarbonyl-3-[4-(2-dimethylaminopyrimidin-5-yl)phenoxy]-L-phenylalanine ethyl ester was deprotected by a conventional method to give the object compound of Example 109.

m.p.: 196-200° C. (dec.); IR (Nujol): 1600, 1545, 1527, 1504 cm$^{-1}$; $^1$H-NMR (DMSO-d$_6$+TFA+D$_2$O): δ 3.13 (2H, br d, J=6.4 Hz), 4.21 (1H, t, J=6.4 Hz), 6.95-7.04 (2H, m), 7.06-7.16 (3H, m), 7.40 (1H, dd, J=7.9, 7.9 Hz), 7.66-7.73 (2H, m), 8.77 (2H, s); ESI-MS m/z: 377 [M–H]$^-$. Elemental analysis for C$_{21}$H$_{22}$N$_4$O$_3$.0.8H$_2$O: Calculated: C, 64.21; H, 6.05; N, 14.26. Found: C, 64.01; H, 5.62; N, 14.03.

EXAMPLE 110

According to the method of Example 109, the object compound of Example 110 was synthesized from 3-(4-bromophenoxy)-N-t-butoxycarbonyl-L-phenylalanine methyl ester via corresponding intermediate. Physical data of the intermediate and object compound are shown in the following.

1) Colorless oil; IR (Neat+CHCl$_3$) 3440, 3375, 1745, 1714, 1606, 1586, 1550, 1500 cm$^{-1}$; APCI-MS m/z: 492 [M+H]$^+$.

2) m.p.: 199-201° C. (dec.); IR (Nujol): 1612, 1553, 1502 cm$^{-1}$; $^1$H-NMR (DMSO-d$_6$+TFA+D$_2$O): δ 3.14 (2H, br d), 4.23 (1H, t, J=6.5 Hz), 6.96-7.05 (2H, m), 7.08-7.18 (3H, m), 7.36 (1H, d, J=9.5 Hz), 7.41 (1H, dd, J=8.0, 8.0 Hz), 7.69-7.75 (2H, m), 8.19 (1H, d, J=2.4 Hz), 8.35 (1H, dd, J=2.4, 9.5 Hz); ESI-MS m/z: 376 [M–H]$^-$. Elemental analysis for C$_{22}$H$_{23}$N$_3$O$_3$.0.2H$_2$O: Calculated: C, 69.35; H, 6.19; N, 11.03. Found: C, 69.43; H, 6.20; N, 10.86.

EXAMPLE 111

1) Trifluoromethanesulfonic anhydride (1.51 ml) was added dropwise to an ice-cold solution of N-trifluoroacetyl-3-hydroxy-L-phenylalanine ethyl ester (915 mg, 3.00 mmol) in pyridine (9 ml) in 5 minutes under argon atmosphere. The mixture was stirred at the same temperature for 30 minutes and then at room temperature for 16 hrs. The reaction mixture was poured into ice-water (500 ml) and extracted with ethyl acetate. The extract was washed with 10% hydrochloric acid, water and brine in turn and then dried. The solvent was distilled off under reduced pressure. The residue was purified by column chromatography on silica gel (n-hexane/ethyl acetate=7) to give N-trifluoroacetyl-3-trifluoromethanesulfonyloxy-L-phenylalanine ethyl ester (1.25 g, 95%) as pale yellow crystals.

m.p.: 38-39° C.; IR (Nujol): 3313, 1739, 1707, 1557 cm$^{-1}$; ESI-MS m/z: 436 [M–H]$^-$.

2-Naphthaleneboronic acid (142 mg, 0.824 mmol), tetrakis(triphenylphosphine)palladium (80 mg, 0.069 mmol) and potassium phosphate (120 mg, 0.563 mmol) were added in turn to a solution of N-trifluoroacetyl-3-trifluoromethanesulfonyloxy-L-phenylalanine ethyl ester (300 mg, 0.686 mmol) in degassed dimetoxyethane (2 ml). The mixture was stirred under argon atmosphere at 85° C. for 3 hrs. After being cooled to room temperature, the reaction mixture was diluted with ethyl acetate and water and then extracted with ethyl acetate. The extract was washed with water and brine in turn and dried. The solvent was distilled off under reduced pressure. The residue was purified by column chromatography on silica gel (n-hexane/ethyl acetate=9) to give N-trifluoroacetyl-3-(2-naphthyl)-L-phenylalanine ethyl ester (173 mg, 61%) as colorless crystals.

m.p.: 89-91° C.; IR (Nujol): 3294, 1737, 1701 cm$^{-1}$; ESI-MS m/z: 414 [M–H]$^-$ 2) N-Trifluoroacetyl-3-(2-naphthyl)-L-phenylalanine ethyl ester was hydrolyzed in a similar manner to Example 49-2) to give the object compound of Example 111.

m.p.: 220-224° C. (dec.); IR (Nujol): 3397, 1509 cm$^{-1}$; ESI-MS m/z: 290 [M–H]$^-$. Elemental analysis for C$_{19}$H$_{17}$NO$_2$.0.5H$_2$O: Calculated: C, 75.98; H, 6.04; N, 4.66. Found: C, 76.01; H, 5.99; N, 4.66.

EXAMPLE 112

According to the method of Example 111, the object compound of Example 112 was synthesized from N-trifluoroacetyl-3-trifluoromethanesulfonyloxy-L-phenylalanine ethyl ester via corresponding intermediate. Physical data of the intermediate and object compound are shown in the following.

1) Colorless oil; IR (Neat) 3325, 1738, 1699, 1597, 1573, 1555 cm$^{-1}$; ESI-MS m/z: 440 [M–H]$^-$.

2) m.p.: 199-201° C. (dec.); IR (Nujol): 3375, 1596, 1543 cm$^{-1}$; $^1$H-NMR (DMSO-d$_6$): δ 2.95 (1H, dd, J=8.4, 14 Hz), 3.25 (1H, dd, J=4.2, 14 Hz), 3.49 (1H, dd, J=4.2, 8.4 Hz), 7.29 (1H, br d), 7.36-7.78 (11H, m), 7.91 (1H, m); ESI-MS m/z: 316 [M–H]$^-$. Elemental analysis for C$_{21}$H$_{19}$NO$_2$.1.2H$_2$O: Calculated: C, 74.40; H, 6.36; N, 4.13. Found: C, 74.43; H, 6.19; N, 4.17.

TEST EXAMPLE 1

1) To each of the weighed test compounds, DMSO was added to prepare a 100 mM solution or suspension as a DMSO stock. In an assay, the stock was diluted 1,000 fold with a buffer described below. The final concentration of the test compound was 100 μM and the final concentration of DMSO was 0.1%.

2) The LAT1 inhibiting activity of the test compound was determined in the following manner. Using human bladder cancer cell strain T24 cells, in which LAT1 only was strongly expressed, inhibiting activity of each test compound against "$^{14}$C"-L-leucine uptake was determined as the LAT1 inhibiting activity.

T24 cells in a logarithmic growth-phase were transferred to a 24-well plate at 0.8×10$^5$ cell/well and cultured at 37° C. for 2 days. After the plate was incubated at 37° C. on a water bath for 5 minutes, the fixed cells were washed three times with a Hank's balanced salt solution (HBSS: 25 mM HEPES, 125 mM choline chloride, 5.6 mM glucose, 4.8 mM KCl, 1.2 mM MgSO$_4$, 1.2 mM KH$_2$PO$_4$, 1.3 mM CaCl$_2$, pH 7.4) warmed to 37° C., not containing Na$^+$, to which 500 μl of HBSS (37° C.) was added. Then, further incubation was carried out for 7 minutes.

After the incubation was finished, a supernatant was replaced with HBSS containing 1 μM $^{14}$C-Leu and 100 μM test compound (37° C.), followed by 1-minute uptake. Then, the cells were washed three times with HBSS of 4° C. The washed cells were added with 500 μl of 0.1 N NaOH to dissolve the cells for 20 minutes. The cell solution was transferred to a vial, to which 3 ml of a scintillator was added to measure the radioactivity with a liquid scintillation counter.

Inhibition % was calculated by the following formula.

Inhibition %=100−(radioactivity of the well added with the test compound)/(radioactivity of the well not added with the test compound)×100

Table 14 shows the $IC_{50}$ values obtained by this formula.

TABLE 14

| Ex. No. | $IC_{50}$ |
|---|---|
| 6-2) | 0.3 |
| 22 | 0.2 |
| 30 | 0.3 |
| 32 | 0.24 |
| 33 | 0.15 |
| 34 | 0.29 |
| 35 | 0.28 |
| 36 | 0.2 |
| 37 | 0.13 |
| 38 | 0.33 |
| 39 | 0.23 |
| 48 | 0.3 |
| 49-2) | 0.1 |
| 52 | 0.5 |
| 53 | 0.12 |
| 54 | 0.71 |
| 55 | 0.29 |
| 56 | 0.26 |
| 58 | 0.49 |
| 63 | 0.94 |
| 65 | 0.33 |
| 70 | 0.29 |
| 71 | 0.37 |
| 72 | 0.36 |
| 73 | 0.11 |
| 74 | 0.95 |
| 81 | 0.20 |
| 83 | 0.55 |
| 85 | 0.27 |
| 87 | 0.23 |
| 89 | 0.38 |
| 90 | 0.11 |
| 91 | 0.10 |
| 93 | 0.17 |
| 96 | 0.84 |
| 97 | 0.01 |
| 98 | 0.20 |
| 99 | 0.52 |
| 100 | 0.22 |
| 102 | 0.06 |
| 103 | 0.06 |
| 106 | 0.83 |
| 108 | 0.67 |
| 112 | 0.81 |
| Control (BCH) | 100 |

TEST EXAMPLE 2

(Preparation of Specimen)

Each of the weighed test compounds (Examples 6-2), 9, 15, 17 and 49-2)) was added with DMSO to prepare a 100 mM solution or suspension as a DMSO stock. In an assay, the stock was diluted with DMSO to prepare a solution of 1,000-fold concentration of the final concentration of each test compound. A 100-fold dilution of each solution in a culture medium was added thereto in an amount of one tenth of the whole amount.

(Assessment of Inhibition of T24 Cell Proliferation)

T24 cells in a logarithmic growth phase were prepared in $1\times10^3$ cells/ml, which were transferred to a 24-well plate by 900 ml and left stand at 37° C. for 6 hours. After the cells were fixed, a dilution of the test compound in a culture medium having a concentration 10 times higher than the final concentration was added to each well by 100 ml and cultured at 37° C. for 5 days. The wells not added with the test compound were added with a culture medium containing 0.1% DMSO. After 5 days, the cells in the wells were peeled by trypsin/EDTA treatment, collected by centrifugation at 1500 rpm for 5 minutes and suspended in a small amount of a culture medium, which were counted on a blood cell counting chamber.

Inhibition % was calculated by the following formula.

Inhibition %=100−(cell count in the well added with the test compound)/(cell count in the well not added with the test compound)×100

FIGS. 1 to 5 show the results.

TEST EXAMPLE 3

In an inguinal region of ICR mice, $1\times10^6$ sarcoma 180 cells were implanted subcutaneously. After 24 hours from the implantation, administration of the test compounds (Example 6-3) and Example 49-3)) was started, which was continued intravenously for 7 days.

Each of the test compounds was dissolved in a physiologic saline containing 10% DMSO and 10% Tween 80 so that the amount of the test compound became 100 mg/kg, which was intravenously administered in an amount of 0.1 ml per 10 g of body weight. After 10 days from the implantation, tumor weight was measured and a proliferation inhibiting rate was calculated by the following formula to be compared with that of nontreated controls.

Proliferation inhibiting rate (T/C)=[1−(average tumor weight of the group added with the test compound/average tumor weight of the control group)]×100

As a result, the test compounds of Example 6-3) and Example 49-3), 100 mg/kg each, showed the proliferation inhibiting rate of 52.2% and 41.3%, respectively.

TEST EXAMPLE 4

To nude mice, $1\times10^6$ T24 cells were subcutaneously vaccinated to form a subcutaneous tumor. After 5 days from the vaccination, administration of the test compound (Example 49-2)) was started, which was continued for 10 days.

The test compound was dissolved to be 2.577 mM in a physiologic saline (containing 2% DMSO), 0.1 ml of which was injected into the tumor twice a day (morning and evening). As a control, a physiologic saline (containing 2% DMSO) was administered in a like manner. Before the morning and evening administration, the tumor diameter was measured.

Figure 6:
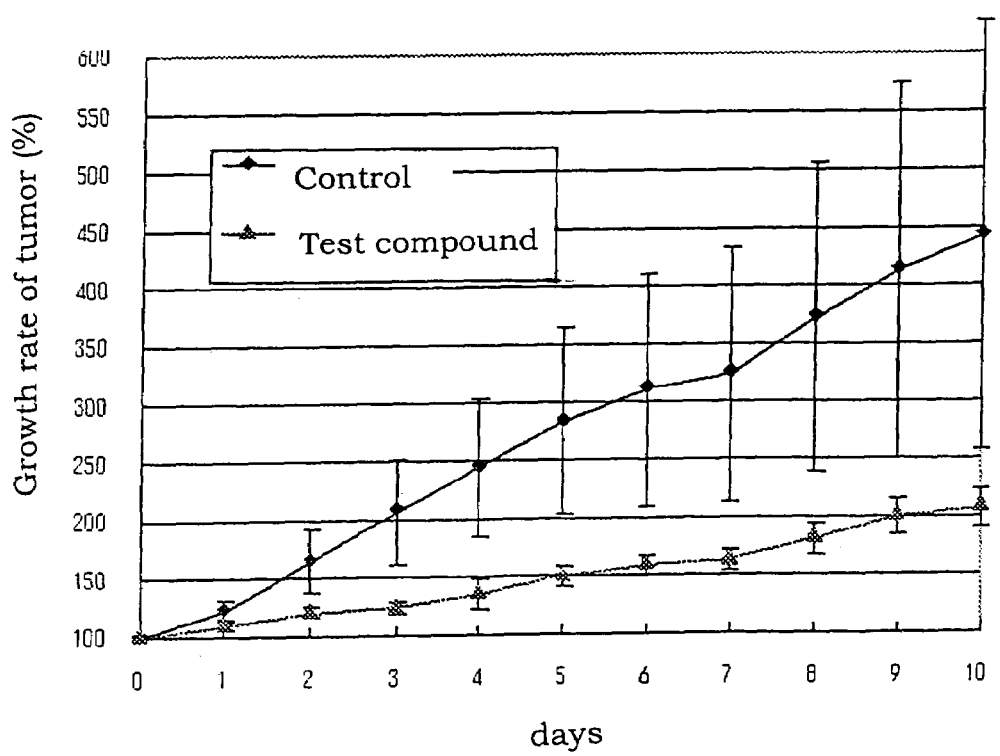
FIG. 6 is a graph showing an in-vivo activity inhibiting multiplication of cancer cells by an aromatic amino acid derivative (Example 49) of the present invention.

FIG. 6 shows the results.

TEST EXAMPLE 5

Analysis of LAT1/LAT2 Selectivity

1) First, human LAT1 (hereinafter referred to as hLAT1), human LAT2 (hereinafter referred to as hLAT2) and human 4F2hc (hereinafter referred to as h4F2hc) were linearized by restriction enzyme treatment. After ethanol precipitation, they were dissolved in a DEPC treatment solution to prepare a mold cDNA. Then, in vitro transcription reaction was carried out in the following manner.

Reaction composition (50 μl in total)

Mold cDNA 1.5 μg

RNasin RNase inhibitor (Promega) 100 U rNTP (Amersham. Pharmacia) 10 mM each (rGTP was 1 mM)
DTT 30 mM
m7G(5')ppp(5')G (Amersham. Pharmacia) 0.5 U
RNA polymerase (Stratagene) 50 U
Transcription buffer As the RNA polymerase for hLAT1, hLAT2 and h4F2hc, T3, SP6 and T7 were used, respectively.

After the above reagents were mixed, they were reacted at 37° C. for 10 minutes, added with 1 µL of 5 mM rGTP, and reacted again at 37° C. for 10 minutes. Further, 1 µL of 5 mM rGTP was added and the reaction was carried out again at 37° C. for 10 minutes. Then, RNase-free DNase (Stratagene) was added and mixed, followed by incubation at 37° C. for 20 minutes. The reaction solution was sequentially extracted with phenol/chloroform, and then with chloroform. Then, half amount of 7.5 M $NH_4OAc$ and 2.5-fold amount of cold ethanol were added to perform ethanol precipitation. After centrifugation at 15000 rpm for 30 minutes, the resulting precipitate was washed with cold 80% ethanol and dissolved in 100 µL of a DEPC treatment solution. Thereafter, ethanol precipitation was performed again. The precipitate obtained by centrifugation at 15000 rpm for 30 minutes was washed with cold 80% ethanol and dried for 20 minutes in a centrifugal concentrator. Then, it was dissolved in a DEPC treatment solution to 0.5 mg/mL to prepare a cRNA solution. Thus, cRNA was prepared by in vitro transcription reaction.

2) *Xenopus laevis* was anesthetized by immersing into an anesthetic solution (0.2% MS-222, 0.3% $KHCO_3$), and then cut open in the abdominal region on ice to take out an oocyte mass under the peritoneum. The extracted oocyte mass was shredded with tweezers, which was added to an OR2 culture medium (5 mM HEPES, 82.5 mM NaCl, 2 mM KCl, 1 mM $MgCl_2$, pH 7.5) containing 2 mg/mL of collagenase, incubated at room temperature for about 30 minutes, washed with the OR2 culture medium and transferred into a Barth culture medium (10 mM HEPES, 88 mM NaCl, 1 mM KCl, 0.33 mM $Ca(NO_3)_2$, 0.41 mM $CaCl_2$, 0.82 mM $MgSO_4$, 2.4 mM $NaHCO_3$, pH 7.4).

Then, a follicular cell layer covering the oocytes was peeled under a stereoscopic microscope to isolate the oocytes, to which 50 nL of a cRNA solution was added, respectively. As the cRNA, an equimolar mixture of hLAT1 cRNA and h4F2hc cRNA was injected into the oocytes for hLAT1 expression, and an equimolar mixture of hLAT2 cRNA and h4F2hc cRNA was injected into the oocytes for hLAT2 expression.

The control cell was injected with distilled water.

3) The oocytes after the injection were cultured in a Barth culture medium containing gentamicin for 2 days, from which healthy oocytes were selected and transferred to a 24-well plate at 8-10 cell/well.

First, after washing twice with choline 100 (5 mM HEPES, 100 mM choline Cl, 2 mM KCl, 1.8 mM $CaCl_2$, 1 mM $MgCl_2$, pH 7.4) at room temperature, choline 100 containing 10 µM $^{14}C$-Leu and specimens of various concentrations was added for an uptake for 30 minutes. Then, after washing with choline 100 of 4° C. six times, the oocytes were transferred to vials one by one and 250 µL of 10% SDS was added thereto, which was shaken at room temperature for an hour to be dissolved. After an hour, the solution was added with 3 mL of a scintillator to measure the radioactivity using a liquid scintillation counter. Inhibition rate was calculated by the following formula using an average value of 8 to 10 cells.

Inhibition rate (%)=100−(radioactivity of the well added with the test compound)/(radioactivity of the well not added with the test compound)×100

Based on this rate, the $IC_{50}$ value was calculated and the selectivity was obtained in the following manner.

Selectivity (times)=($IC_{50}$ for inhibition of leucine uptake into hLAT2 expressing cells)/($IC_{50}$ for inhibition of leucine uptake into hLAT1 expressing cells)

Table 15 shows the results.

TABLE 15

| Ex. No. | $IC_{50}$ of LAT1 | $IC_{50}$ of LAT2 | Selectivity (L2/L1) |
|---------|-------------------|-------------------|---------------------|
| 6-2     | 0.1               | 100               | 1000                |
| 9       | 0.7               | 69                | 100                 |
| 15      | <1                | >100              | 100                 |
| 17      | <1                | >100              | 100                 |
| 23      | <1                | >100              | 100                 |
| 57      | 10                | 0.2               | 0.02                |
| 59      | 10                | <1                | 0.1                 |
| 60      | 10                | <1                | 0.1                 |

TEST EXAMPLE 6

Toxicological Test

Compounds of Example 6-3) and Example 49-3) were intravenously and orally administered to groups of Slc: ddY male mice (four week old) consisting of five individuals each.

For the intravenous administration, each of the above compounds was dissolved in physiologic saline containing 10% DMSO and 10% Tween 80 and administered in an amount of 10 mg/kg. A control group was administered with the solvent only.

For the oral administration, each of the above compounds was suspended in distilled water and administered in an amount of 1,000 mg/kg. A control group was administered with the solvent only.

Both of the compounds did not show a special symptom change through the intravenous and oral administration during the observation period.

Further, with respect to the compounds of Examples 77-79 and Example 98, an acute toxicity test for intravenous administration of mice were carried out to obtain $LD_{50}$. The compound of Example 77 showed 69.3 mg/kg, and the other compounds showed 100 mg/kg or more, respectively. As a control, BCH tested in the same manner showed $LD_{50}$ of 300 mg/kg or more.

The invention claimed is:

1. An aromatic amino acid derivative represented by formula (I) or its pharmacologically acceptable salt:

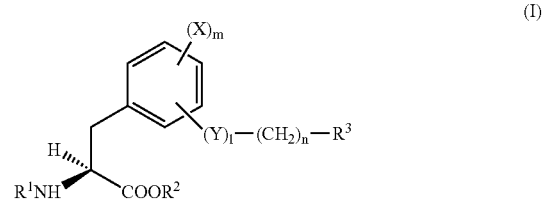

wherein,
X is a halogen atom, an alkyl group or alkoxy group,
Y is O or NH,
l in (Y)$_l$ is 0 or 1,
m is 0, 1 or 2,
n is an integer of 0-5,
R$^1$ is a hydrogen atom or an amino-protecting group,
R$^2$ is a hydrogen atom or an alkyl, aralkyl or aryl group,
R$^3$ is a condensed heterocyclic group selected from the group consisting of benzofuran, benzoxazole, benzoimidazole, benzopyrrole and benzothiazole, wherein said R$^3$ group is attached to the (Y)$_l$—(CH$_2$)$_n$— moiety through the benzo moiety thereof, and wherein said condensed heterocyclic group is optionally substituted with oxo, carboxy, amino, lower alkyl, lower alkoxy, cycloalkyl, di(lower)alkylamino, lower alkoxycarbonyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino, lower alkanoyloxy, bis[halo(lower)alkyl]amino or N-(lower)alkyl-N-hydroxy(lower)alkylamino, provided that m is 1 or 2 in this case.

2. The aromatic amino acid derivative according to claim 1 or its pharmacologically acceptable salt, wherein R$^3$ is selected from the group consisting of:

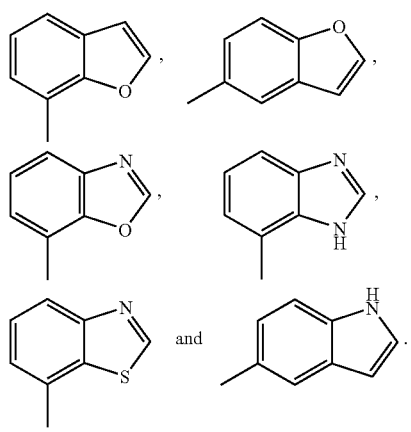

3. The aromatic amino acid derivative according to claim 1 or its pharmacologically acceptable salt, wherein R$^1$ is a hydrogen atom.

4. The aromatic amino acid derivative according to claim 1 or its pharmacologically acceptable salt, wherein the amino protecting group is an acyl group.

5. The aromatic amino acid derivative according to claim 1 or its pharmacologically acceptable salt, wherein said condensed heterocyclic group is optionally substituted with oxo, amino, lower alkyl, di(lower)alkylamino, lower alkoxycarbonyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino or lower alkanoyloxy.

6. The aromatic amino acid derivative according to claim 1 or its pharmacologically acceptable salt, wherein said condensed heterocyclic group is optionally substituted with oxo, lower alkyl, lower alkoxycarbonyl, phenyl or saturated or unsaturated mono-cyclic heterocyclic group containing N, O and/or S, in which each substituent on the condensed heterocyclic group may be further substituted with halogen atom, hydroxyl, lower alkyl, lower alkoxy, di(lower)alkylamino or lower alkanoyloxy.

7. The aromatic amino acid derivative according to claim 1 or its pharmacologically acceptable salt, wherein said condensed heterocyclic group is optionally substituted with oxo, amino, lower alkyl, hydroxyl(lower)alkyl, lower alkoxycarbonyl or phenyl.

8. The aromatic amino acid derivative according to claim 1 or its pharmacologically acceptable salt, wherein said condensed heterocyclic group is substituted with phenyl.

9. The aromatic amino acid derivative according to a claim 1 or its pharmacologically acceptable salt, wherein X is a halogen atom.

10. A pharmaceutical composition comprising, as an active ingredient, the aromatic amino acid derivative of the formula (I) according to claim 1 or its pharmacologically acceptable salt, and one or more pharmaceutically acceptable additives.

11. A composition for inhibiting L-type amino acid transporter comprising, as an active ingredient the aromatic amino acid derivative of the formula (I) according claim 1 or its pharmacologically acceptable salt, and a suitable carrier.

12. An aromatic amino acid derivative represented by formula (I) or its pharmacologically acceptable salt:

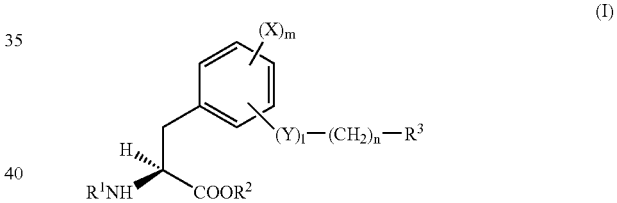

wherein,
X is a halogen atom, an alkyl group or alkoxy group,
Y is O or NH,
l in (Y)$_l$ is 0 or 1,
m is 0, 1 or 2,
n is an integer of 0-5,
R$^1$ is a hydrogen atom or an amino-protecting group,
R$^2$ is a hydrogen atom or an alkyl, aralkyl or aryl group,
R$^3$ is benzodioxole, wherein said R$^3$ group is attached to the (Y)$_l$—(CH$_2$)$_n$— moiety through the benzo moiety thereof, and wherein said condensed heterocyclic group is substituted with oxo, carboxy, amino, lower alkyl, lower alkoxy, cycloalkyl, di(lower)alkylamino, lower alkoxycarbonyl, di(lower)alkylcarbamoyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino, lower alkanoyloxy, bis[halo(lower)alkyl]amino or N-(lower)alkyl-N-hydroxy(lower)alkylamino, provided that m is 1 or 2 in this case.

13. An aromatic amino acid derivative represented by formula (I) or its pharmacologically acceptable salt:

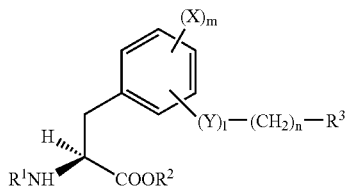

wherein,
X is a halogen atom, an alkyl group or alkoxy group,
Y is O or NH,
l in (Y)$_l$ is 0 or 1,
m is 0, 1 or 2,
n is an integer of 0-5,
R$^1$ is a hydrogen atom or an amino-protecting group,
R$^2$ is a hydrogen atom or an alkyl, aralkyl or aryl group,
R$^3$ is benzodioxole, wherein said R$^3$ group is attached to the (Y)$_l$—(CH$_2$)$_n$— moiety through the benzo moiety thereof, and wherein said condensed heterocyclic group is optionally substituted with oxo, carboxy, amino, lower alkyl, lower alkoxy, cycloalkyl, di(lower)alkylamino, lower alkoxycarbonyl, di(lower)alkylcarbamoyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino, lower alkanoyloxy, bis[halo(lower)alkyl]amino or N-(lower)alkyl-N-hydroxy(lower)alkylamino, provided that m is 1 or 2 in this case.

* * * * *